(12) United States Patent
Kingsman et al.

(10) Patent No.: US 6,541,248 B1
(45) Date of Patent: Apr. 1, 2003

(54) ANTI-VIRAL VECTORS

(75) Inventors: Alan John Kingsman, Islip Oxfordshire (GB); Kyriacos Mitrophanous, Oxford (GB); Narry Kim, Seoul (KR)

(73) Assignee: Oxford BioMedica Limited, Oxford (GB)

( * ) Notice: Subject to any disclaimer, the term of this patent is extended or adjusted under 35 U.S.C. 154(b) by 0 days.

(21) Appl. No.: 09/552,950

(22) Filed: Apr. 20, 2000

Related U.S. Application Data

(63) Continuation-in-part of application No. PCT/GB99/00325, filed on Feb. 17, 1999.

(30) Foreign Application Priority Data

Feb. 17, 1998 (GB) ............................................. 9803352

(51) Int. Cl.$^7$ ........................... C12N 15/00; C12N 15/63
(52) U.S. Cl. ..................... 435/325; 435/69.1; 435/91.4; 435/320.1; 435/455
(58) Field of Search ........................... 435/320.1, 235.1, 435/69.1, 91.4, 455; 514/44; 424/93.2

(56) References Cited

U.S. PATENT DOCUMENTS 5,989,819 A * 11/1999 Odawara ....................... 435/6

FOREIGN PATENT DOCUMENTS

| EP | 0 612 844 A2 | 8/1994 |
| EP | 0 759 471 A1 | 2/1997 |
| WO | WO 97/20060 | 6/1997 |

OTHER PUBLICATIONS

Srinivasakumar et al., Journal of Virology, vol. 71, No. 8, pp. 5841–5848, Aug. 1997.
Sun et al., Nucleic Acids Research, vol. 23, No. 15, pp. 2909–2913, 1995.
Pear et al., Proc. Natl. Acad. Sci., USA, vol. 90, pp. 8392–8396, Sep. 1993.
Naldini et al., Proc. Natl. Acad. Sci., USA, vol. 93, pp. 11382–11388, Oct. 1996.
Poznansky et al., Journal of Virology, vol. 65, No. 1, pp. 532–536, Jan. 1991.
Sczakiel et al., Journal of Virology, vol. 65, No. 1, pp. 468–472, Jan. 1991.
Zhou et al., Antisense and Nucleic Acid Drug Development, vol. 6, pp. 17–24, 1996.
Buchschacher et al., Journal of Virology, vol. 66, No. 5, pp. 2731–2739, May 1992.
Shimada et al., The Journal of Clinical Investigation, Inc., vol. 88, pp. 1043–1047, Sep. 1991.
Malim et al., Cell, vol. 58, pp. 205–214, Jul. 14, 1989.
Chang et al., Cell, vol. 59, pp. 789–795, Dec. 1, 1989.
Goodchild et al., Archives of Biochemistry and Biophysics, vol. 284, No. 2, pp. 386–391, 1991.
Ramezani et al., Antisense & Nucleic Acid Drug Development, vol. 6, pp. 229–235, 1996.
Breaker et al., Tibtech, vol. 12, pp. 268–275, Jul. 1994.
Couture et al., TIG, vol. 12, No. 12, pp. 510–515, Dec. 1996.
Sarver et al., Science, vol. 247, pp. 1222–1225, Mar. 9, 1990.
Naldini et al., Science, vol. 272, pp. 263–267, Apr. 12, 1996.
Chen et al., Nucleic Acids Research, vol. 20, No. 17, pp. 4581–4589, Aug. 11, 1992.
Soneoka et al., Nucleic Acids Research, vol. 23, No. 4, pp. 628–633, 1995.
Miller et al., Human Gene Therapy, vol. 8, pp. 803–815, May 1, 1997.
Liu et al., Journal of Virology, vol. 71, No. 5, pp. 4079–4085, May 1997.
Bahner et al., Journal of Virology, vol. 70, No. 7, pp. 4352–4360, Jul. 1996.
Yu et al., Journal of Virology, vol. 70, No. 7, pp. 4530–4537, Jul. 1996.
Cosset et al., Journal of Virology, vol. 69, No. 12, pp. 7430–7436, Dec. 1995.
Larsson et al., Virology 219, pp. 161–169, Article No. 0233, 1996.
Yamada et al., Virology 205, pp. 121–126, 1994.
Blomer et al., Journal of Virology, vol. 71, No. 9, pp. 6641–6649, Sep. 1997.
Paik et al., Human Gene Therapy, vol. 8, pp. 1115–1124, Jun. 10, 1997.
Zufferey et al., Nature Biotechnology, vol. 15, pp. 871–875, Sep. 1997.
Ory et al., Proc. Natl. Acad. Sci. USA, vol. 93, pp. 11400–11406, Oct. 1996.
Poeschla et al., Proc. Natl. Acad. Sci. USA, vol. 93, pp. 11395–11399, Oct. 1996.

(List continued on next page.)

Primary Examiner—Dave Trong Nguyen
(74) Attorney, Agent, or Firm—Frommer Lawrence & Haug LLP; Thomas J. Kowalski

(57) ABSTRACT

A viral vector production system is provided which system comprises:

(i) a viral genome comprising at least one first nucleotide sequence encoding a gene product capable of binding to and effecting the cleavage, directly or indirectly, of a second nucleotide sequence, or transcription product thereof, encoding a viral polypeptide required for the assembly of viral particles;

(ii) a third nucleotide sequence encoding said viral polypeptide required for the assembly of the viral genome into viral particles, which third nucleotide sequence has a different nucleotide sequence to the second nucleotide sequence such that said third nucleotide sequence, or transcription product thereof, is resistant to cleavage directed by said gene product. The viral vector production system may be used to produce viral particles for use in treating or preventing viral infection.

10 Claims, 27 Drawing Sheets

OTHER PUBLICATIONS

Riddell et al., Nature Medicine, vol. 2, No. 2, pp. 216–223, Feb. 1996.

Haas et al., Current Biology, vol. 6, No. 3, 1996, pp. 315–324, 1996.

Coffin et al., Retroviruses, Cold Spring Harbour Laboratory Press, USA, pp. 758–763, 1997.

Lever, British Medical Bulletin, vol. 51, No. 1, pp. 149–166, 1995.

Haas et al., "Codon usage limitation in the expression of HIV–1 envelope glycoprotein", Current Biology, 1996, vol. 6, No. 3.

* cited by examiner

```
gagpol-HXB2 -> Codon Usage

DNA sequence          4308 b.p.    ATGGGTGAGAGA ... GATGAGGATTAG    linear 1436 codons
    MW : 161929 Dalton      CAI(S.c.) : 0.083    CAI(E.c.) : 0.151

TTT  phe  F  21    TCT  ser  S   3    TAT  tyr  Y  30    TGT  cys  C  18
    TTC  phe  F  14    TCC  ser  S   3    TAC  tyr  Y   9    TGC  cys  C   2
    TTA  leu  L  46    TCA  ser  S  19    TAA  OCH  Z   -    TGA  OPA  Z   -
    TTG  leu  L  11    TCG  ser  S   1    TAG  AMB  Z   1    TGG  trp  W  37

CTT  leu  L  13    CCT  pro  P  21    CAT  his  H  20    CGT  arg  R   -
    CTC  leu  L   7    CCC  pro  P  14    CAC  his  H   7    CGC  arg  R   -
    CTA  leu  L  17    CCA  pro  P  41    CAA  gln  Q  56    CGA  arg  R   3
    CTG  leu  L  16    CCG  pro  P   -    CAG  gln  Q  39    CGG  arg  R   3

ATT  ile  I  30    ACT  thr  T  24    AAT  asn  N  42    AGT  ser  S  18
    ATC  ile  I  14    ACC  thr  T  20    AAC  asn  N  16    AGC  ser  S  16
    ATA  ile  I  56    ACA  thr  T  43    AAA  lys  K  88    AGA  arg  R  45
    ATG  met  M  29    ACG  thr  T   1    AAG  lys  K  34    AGG  arg  R  18

GTT  val  V  15    GCT  ala  A  17    GAT  asp  D  37    GGT  gly  G  11
    GTC  val  V  11    GCC  ala  A  19    GAC  asp  D  26    GGC  gly  G  10
    GTA  val  V  55    GCA  ala  A  55    GAA  glu  E  75    GGA  gly  G  61
    GTG  val  V  15    GCG  ala  A   5    GAG  glu  E  32    GGG  gly  G  26
```

FIG. 3

```
gagpol-SYNgp [1 to 4308] -> Codon Usage

DNA sequence    4308 b.p.    ATGGGCGCCCGC ... GATGAGGATTAG      linear 1436 codons
    MW : 161929 Dalton     CAI(S.c.) : 0.080    CAI(E.c.) : 0.296

TTT  phe  F    5     TCT  ser  S    5     TAT  tyr  Y   10     TGT  cys  C    6
    TTC  phe  F   30     TCC  ser  S   11     TAC  tyr  Y   29     TGC  cys  C   14
    TTA  leu  L    2     TCA  ser  S    4     TAA  OCH  Z    -     TGA  OPA  Z    -
    TTG  leu  L    7     TCG  ser  S    6     TAG  AMB  Z    1     TGG  trp  W   37

CTT  leu  L    3     CCT  pro  P   14     CAT  his  H    6     CGT  arg  R    2
    CTC  leu  L   22     CCC  pro  P   39     CAC  his  H   21     CGC  arg  R   34
    CTA  leu  L    6     CCA  pro  P   10     CAA  gln  Q   14     CGA  arg  R    3
    CTG  leu  L   70     CCG  pro  P   13     CAG  gln  Q   81     CGG  arg  R   10

ATT  ile  I   17     ACT  thr  T   11     AAT  asn  N   13     AGT  ser  S    7
    ATC  ile  I   79     ACC  thr  T   48     AAC  asn  N   45     AGC  ser  S   27
    ATA  ile  I    4     ACA  thr  T   13     AAA  lys  K   25     AGA  arg  R    7
    ATG  met  M   29     ACG  thr  T   16     AAG  lys  K   97     AGG  arg  R   13

GTT  val  V    5     GCT  ala  A   15     GAT  asp  D   19     GGT  gly  G   10
    GTC  val  V   27     GCC  ala  A   56     GAC  asp  D   44     GGC  gly  G   54
    GTA  val  V    6     GCA  ala  A   13     GAA  glu  E   29     GGA  gly  G   16
    GTG  val  V   58     GCG  ala  A   12     GAG  glu  E   78     GGG  gly  G   28
```

FIG. 4

Codon usage in human genes (MH), wild type HIV-1 Gag-pol (WT) and the codon optimised HIV-1 Gag-pol (CO)

|     |    | MH | WT | CO |     |    | MH | WT | CO |     |    | MH | WT | CO |     |    | MH | WT | CO |
|-----|----|----|----|----|-----|----|----|----|----|-----|----|----|----|----|-----|----|----|----|----|
| Ala | A  | 13 | 46 | 8  | Cys | C  | 68 | 10 | 70 | Leu | A  | 3  | 14 | 3  | Ser | C  | 34 | 35 | 55 |
| GC  | C  | 53 | 19 | 65 | TG  | T  | 32 | 90 | 30 | CT  | C  | 26 | 8  | 17 | AG  | T  | 10 | 10 | 3  |
|     | G  | 17 | 11 | 8  |     |    |    |    |    |     | G  | 58 | 14 | 70 | TC  | A  | 5  | 38 | 17 |
|     | T  | 17 | 24 | 19 | Gln | A  | 12 | 53 | 21 |     | T  | 5  | 11 | 6  |     | C  | 28 | 10 | 14 |
|     |    |    |    |    | CA  | G  | 88 | 47 | 79 | TT  | A  | 2  | 42 | 6  |     | G  | 9  | 3  | 7  |
| Arg | A  | 10 | 58 | 10 |     |    |    |    |    |     | G  | 6  | 11 | 0  |     | T  | 13 | 3  | 3  |
| AG  | G  | 18 | 29 | 11 | Glu | A  | 25 | 65 | 38 |     |    |    |    |    |     |    |    |    |    |
| CG  | A  | 6  | 6  | 0  | GA  | G  | 75 | 35 | 62 | Lys | A  | 18 | 58 | 28 | Thr | A  | 14 | 45 | 16 |
|     | C  | 37 | 0  | 61 |     |    |    |    |    | AA  | G  | 82 | 42 | 72 | AC  | C  | 57 | 29 | 52 |
|     | G  | 21 | 6  | 10 | Gly | A  | 14 | 53 | 21 |     |    |    |    |    |     | G  | 15 | 0  | 19 |
|     | T  | 7  | 0  | 5  | GG  | C  | 50 | 21 | 55 | Phe | C  | 80 | 45 | 45 |     | T  | 14 | 26 | 13 |
|     |    |    |    |    |     | G  | 24 | 24 | 24 | TT  | T  | 20 | 55 | 55 |     |    |    |    |    |
| Asn | C  | 78 | 29 | 71 |     | T  | 12 | 3  | 0  |     |    |    |    |    | Tyr | C  | 74 | 20 | 80 |
| AA  | T  | 22 | 71 | 29 |     |    |    |    |    | Pro | A  | 16 | 52 | 24 | TA  | T  | 26 | 80 | 20 |
|     |    |    |    |    | His | C  | 79 | 30 | 90 | CC  | C  | 48 | 15 | 39 |     |    |    |    |    |
| Asp | C  | 75 | 64 | 70 | CA  | T  | 21 | 70 | 10 |     | G  | 17 | 3  | 21 | Val | A  | 5  | 56 | 4  |
| GA  | T  | 25 | 36 | 30 |     |    |    |    |    |     | T  | 19 | 30 | 15 | GT  | C  | 25 | 8  | 20 |
|     |    |    |    |    | Ile | A  | 5  | 58 | 8  |     |    |    |    |    |     | G  | 64 | 24 | 76 |
|     |    |    |    |    | AT  | C  | 18 | 19 | 92 |     |    |    |    |    |     | T  | 7  | 12 | 0  |
|     |    |    |    |    |     | T  | 77 | 23 | 0  |     |    |    |    |    |     |    |    |    |    |

FIG. 4a env-mn [1 to 2571] -> Codon Usage

DNA sequence    2571 b.p.    ATGAGAGTGAAG ... GCTTTGCTATAA    linear 857 codons
    MW : 97078 Dalton        CAI(S.c.) : 0.083    CAI(E.c.) : 0.140

TTT  phe  F  13    TCT  ser  S   7    TAT  tyr  Y  15    TGT  cys  C  16
    TTC  phe  F  11    TCC  ser  S   3    TAC  tyr  Y   7    TGC  cys  C   5
    TTA  leu  L  20    TCA  ser  S  13    TAA  OCH  Z   1    TGA  OPA  Z   -
    TTG  leu  L  17    TCG  ser  S   2    TAG  AMB  Z   -    TGG  trp  W  30

CTT  leu  L   9    CCT  pro  P   5    CAT  his  H   8    CGT  arg  R   -
    CTC  leu  L  11    CCC  pro  P   9    CAC  his  H   6    CGC  arg  R   2
    CTA  leu  L  12    CCA  pro  P  12    CAA  gln  Q  22    CGA  arg  R   1
    CTG  leu  L  15    CCG  pro  P   2    CAG  gln  Q  19    CGG  arg  R   1

ATT  ile  I  21    ACT  thr  T  16    AAT  asn  N  50    AGT  ser  S  18
    ATC  ile  I  10    ACC  thr  T  14    AAC  asn  N  13    AGC  ser  S  11
    ATA  ile  I  32    ACA  thr  T  28    AAA  lys  K  32    AGA  arg  R  30
    ATG  met  M  17    ACG  thr  T   5    AAG  lys  K  14    AGG  arg  R  15

GTT  val  V   8    GCT  ala  A  16    GAT  asp  D  18    GGT  gly  G  10
    GTC  val  V   9    GCC  ala  A   7    GAC  asp  D  14    GGC  gly  G   6
    GTA  val  V  26    GCA  ala  A  20    GAA  glu  E  36    GGA  gly  G  28
    GTG  val  V  12    GCG  ala  A   5    GAG  glu  E  10    GGG  gly  G  12

FIG. 5

SYNgp160mn -> Codon Usage

DNA sequence    2571 b.p.    ATGAGGGTGAAG ... GCGCTGCTGTAA    linear 857 codons

MW : 97078 Dalton    CAI(S.c.) : 0.074    CAI(E.c.) : 0.419

| | | | | | | | | | | | |
|---|---|---|---|---|---|---|---|---|---|---|---|
| TTT | phe | F | - | TCT | ser | S | 2 | TAT | tyr | Y | 1 | TGT | cys | C | - |
| TTC | phe | F | 24 | TCC | ser | S | 4 | TAC | tyr | Y | 21 | TGC | cys | C | 21 |
| TTA | leu | L | - | TCA | ser | S | - | TAA | OCH | Z | 1 | TGA | OPA | Z | - |
| TTG | leu | L | - | TCG | ser | S | - | TAG | AMB | Z | - | TGG | trp | W | 30 |
| CTT | leu | L | - | CCT | pro | P | - | CAT | his | H | 2 | CGT | arg | R | 1 |
| CTC | leu | L | 20 | CCC | pro | P | 26 | CAC | his | H | 12 | CGC | arg | R | 36 |
| CTA | leu | L | 1 | CCA | pro | P | - | CAA | gln | Q | - | CGA | arg | R | - |
| CTG | leu | L | 63 | CCG | pro | P | 2 | CAG | gln | Q | 41 | CGG | arg | R | 4 |
| ATT | ile | I | 2 | ACT | thr | T | - | AAT | asn | N | 2 | AGT | ser | S | - |
| ATC | ile | I | 61 | ACC | thr | T | 59 | AAC | asn | N | 61 | AGC | ser | S | 48 |
| ATA | ile | I | - | ACA | thr | T | - | AAA | lys | K | 1 | AGA | arg | R | 2 |
| ATG | met | M | 17 | ACG | thr | T | 4 | AAG | lys | K | 45 | AGG | arg | R | 6 |
| GTT | val | V | - | GCT | ala | A | - | GAT | asp | D | 2 | GGT | gly | G | 1 |
| GTC | val | V | 1 | GCC | ala | A | 40 | GAC | asp | D | 30 | GGC | gly | G | 47 |
| GTA | val | V | 1 | GCA | ala | A | - | GAA | glu | E | 3 | GGA | gly | G | - |
| GTG | val | V | 53 | GCG | ala | A | 8 | GAG | glu | E | 43 | GGG | gly | G | 8 |

FIG. 6

HIV Constructs

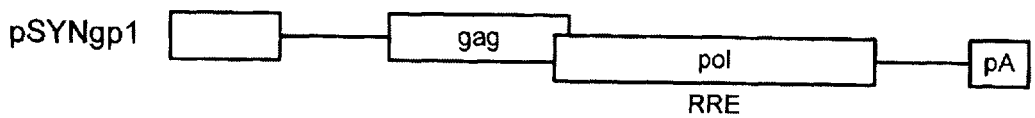

FIG. 7

```
  1 ATGGGCGCCCGCGCCAGCGTGCTGTCGGGCGGCGAGCTGGACCGCTGGGA 50
    |||||  ||  |  ||    ||  |     || || ||  |  || ||  |||||
  1 ATGGGTGCGAGAGCGTCAGTATTAAGCGGGGGAGAATTAGATCGATGGGA 50

51 GAAGATCCGCCTGCGCCCCGGCGGCAAAAAGAAGTACAAGCTGAAGCACA 100
    ||  || ||  |    | ||  ||  ||  ||  || ||  | ||  || |
 51 AAAAATTCGGTTAAGGCCAGGGGGAAAGAAAAAATATAAATTAAAACATA 100

101 TCGTGTGGGCCAGCCGCGAACTGGAGCGCTTCGCCGTGAACCCCGGGCTC 150
    |  ||  ||||| ||| |  ||  ||  || ||  |||||  ||  || ||
101 TAGTATGGGCAAGCAGGGAGCTAGAACGATTCGCAGTTAATCCTGGCCTG 150

151 CTGGAGACCAGCGAGGGGTGCCGCCAGATCCTCGGCCAACTGCAGCCCAG 200
    |  ||  ||   ||  ||  ||  |    || || || || || || ||  ||
151 TTAGAAACATCAGAAGGCTGTAGACAAATACTGGGACAGCTACAACCATC 200

201 CCTGCAAACCGGCAGCGAGGAGCTGCGCAGCCTGTACAACACCGTGGCCA 250
    ||| ||  || || ||    || || ||  |     | ||  || || ||  |
201 CCTTCAGACAGGATCAGAAGAACTTAGATCATTATATAATACAGTAGCAA 250

251 CGCTGTACTGCGTCCACCAGCGCATCGAAATCAAGGATACGAAAGAGGCC 300
    |  || || ||  || || || ||  |  || || || || || || || ||
251 CCCTCTATTGTGTGCATCAAAGGATAGAGATAAAAGACACCAAGGAAGCT 300

301 CTGGATAAAATCGAAGAGGAACAGAATAAGAGCAAAAAGAAGGCCCAACA 350
    |  || ||  || || ||  || || || ||  || || || || || ||
301 TTAGACAAGATAGAGGAAGAGCAAAACAAAAGTAAGAAAAAGCACAGCA 350

351 GGCCGCCGCGGACACCGGACACAGCAACCAGGTCAGCCAGAACTACCCCA 400
    ||  ||  ||  |||||  |||||||||||  |||||||||| ||  |||||  |
351 AGCAGCAGCTGACACAGGACACAGCAATCAGGTCAGCCAAAATTACCCTA 400

401 TCGTGCAGAACATCCAGGGGCAGATGGTGCACCAGGCCATCTCCCCCCGC 450
    |  |||||||||||||||||||||  |||||  || |||||||| || ||  |
401 TAGTGCAGAACATCCAGGGGCAAATGGTACATCAGGCCATATCACCTAGA 450

451 ACGCTGAACGCCTGGGTGAAGGTGGTGGAAGAGAAGGCTTTTAGCCCGGA 500
    ||  |  || ||  ||||| || || ||  ||||||||||||||  ||||| ||
451 ACTTTAAATGCATGGGTAAAAGTAGTAGAAGAGAAGGCTTTCAGCCCAGA 500

501 GGTGATACCCATGTTCTCAGCCCTGTCAGAGGGAGCCACCCCCAAGATC 550
    ||||||||||||| |||||  | ||||| |||||||||||||| ||||||
501 AGTGATACCCATGTTTTCAGCATTATCAGAAGGAGCCACCCCACAAGATT 550

551 TGAACACCATGCTCAACACAGTGGGGGGACACCAGGCCGCCATGCAGATG 600
    | ||||||||||||| ||||||||||||||||  |  || || |||||||| |||
551 TAAACACCATGCTAAACACAGTGGGGGGACATCAAGCAGCCATGCAAATG 600
```

FIG. 9A

```
601 CTGAAGGAGACCATCAATGAGGAGGCTGCCGAATGGGATCGTGTGCATCC 650
    |  || |||||||||||||||||| |||||  ||||||||| | ||||||||
601 TTAAAAGAGACCATCAATGAGGAAGCTGCAGAATGGGATAGAGTGCATCC 650

651 GGTGCACGCAGGGCCCATCGCACCGGGCCAGATGCGTGAGCCACGGGGCT 700
    |||||  |||||||||  || |||||  |||||||||| | || ||| ||||
651 AGTGCATGCAGGGCCTATTGCACCAGGCCAGATGAGAGAACCAAGGGGAA 700

701 CAGACATCGCCGGAACGACTAGTACCCTTCAGGAACAGATCGGCTGGATG 750
    ||||| || ||||||  |||||||||||||||||||||||  || || ||||||
701 GTGACATAGCAGGAACTACTAGTACCCTTCAGGAACAAATAGGATGGATG 750

751 ACCAACAACCCACCCATCCCGGTGGGAGAAATCTACAAACGCTGGATCAT 800
    || || || ||||| |||||  |||||||| || ||| | ||||| ||
751 ACAAATAATCCACCTATCCCAGTAGGAGAAATTTATAAAGATGGATAAT 800

801 CCTGGGCCTGAACAAGATCGTGCGCATGTATAGCCCTACCAGCATCCTGG 850
    ||||||  | || || || || |  |  |||||||||||||||||||| ||||
801 CCTGGGATTAAATAAAATAGTAAGAATGTATAGCCCTACCAGCATTCTGG 850

851 ACATCCGCCAAGGCCCGAAGGAACCCTTTCGCGACTACGTGGACCGGTTC 900
    |||| | |||||| || || |||||||||| | |||||| || ||||||||
851 ACATAAGACAAGGACCAAAAGAACCCTTTAGAGACTATGTAGACCGGTTC 900

901 TACAAAACGCTCCGCGCCGAGCAGGCTAGCCAGGAGGTGAAGAACTGGAT 950
    || |||||| ||  | ||||||||| |||   |||||||| || || |||||
901 TATAAAACTCTAAGAGCCGAGCAAGCTTCACAGGAGGTAAAAAATTGGAT 950

951 GACCGAAACCCTGCTGGTCCAGAACGCGAACCCGGACTGCAAGACGATCC 1000
    |||  |||||| || ||||||| || |||||||| || || ||||| ||
951 GACAGAAACCTTGTTGGTCCAAAATGCGAACCCAGATTGTAAGACTATTT 1000

1001 TGAAGGCCCTGGGCCCAGCGGCTACCCTAGAGGAAATGATGACCGCCTGT 1050
     | || ||  |||| ||||||||||| ||||| ||||||||||||| || |||
1001 TAAAAGCATTGGGACCAGCGGCTACACTAGAAGAAATGATGACAGCATGT 1050

1051 CAGGGAGTGGGCGGACCCGGCCACAAGGCACGCGTCCTGGCTGAGGCCAT 1100
     |||||||| || |||||||||||| ||||| | || ||||||| || ||
1051 CAGGGAGTAGGAGGACCCGGCCATAAGGCAAGAGTTTTGGCTGAAGCAAT 1100

1101 GAGCCAGGTGACCAACTCCGCTACCATCATGATGCAGCGCGGCAACTTTC 1150
     ||||||| || || || || ||||||||| |||||||| |  ||||| |||
1101 GAGCCAAGTAACAAATTCAGCTACCATAATGATGCAGAGAGGCAATTTTA 1150

1151 GGAACCAACGCAAGATCGTCAAGTGCTTCAACTGTGGCAAAGAAGGGCAC 1200
     |||||||| | ||||| || ||||| ||||| |||||||||||||||||||
1151 GGAACCAAAGAAAGATTGTTAAGTGTTTCAATTGTGGCAAAGAAGGGCAC 1200
```

FIG. 9B

```
1201 ACAGCCCGCAACTGCAGGGCCCCTAGGAAAAAGGGCTGTTGGAAATGTGG 1250
     |||||  || |||||||||||||||||||||||||||||||||||||||
1201 ACAGCCAGAAATTGCAGGGCCCCTAGGAAAAAGGGCTGTTGGAAATGTGG 1250

1251 AAAGGAAGGACACCAAATGAAAGATTGTACTGAGAGACAGGCTAATTTTT 1300
     |||||||||||||||||||||||||||||||||||||||||||||||||
1251 AAAGGAAGGACACCAAATGAAAGATTGTACTGAGAGACAGGCTAATTTTT 1300

1301 TAGGGAAGATCTGGCCTTCCCACAAGGGAAGGCCAGGGAATTTTCTTCAG 1350
     ||||||||||||||||||||| ||||||||||||||||||||||||||
1301 TAGGGAAGATCTGGCCTTCCTACAAGGGAAGGCCAGGGAATTTTCTTCAG 1350

1351 AGCAGACCAGAGCCAACAGCCCCACCAGAAGAGAGCTTCAGGTTTGGGA 1400
     |||||||||||||||||||||||||||||||||||||||||| |||||
1351 AGCAGACCAGAGCCAACAGCCCCACCAGAAGAGAGCTTCAGGTCTGGGGT 1400

1401 AGAGACAACAACTCCCTCTCAGAAGCAGGAGCCGATAGACAAGGAACTGT 1450
     ||||||||||||||| |||||||||||||||||||||||||||||||||
1401 AGAGACAACAACTCCCCCTCAGAAGCAGGAGCCGATAGACAAGGAACTGT 1450

1451 ATCCTTTAGCTTCCCTCAGATCACTCTTTGGCAGCGACCCCTCGTCACAA 1500
     ||||||| |||||||||||||||||||||| |||||||||||||||||
1451 ATCCTTTAACTTCCCTCAGATCACTCTTTGGCAACGACCCCTCGTCACAA 1500

1501 TAAAGATAGGGGGGCAGCTCAAGGAGGCTCTCCTGGACACCGGAGCAGAC 1550
     |||||||||||||||  ||||| ||||| |   |  || || ||||||
1501 TAAAGATAGGGGGGCAACTAAAGGAAGCTCTATTAGATACAGGAGCAGAT 1550

1551 GACACCGTGCTGGAGGAGATGTCGTTGCCAGGCCGCTGGAAGCCGAAGAT 1600
     || || ||  | || ||  |||       ||||||||| | ||||| || || ||
1551 GATACAGTATTAGAAGAAATGAGTTTGCCAGGAAGATGGAAACCAAAAAT 1600

1601 GATCGGGGGAATCGGCGGTTTCATCAAGGTGCGCCAGTATGACCAGATCC 1650
     ||| |||||||| || ||||| ||||| ||  | ||||||||| |||| |
1601 GATAGGGGGAATTGGAGGTTTTATCAAAGTAAGACAGTATGATCAGATAC 1650

1651 TCATCGAAATCTGCGGCCACAAGGCTATCGGTACCGTGCTGGTGGGCCCC 1700
     |||| ||||||| || ||  || |||| ||||| || |||| ||
1651 TCATAGAAATCTGTGGACATAAAGCTATAGGTACAGTATTAGTAGGACCT 1700

1701 ACACCCGTCAACATCATCGGACGCAACCTGTTGACGCAGATCGGTTGCAC 1750
     ||||| ||||||||| ||  || || ||||||||| |||| |||||| |||||||||
1701 ACACCTGTCAACATAATTGGAAGAAATCTGTTGACTCAGATTGGTTGCAC 1750

1751 GCTGAACTTCCCCATTAGCCCTATCGAGACGGTACCGGTGAAGCTGAAGC 1800
     | || || |||||||||||||| ||||| ||||| || ||  | ||||
1751 TTTAAATTTTCCCATTAGCCCTATTGAGACTGTACCAGTAAAATTAAAGC 1800
```

FIG. 9C

```
1801 CCGGGATGGACGGCCCGAAGGTCAAGCAATGGCCATTGACAGAGGAGAAG 1850
     |  |  |||||  |||||  ||  ||  ||  |||||||||||||||||  ||  ||
1801 CAGGAATGGATGGCCCAAAAGTTAAACAATGGCCATTGACAGAAGAAAAA 1850

1851 ATCAAGGCACTGGTGGAGATTTGCACAGAGATGGAAAAGGAAGGGAAAAT 1900
     ||  ||  |||  |  ||  ||  |||||  ||||||||||||||||||||||||||
1851 ATAAAAGCATTAGTAGAAATTTGTACAGAGATGGAAAAGGAAGGGAAAAT 1900

1901 CTCCAAGATTGGGCCTGAGAACCCGTACAACACGCCGGTGTTCGCAATCA 1950
     ||  ||  ||||||||||  ||  ||  |||||  ||  ||  ||  ||  ||  ||  |
1901 TTCAAAAATTGGGCCTGAAAATCCATACAATACTCCAGTATTTGCCATAA 1950

1951 AGAAGAAGGACTCGACGAAATGGCGCAAGCTGGTGGACTTCCGCGAGCTG 2000
     ||||  ||  |||     ||  |||||||  |  ||   |  ||  ||  |||  |  ||  ||
1951 AGAAAAAGACAGTACTAAATGGAGAAAATTAGTAGATTTCAGAGAACTT 2000

2001 AACAAGCGCACGCAAGACTTCTGGGAGGTTCAGCTGGGCATCCCGCACCC 2050
     ||  |||  |  ||  |||||||||||||||||||||  |||||  |  ||  ||  ||  ||  ||
2001 AATAAGAGAACTCAAGACTTCTGGGAAGTTCAATTAGGAATACCACATCC 2050

2051 CGCAGGGCTGAAGAAGAAGAAATCCGTGACCGTACTGGATGTGGGTGATG 2100
     |||||||  |  ||  |||||  |||||  ||  ||  |||||||||||||||||||
2051 CGCAGGGTTAAAAAGAAAAAATCAGTAACAGTACTGGATGTGGGTGATG 2100

2101 CCTACTTCTCCGTTCCCCTGGACGAAGACTTCAGGAAGTACACTGCCTTC 2150
     |  ||  ||  ||  ||||||  |  ||  ||||||||||||||||  ||  |||||  ||
2101 CATATTTTCAGTTCCCTTAGATGAAGACTTCAGGAAATATACTGCATTT 2150

2151 ACAATCCCTTCGATCAACAACGAGACACCGGGGATTCGATATCAGTACAA 2200
     ||  ||  |||     ||  ||||||  ||||||||  ||||||  |||||||||||||
2151 ACCATACCTAGTATAAACAATGAGACACCAGGGATTAGATATCAGTACAA 2200

2201 CGTGCTGCCCCAGGGCTGGAAAGGCTCTCCCGCAATCTTCCAGAGTAGCA 2250
     |||||  ||  |||||  ||||||||  ||  |||||  |||||  |||||  |||||||
2201 TGTGCTTCCACAGGGATGGAAAGGATCACCAGCAATATTCCAAAGTAGCA 2250

2251 TGACCAAAATCCTGGAGCCTTTCCGCAAACAGAACCCCGACATCGTCATC 2300
     ||||  ||||||  |  |||||||  ||  ||  ||  |||||  ||  ||  ||  |||
2251 TGACAAAAATCTTAGAGCCTTTTAGAAAACAAAATCCAGACATAGTTATC 2300

2301 TATCAGTACATGGATGACTTGTACGTGGGCTCTGATCTAGAGATAGGGCA 2350
     |||||  ||||||||||  |||||  ||  ||  |||||  ||||  ||||||||
2301 TATCAATACATGGATGATTTGTATGTAGGATCTGACTTAGAAATAGGGCA 2350

2351 GCACCGCACCAAGATCGAGGAGCTGCGCCAGCACCTGTTGAGGTGGGGAC 2400
     |||  |  ||  ||  ||  ||||||||||  |  ||  ||  |||||||||||||||||
2351 GCATAGAACAAAAATAGAGGAGCTGAGACAACATCTGTTGAGGTGGGGAC 2400
```

FIG. 9D

```
2401 TGACCACACCCGACAAGAAGCACCAGAAGGAGCCTCCCTTCCTCTGGATG 2450
     |||||||||  |||||  |  ||  ||||| |||  |||||  |||| |||||
2401 TTACCACACCAGACAAAAAACATCAGAAGAACCTCCATTCCTTTGGATG 2450

2451 GGTTACGAGCTGCACCCTGACAAATGGACCGTGCAGCCTATCGTGCTGCC 2500
     |||||  ||  ||  ||||| |||||||| ||  |||||||| ||||||||
2451 GGTTATGAACTCCATCCTGATAAATGGACAGTACAGCCTATAGTGCTGCC 2500

2501 AGAGAAAGACAGCTGGACTGTCAACGACATACAGAAGCTGGTGGGGAAGT 2550
     ||| ||||||||||||||||||||| |||||||||||| | ||||||||| |
2501 AGAAAAAGACAGCTGGACTGTCAATGACATACAGAAGTTAGTGGGGAAAT 2550

2551 TGAACTGGGCCAGTCAGATTTACCCAGGGATTAAGGTGAGGCAGCTGTGC 2600
     |||| ||||| |||||||||||||||||||||||| || |||||   | ||
2551 TGAATTGGGCAAGTCAGATTTACCCAGGGATTAAAGTAAGGCAATTATGT 2600

2601 AAACTCCTCCGCGGAACCAAGGCACTCACAGAGGTGATCCCCCTAACCGA 2650
     |||||||  |  |||||||| |||||| ||||||| || || || ||||| ||
2601 AAACTCCTTAGAGGAACCAAAGCACTAACAGAAGTAATACCACTAACAGA 2650

2651 GGAGGCCGAGCTCGAACTGGCAGAAAACCGAGAGATCCTAAAGGAGCCCG 2700
     || || |||||  |||||||||||||||| ||||||| ||||| ||  || |
2651 AGAAGCAGAGCTAGAACTGGCAGAAAACAGAGAGATTCTAAAAGAACCAG 2700

2701 TGCACGGCGTGTACTATGACCCCTCCAAGGACCTGATCGCCGAGATCCAG 2750
     | || || ||||| ||||||||| |||||  ||  || || || || || |||
2701 TACATGGAGTGTATTATGACCCATCAAAAGACTTAATAGCAGAAATACAG 2750

2751 AAGCAGGGGCAAGGCCAGTGGACCTATCAGATTTACCAGGAGCCCTTCAA 2800
     |||||||||||||||||| |||||  |||||  ||||| ||  ||||||| || ||
2751 AAGCAGGGGCAAGGCCAATGGACATATCAAATTTATCAAGAGCCATTTAA 2800

2801 GAACCTGAAGACCGGCAAGTACGCCCGGATGAGGGGTGCCCACACTAACG 2850
     || |||||| || || || || || ||  | ||||||||||||||||||||| |
2801 AAATCTGAAAACAGGAAAATATGCAAGAATGAGGGGTGCCCACACTAATG 2850

2851 ACGTCAAGCAGCTGACCGAGGCCGTGCAGAAGATCACCACCGAAAGCATC 2900
     |  || || ||  | || ||||| ||||| || || |||||| ||||||||
2851 ATGTAAAACAATTAACAGAGGCAGTGCAAAAAATAACCACAGAAAGCATA 2900

2901 GTGATCTGGGGAAAGACTCCTAAGTTCAAGCTGCCCATCCAGAAGGAAAC 2950
     || ||  |||||||||||||||| || || ||||||||| || ||||||||
2901 GTAATATGGGGAAAGACTCCTAAATTTAAACTGCCCATACAAAAGGAAAC 2950

2951 CTGGGAAACCTGGTGGACAGAGTATTGGCAGGCCACCTGGATTCCTGAGT 3000
     ||||||||  ||||||||||||||||||||| ||||||||||||||||||||
2951 ATGGGAAACATGGTGGACAGAGTATTGGCAAGCCACCTGGATTCCTGAGT 3000
```

FIG. 9E

```
3001 GGGAGTTCGTCAACACCCCTCCCCTGGTGAAGCTGTGGTACCAGCTGGAG 3050
     |||||||  || ||  ||||||||  |  |||||  |  ||||||||||  |  |||
3001 GGGAGTTTGTTAATACCCCTCCTTTAGTGAATTATGGTACCAGTTAGAG 3050

3051 AAGGAGCCCATAGTGGGCGCCGAAACCTTCTACGTGGATGGGGCCGCTAA 3100
     ||  ||  ||||||||  || ||  ||||||||||||  ||  ||||||||  |||||
3051 AAAGAACCCATAGTAGGAGCAGAAACCTTCTATGTAGATGGGGCAGCTAA 3100

3101 CAGGGAGACTAAGCTGGGCAAAGCCGGATACGTCACTAACCGGGGCAGAC 3150
     ||||||||||  |  ||  ||||||  |||||  ||  |||||  |  || ||||
3101 CAGGGAGACTAAATTAGGAAAAGCAGGATATGTTACTAATAGAGGAAGAC 3150

3151 AGAAGGTTGTCACCCTCACTGACACCACCAACCAGAAGACTGAGCTGCAG 3200
     |  ||  ||||||||||||| |||||||| || ||  ||||||||||||||||  |  ||
3151 AAAAGTTGTCACCCTAACTGACACAACAAATCAGAAGACTGAGTTACAA 3200

3201 GCCATTTACCTCGCTTTGCAGGACTCGGGCCTGGAGGTGAACATCGTGAC 3250
     || ||||||  ||  ||||||||||||| |||||  |  || ||  |||||  || ||
3201 GCAATTTATCTAGCTTTGCAGGATTCGGGATTAGAAGTAAACATAGTAAC 3250

3251 AGACTCTCAGTATGCCCTGGGCATCATTCAAGCCCAGCCAGACCAGAGTG 3300
     ||||||  ||  ||||||  |  ||  |||||||||||  ||  ||||| ||  ||||
3251 AGACTCACAATATGCATTAGGAATCATTCAAGCACAACCAGATCAAAGTG 3300

3301 AGTCCGAGCTGGTCAATCAGATCATCGAGCAGCTGATCAAGAAGGAAAAG 3350
     |  ||  |||  |  |||||||||  || ||||||  |  ||  || ||||||||
3301 AATCAGAGTTAGTCAATCAAATAATAGAGCAGTTAATAAAAAAGGAAAAG 3350

3351 GTCTATCTGGCCTGGGTACCCGCCCACAAAGGCATTGGCGGCAATGAGCA 3400
     ||||||||||  ||||||||  || ||||||||||  ||  ||  || ||||  ||
3351 GTCTATCTGGCATGGGTACCAGCACACAAAGGAATTGGAGGAAATGAACA 3400

3401 GGTCGACAAGCTGGTCTCGGCTGGCATCAGGAAGGTGCTATTCCTGGATG 3450
     ||  ||  ||  |  |||     |||||  ||||||| ||  |||||  |  ||||
3401 AGTAGATAAATTAGTCAGTGCTGGAATCAGGAAAGTACTATTTTTAGATG 3450

3451 GCATCGACAAGGCCCAGGACGAGCACGAGAAATACCACAGCAACTGGCGG 3500
     |  || ||  |||||||  ||  ||  ||  |||||||||  ||||| || |||  |
3451 GAATAGATAAGGCCCAAGATGAACATGAGAAATATCACAGTAATTGGAGA 3500

3501 GCCATGGCTAGCGACTTCAACCTGCCCCCTGTGGTGGCCAAAGAGATCGT 3550
     ||  ||||||||  ||  ||||||||||  ||||||  || |||||||  ||  ||
3501 GCAATGGCTAGTGATTTTAACCTGCCACCTGTAGTAGCAAAAGAAATAGT 3550

3551 GGCCAGCTGTGACAAGTGTCAGCTCAAGGGCGAAGCCATGCATGGCCAGG 3600
     ||||||||||||  ||  ||||||||||  ||  |||||||||||||||||  ||  |
3551 AGCCAGCTGTGATAAATGTCAGCTAAAAGGAGAAGCCATGCATGGACAAG 3600
```

FIG. 9F

```
3601 TGGACTGTAGCCCCGGCATCTGGCAACTCGATTGCACCCATCTGGAGGGC 3650
     ||||||||| || || || ||||||||| ||||| || ||| | || ||
3601 TAGACTGTAGTCCAGGAATATGGCAACTAGATTGTACACATTTAGAAGGA 3650

3651 AAGGTTATCCTGGTAGCCGTCCATGTGGCCAGTGGCTACATCGAGGCCGA 3700
     || ||||||||||||| || |||||| |||||||| || || || || ||
3651 AAAGTTATCCTGGTAGCAGTTCATGTAGCCAGTGGATATATAGAAGCAGA 3700

3701 GGTCATTCCCGCCGAAACAGGGCAGGAGACAGCCTACTTCCTCCTGAAGC 3750
     || ||||| || ||||||||||||||| ||||| || || || | ||
3701 AGTTATTCCAGCAGAAACAGGGCAGGAAACAGCATATTTTCTTTTAAAAT 3750

3751 TGGCAGGCCGGTGGCCAGTGAAGACCATCCATACTGACAATGGCAGCAAT 3800
     | ||||| | |||||||| || || || ||||| |||||||||||||||
3751 TAGCAGGAAGATGGCCAGTAAAAACAATACATACAGACAATGGCAGCAAT 3800

3801 TTCACCAGTGCTACGGTTAAGGCCGCCTGCTGGTGGGCGGGAATCAAGCA 3850
     ||||||||||||||||||||||||||||| |||||||||||||||||||
3801 TTCACCAGTGCTACGGTTAAGGCCGCCTGTTGGTGGGCGGGAATCAAGCA 3850

3851 GGAGTTCGGGATCCCCTACAATCCCCAGAGTCAGGGCGTCGTCGAGTCTA 3900
     ||| || || || ||||||||||||| ||||| || || || || ||||
3851 GGAATTTGGAATTCCCTACAATCCCCAAAGTCAAGGAGTAGTAGAATCTA 3900

3901 TGAATAAGGAGTTAAAGAAGATTATCGGCCAGGTCAGAGATCAGGCTGAG 3950
     ||||||| || |||||||| ||||| || ||||| |||||||||||||
3901 TGAATAAAGAATTAAAGAAAATTATAGGACAGGTAAGAGATCAGGCTGAA 3950

3951 CATCTCAAGACCGCGGTCCAAATGGCGGTATTCATCCACAATTTCAAGCG 4000
     ||||| ||||| || ||| || ||||||||||||||||||||||| ||
3951 CATCTTAAGACAGCAGTACAAATGGCAGTATTCATCCACAATTTTAAAAG 4000

4001 GAAGGGGGGGATTGGGGGGTACAGTGCGGGGGAGCGGATCGTGGACATCA 4050
     || ||||||||||||||||||||||||| ||||| | || || ||||| |
4001 AAAAGGGGGGATTGGGGGGTACAGTGCAGGGGAAAGAATAGTAGACATAA 4050

4051 TCGCGACCGACATCCAGACTAAGGAGCTGCAAAAGCAGATTACCAAGATT 4100
     | || || ||||| || ||||| || | |||||| || ||||| || |||
4051 TAGCAACAGACATACAAACTAAAGAATTACAAAAACAAATTACAAAAATT 4100

4101 CAGAATTTCCGGGTCTACTACAGGGACAGCAGAAATCCCCTCTGGAAAGG 4150
     || ||||| ||||| || |||||||||||||||||| ||  ||||||||
4101 CAAAATTTTCGGGTTTATTACAGGGACAGCAGAAATCCACTTTGGAAAGG 4150

4151 CCCAGCGAAGCTCCTCTGGAAGGGTGAGGGGGCAGTAGTGATCCAGGATA 4200
     ||||| ||||||||||||||||| |||||||||||||| || || ||||
4151 ACCAGCAAAGCTCCTCTGGAAAGGTGAAGGGGCAGTAGTAATACAAGATA 4200
```

FIG. 9G

```
4201 ATAGCGACATCAAGGTGGTGCCCAGAAGAAAGGCGAAGATCATTAGGGAT 4250
     ||||  ||||| || || ||||| |||||||| || |||||||||||||
4201 ATAGTGACATAAAAGTAGTGCCAAGAAGAAAAGCAAAGATCATTAGGGAT 4250

4251 TATGGCAAACAGATGGCGGGTGATGATTGCGTGGCGAGCAGACAGGATGA 4300
     ||||| ||||||||||| |||||||||| ||||| || |||||||||||
4251 TATGGCAAAACAGATGGCAGGTGATGATTGTGTGGCAAGTAGACAGGATGA 4300

4301 GGATTAG 4307
     |||||||
4301 GGATTAG 4307
``` pSYN6    CMVp——Syn *gp*——HXB2 *gag*——pA pSYN7    CMVp——Syn *gp*——HXB2 *gag,r*——pA pSYN8    CMVp——Syn *gp*—— *Lac Z*——pA pSYN9    CMVp——HXB2 *gag*——Syn *gp*——pA pSYN10   CMVp——HXB2 *gag*——Syn *gp*——RRE——pA pSYN11   CMVp——HXB2 *gag,r*——Syn *gp*——RRE——pA pSYN12   CMVp——HXB2 *gag*-ΔATG——Syn *gp*——pA pSYN13   CMVp——HXB2 *gag*-fr.sh.——Syn *gp*——pA pSYN14   CMVp——HXB2 *gag*-ΔATG——Syn *gp*——RRE——pA pSYN15   CMVp——HXB2 *gag* 625-1503——Syn *gp*——pA pSYN17   CMVp——HXB2 *gag* 1-625——Syn *gp*——pA

FIG. 14

A. pH6nZ (15μg) + pSYNGP (5μg)
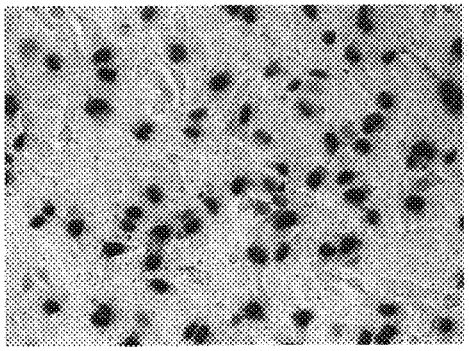
B. pH6nZ (15μg) + pSYNGP (0.5μg)
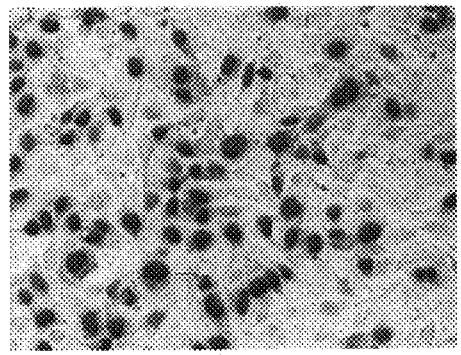
C. pH6nZ (15μg) + pGP-RRE3 (5μg)
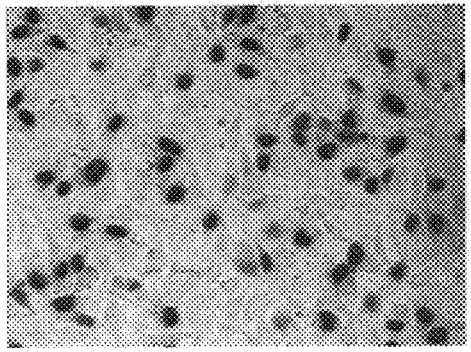
D. pHS3nZ (15μg) + pSYNGP (0.5μg)
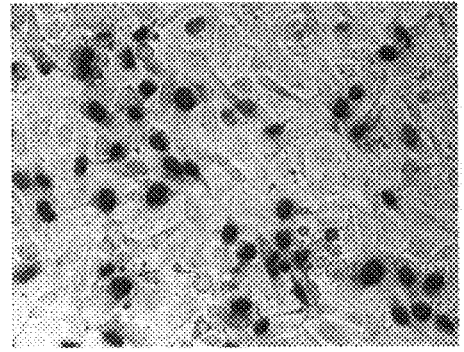
FIG. 18

| Amount of pH6nZ (μg) | Ratio of gagpol expression plasmid to pH6nZ (μg/μg) | Titre, pGP-RRE3 | Titre, pSYNGP | Titre, pSYNGP-RRE | Titre, pSYNGP-ERR |
|---|---|---|---|---|---|
| 5 | 1:1 | $6 \times 10^5$ | $5 \times 10^5$ | $4 \times 10^5$ | $3 \times 10^5$ |
| 12.5 | 1:2.5 | $8 \times 10^5$ | $6.5 \times 10^5$ | | |
| 10 | 1:10 | $3 \times 10^5$ | $4 \times 10^5$ | | |
| 5 | 1:20 | $3.5 \times 10^5$ | $2.5 \times 10^5$ | | |
| 12.5 | 1:50 | $3.5 \times 10^4$ | $3 \times 10^5$ | $3 \times 10^5$ | $3 \times 10^5$ |
| 18 | 1:180 | $2.5 \times 10^4$ | $3 \times 10^5$ | | |

FIG. 21

| Gag-pol expression vector | Vector genome | Rev expression | Titre (IU/ml) [a] |
|---|---|---|---|
| pGP-RRE3 | pH6nZ | Yes / from pH6Z | $8.0 \pm 0.2 \times 10^5$ |
| pGP-RRE3 | pH6.1nZ | No | $2.1 \pm 0.3 \times 10^3$ |
| pGP-RRE3 | pH6.1nZ | Yes / from pCMV-Rev | $4.1 \pm 0.3 \times 10^4$ |
| pGP-RRE3 | pH6.2nZ | No | $1.7 \pm 0.4 \times 10^3$ |
| pGP-RRE3 | pH6.2nZ | Yes / from pCMV-Rev | $5.6 \pm 0.3 \times 10^4$ |
| pSYNGP | pH6nZ | Yes / from pH6Z | $7.8 \pm 0.2 \times 10^5$ |
| pSYNGP | pH6.1nZ | No | $5.4 \pm 0.3 \times 10^4$ |
| pSYNGP | pH6.1nZ | Yes / from pCMV-Rev | $5.2 \pm 0.4 \times 10^4$ |
| pSYNGP | pH6.2nZ | No | $5.0 \pm 0.2 \times 10^4$ |
| pSYNGP | pH6.2nZ | Yes / from pCMV-Rev | $5.5 \pm 0.3 \times 10^4$ |

FIG. 22

| Vector genome | Gag length (nt) | SD mutation | pSYNGP | pGP-RRE3 | pGP-RRE + Rev * |
|---|---|---|---|---|---|
| pH6nZ | 625 | No | $6.7 \pm 0.7 \times 10^5$ | Not done | Not done |
| pH6.1nZ | 625 | No | $3.2 \pm 0.1 \times 10^4$ | Not done | Not done |
| pH6.2nZ | 527 | No | $2.7 \pm 0.3 \times 10^4$ | Not done | Not done |
| pHS1nZ | 40 | No | $2.1 \pm 0.4 \times 10^4$ | $2.1 \pm 0.9 \times 10^3$ | $1.4 \pm 0.3 \times 10^4$ |
| pHS2nZ | 260 | No | $1.5 \pm 0.3 \times 10^4$ | $4.2 \pm 0.6 \times 10^3$ | $3.0 \pm 0.5 \times 10^4$ |
| pHS3nZ | 360 | No | $1.3 \pm 0.3 \times 10^5$ | $6.5 \pm 0.7 \times 10^3$ | $1.7 \pm 0.4 \times 10^5$ |
| pHS4nZ | 625 | No | $1.0 \pm 0.9 \times 10^4$ | $1.2 \pm 0.7 \times 10^3$ | $1.0 \pm 0.3 \times 10^4$ |
| pHS5nZ | 40 | Yes | $2.0 \pm 0.5 \times 10^4$ | $6.0 \pm 0.8 \times 10^2$ | $2.3 \pm 0.5 \times 10^4$ |
| pHS6nZ | 260 | Yes | $1.0 \pm 0.2 \times 10^4$ | $8.1 \pm 0.6 \times 10^2$ | $1.0 \pm 0.4 \times 10^4$ |
| pHS7nZ | 360 | Yes | $1.9 \pm \times 10^4$ | $2.4 \pm 0.9 \times 10^3$ | $4.2 \pm 0.8 \times 10^4$ |
| pHS8nZ | 625 | Yes | $8.0 \pm 1.0 \times 10^3$ | $1.0 \pm 0.5 \times 10^3$ | $4.0 \pm 0.9 \times 10^3$ |

FIG. 23

| Vector genome | pSYNGP | PSYNGP + Rev * |
|---|---|---|
| pH6nZ | $6.5 \times 10^5$ | $6.9 \times 10^5$ |
| pH6.1nZ | $1.5 \times 10^4$ | $1.7 \times 10^4$ |
| pH6.1nZR | $2.3 \times 10^3$ | $1.6 \times 10^5$ |
| pHS1nZ | $8.5 \times 10^3$ | $8.4 \times 10^3$ |
| pHS1nZR | $8.1 \times 10^3$ | $8.8 \times 10^4$ |
| pHS3nZ | $1.2 \times 10^5$ | $1.4 \times 10^5$ |
| pHS3nZR | $2.5 \times 10^3$ | $4.8 \times 10^5$ |
| pHS7nZ | $7.3 \times 10^3$ | $7.0 \times 10^3$ |
| pHS7nZR | $3.4 \times 10^3$ | $5.8 \times 10^3$ |

FIG. 24

ANTI-VIRAL VECTORS

RELATED APPLICATIONS

This application is a continuation-in-part of PCT/GB99/00325, filed Feb. 17, 1999, designating the U.S., published as WO 99/41397 on Aug. 19, 1999, and claiming priority from U.K. (GB) application No. 9803351.7, filed Feb. 17, 1998. Each of the above-referenced applications, and each document cited in each of the above-referenced applications ("application cited documents"), and each document cited or referenced in each of the application cited documents, as well as all documents cited herein (in the following text, i.e., "herein cited documents") and all documents cited or referenced in herein cited documents, are hereby incorporated herein by reference.

FIELD OF THE INVENTION

The present invention relates to novel viral vectors capable of delivering anti-viral inhibitory RNA molecules to target cells.

BACKGROUND TO THE INVENTION

The application of gene therapy to the treatment of AIDS and HIV infection has been discussed widely (14). The types of therapeutic gene proposed usually fall into one of two broad categories. In the first the gene encodes protein products that inhibit the virus in a number of possible ways. One example of such a protein is the RevM10 derivative of the HIV Rev protein (16). The RevM10 protein acts as a transdominant negative mutant and so competitively inhibits Rev function in the virus. Like many of the protein-based strategies, the RevM10 protein is a derivative of a native HIV protein. While this provides the basis for the anti-HIV effect, it also has serious disadvantages. In particular, this type of strategy demands that in the absence of the virus there is little or no expression of the gene. Otherwise, healthy cells harbouring the gene become a target for the host cytotoxic T lymphocyte (CTL) system, which recognises the foreign protein (17, 25). The second broad category of therapeutic gene circumvents these CTL problems. The therapeutic gene encodes inhibitory RNA molecules; RNA is not a target for CTL recognition. The RNA molecules may be anti-sense RNA (15, 31), ribozymes (5) or competitive decoys (1).

Ribozymes are enzymatic RNA molecules which catalyse sequence-specific RNA processing. The design and structure of ribozymes has been described extensively in the literature in recent years (3, 7, 31). Amongst the most powerful systems are those that deliver multitarget ribozymes that cleave RNA of the target virus at multiple sites (5, 21).

In recent years a number of laboratories have developed retroviral vector systems based on HIV (2, 4, 18, 19, 22–24, 27, 32, 35, 39, 43). In the context of anti-HIV gene therapy these vectors have a number of advantages over the more conventional murine based vectors such as murine leukaemia virus (MLV) vectors. Firstly, HIV vectors would target precisely those cells that are susceptible to HIV infection (22, 23). Secondly, the HIV-based vector would transduce cells such as macrophages that are normally refractory to transduction by murine vectors (19, 20). Thirdly, the anti-HIV vector genome would be propagated through the CD4+ cell population by any virus (HIV) that escaped the therapeutic strategy (7). This is because the vector genome has the packaging signal that will be recognised by the viral particle packaging system. These various attributes make HIV-vectors a powerful tool in the field of anti-HIV gene therapy.

A combination of the multitarget ribozyme and an HIV-based vector would be attractive as a therapeutic strategy. However, until now this has not been possible. Vector particle production takes place in producer cells which express the packaging components of the particles and package the vector genome. The ribozymes that are designed to destroy the viral RNA would therefore also interrupt the expression of the components of the HIV-based vector system during vector production. The present invention aims to overcome this problem.

SUMMARY OF THE INVENTION

It is therefore an object of the invention to provide a system and method for producing viral particles, in particular HIV particles, which carry nucleotide constructs encoding inhibitory RNA molecules such as ribozymes and/or antisense RNAs directed against a corresponding virus, such as HIV, within a target cell, that overcomes the above-mentioned problems. The system includes both a viral genome encoding the inhibitory RNA molecules and nucleotide constructs encoding the components required for packaging the viral genome in a producer cell. However, in contrast to the prior art, although the packaging components have substantially the same amino acid sequence as the corresponding components of the target virus, the inhibitory RNA molecules do not affect production of the viral particles in the producer cells because the nucleotide sequence of the packaging components used in the viral system have been modified to prevent the inhibitory RNA molecules from effecting cleavage or degradation of the RNA transcripts produced from the constructs. Such a viral particle may be used to treat viral infections, in particular HIV infections.

Accordingly the present invention provides a viral vector system comprising:

(i) a first nucleotide sequence encoding a gene product capable of binding to and effecting the cleavage, directly or indirectly, of a second nucleotide sequence, or transcription product thereof, encoding a viral polypeptide required for the assembly of viral particles; and (ii) a third nucleotide sequence encoding said viral polypeptide required for the assembly of viral particles, which third nucleotide sequence has a different nucleotide sequence to the second nucleotide sequence such that the third nucleotide sequence, or transcription product thereof, is resistant to cleavage directed by said gene product.

In another aspect, the present invention provides a viral vector production system comprising:

(i) a viral genome comprising at least one first nucleotide sequence encoding a gene product capable of binding to and effecting the cleavage, directly or indirectly, of a second nucleotide sequence, or transcription product thereof, encoding a viral polypeptide required for the assembly of viral particles;

(ii) a third nucleotide sequence encoding said viral polypeptide required for the assembly of the viral genome into viral particles, which third nucleotide sequence has a different nucleotide sequence to the second nucleotide sequence such that said third nucleotide sequence, or transcription product thereof, is resistant to cleavage directed by said gene product.

The gene product is typically an RNA inhibitory sequence selected from a ribozyme and an anti-sense ribonucleic acid, preferably a ribozyme.

Preferably, the viral vector is a retroviral vector, more preferably a lentiviral vector, such as an HIV vector. The second nucleotide sequence and the third nucleotide sequences are typically from the same viral species, more preferably from the same viral strain. Generally, the viral genome is also from the same viral species, more preferably from the same viral strain.

In the case of retroviral vectors, the polypeptide required for the assembly of viral particles is selected from gag, pol and env proteins. Preferably at least the gag and pol sequences are lentiviral sequences, more preferably HIV sequences. Alternatively, or in addition, the env sequence is a lentiviral sequence, more preferably an HIV sequence.

In a preferred embodiment, the third nucleotide sequence is resistant to cleavage directed by the gene product as a result of one or more conservative alterations in the nucleotide sequence which remove cleavage sites recognised by the at least one gene product and/or binding sites for the at least one gene product. For example, where the gene product is a ribozyme, the third nucleotide sequence is adapted to be resistant to cleavage by the ribozyme.

Preferably the third nucleotide sequence is codon optimised for expression in host cells. The host cells, which term includes producer cells and packaging cells, are typically mammalian cells.

In a particularly preferred embodiment, (i) the viral genome is an HIV genome comprising nucleotide sequences encoding anti-HIV ribozymes and/or anti-HIV antisense sequences directed against HIV packaging component sequences (such as gag-pol) in a target HIV and (ii) the viral system for producing packaged HIV particles further comprises nucleotide constructs encoding the same packaging components (such as gag-pol proteins) as in the target HIV wherein the sequence of the nucleotide constructs is different from that found in the target HIV so that the anti-HIV ribozyme and/or antisense HIV sequences cannot effect cleavage or degradation of the gag-pol transcripts during production of the HIV particles in producer cells.

The present invention also provides a viral particle comprising a viral vector according to the present invention and one or more polypeptides encoded by the third nucleotide sequences according to the present invention. For example the present invention provides a viral particle produced using the viral vector production system of the invention.

In another aspect, the present invention provides a method for producing a viral particle which method comprises introducing into a host cell (i) a viral genome vector according to the present invention; (ii) one or more third nucleotide sequences according to the present invention; and (iii) nucleotide sequences encoding the other essential viral packaging components not encoded by the one or more third nucleotide sequences.

The present invention further provides a viral particle produced using by the method of the invention.

The present invention also provides a pharmaceutical composition comprising a viral particle according to the present invention together with a pharmaceutically acceptable carrier or diluent.

The viral system of the invention or viral particles of the invention may be used to treat viral infections, particularly retroviral infections such as lentiviral infections including HIV infections. Thus the present invention provides a method of treating a viral infection which method comprises administering to a human or animal patient suffering from the viral infection an effective amount of a viral system, viral particle or pharmaceutical composition of the present invention.

The invention relates in particular to HIV-based vectors carrying anti-HIV ribozymes. However, the invention can be applied to any other virus, in particular any other lentivirus, for which treatment by gene therapy may be desirable. The invention is illustrated herein for HIV, but this is not considered to limit the scope of the invention to HIV-based anti-HIV vectors.

It is a further object of the invention to provide a system for producing viral particles, in particular HIV particles, which do not require Rev/RRE for the production thereof. This system involves codon-optimising the gag-pol gene. Titre remains good and the system has the advantage that accessory proteins in the producer cell, and hence in the transduced cell, may be eliminated.

The HIV genome is AU-rich and this imparts a codon bias that is quite different from the one used by human genes. The codon usage is particularly marked in the case of the gag, pol and env genes. Interestingly, the expression of these genes is dependent on the presence of the Rev/RRE regulatory system, even in contexts other than the HIV genome. The Rev dependency has been explained in part by the presence of RNA instability sequences (INS) residing in these coding regions. The requirement for Rev also places a limitation on the development of HIV based vectors, because of the requirement to provide an accessory factor. We have now synthesised a complete codon optimised HIV-1 gag-pol gene. We show that expression levels are high and expression is Rev independent. This effect is due to an increase in the amount of gag-pol mRNA. Provision of the RRE in cis did not lower protein or RNA levels or stimulate a Rev response. Furthermore we have used this synthetic gag-pol gene to produce HIV vectors that now lack all of the accessory proteins.

Accordingly the present invention provides a nucleotide sequence coding for retroviral gag and pol proteins wherein the nucleotide sequence is codon optimised for expression in producer cells.

Preferably, the gag and pol proteins are lentiviral proteins, more preferably, they are HIV proteins. Typically, the producer cells are mammalian cells.

In a preferred embodiment, the nucleotide sequence is derived from a wild type sequence which has been codon optimised using the codon usage table of FIG. 4a. Preferably, the nucleotide sequence has the sequence as shown in SEQ. ID. No. 2 or the sequence from about nucleotide 1108 to about nucleotide 5414 as shown in SEQ. ID. No. 5.

In another aspect, the present invention provides a viral vector system comprising a nucleotide sequence of interest (NOI) and a nucleotide sequence according to the present invention encoding a viral polypeptide required for the assembly of viral particles.

In a further aspect, the present invention provides a viral production system comprising a viral genome comprising at least one nucleotide sequence of interest and a nucleotide sequence according to the present invention encoding a viral polypeptide required for the assembly of the viral genome into viral particles.

Preferably, the viral vector is a retroviral vector, more preferably, a lentiviral vector, such as a vector substantially derived from HIV-1.

In a preferred embodiment, the peptide required for assembly of viral particles also includes an envelope protein. Preferably, said envelope protein is encoded by a codon optimised env gene.

Typically, the NOI is selected from a therapeutic gene, a marker gene and a selection gene.

Preferably, the system according to the present invention is devoid of any functional accessory genes and may be used in a method of producing viral particles.

In another aspect, the present invention provides a method for producing a viral particle which method comprises introducing into a producer cell a viral genome according to the present invention, one or more nucleotide sequences according to the present invention, and nucleotide sequences encoding other essential viral packaging components not encoded by one or more of the above nucleotide sequences.

In another aspect, the invention provides a viral particle produced by a production system according to the invention, or by a method according to the invention.

In a further aspect, the present invention provides the use of a viral system according to the invention, or of a viral particle according to the invention, in treating a viral infection.

In another aspect, the present invention provides a pharmaceutical composition comprising a viral system or viral particle according to the invention, together with a pharmaceutically acceptable carrier or diluent.

DETAILED DESCRIPTION OF THE INVENTION

The term "viral vector" refers to a nucleotide construct comprising a viral genome capable of being transcribed in a host cell, which genome comprises sufficient viral genetic information to allow packaging of the viral RNA genome, in the presence of packaging components, into a viral particle capable of infecting a target cell. Infection of the target cell includes reverse transcription and integration into the target cell genome, where appropriate for particular viruses. The viral vector in use typically carries heterologous coding sequences (nucleotides of interest) which are to be delivered by the vector to the target cell, for example a first nucleotide sequence encoding a ribozyme. A viral vector is incapable of independent replication to produce infectious viral particles within the final target cell.

The term "viral vector system" is intended to mean a kit of parts which can be used when combined with other necessary components for viral particle production to produce viral particles in host cells. For example, the first nucleotide sequence may typically be present in a plasmid vector construct suitable for cloning the first nucleotide sequence into a viral genome vector construct. When combined in a kit with a third nucleotide sequence, which will also typically be present in a separate plasmid vector construct, the resulting combination of plasmid containing the first nucleotide sequence and plasmid containing the third nucleotide sequence comprises the essential elements of the invention. Such a kit may then be used by the skilled person in the production of suitable viral vector genome constructs which when transfected into a host cell together with the plasmid containing the third nucleotide sequence, and optionally nucleic acid constructs encoding other components required for viral assembly, will lead to the production of infectious viral particles.

Alternatively, the third nucleotide sequence may be stably present within a packaging cell line that is included in the kit.

The kit may include the other components needed to produce viral particles, such as host cells and other plasmids encoding essential viral polypeptides required for viral assembly. By way of example, the kit may contain (i) a plasmid containing a first nucleotide sequence encoding an anti-HIV ribozyme and (ii) a plasmid containing a third nucleotide sequence encoding a modified HIV gag-pol construct which cannot be cleaved by the anti-HIV ribozyme. Optional components would then be (a) an HIV viral genome construct with suitable restriction enzyme recognition sites for cloning the first nucleotide sequence into the viral genome; (b) a plasmid encoding a VSV-G env protein. Alternatively, nucleotide sequence encoding viral polypeptides required for assembly of viral particles may be provided in the kit as packaging cell lines comprising the nucleotide sequences, for example a VSV-G expressing cell line.

The term "viral vector production system" refers to the viral vector system described above wherein the first nucleotide sequence has already been inserted into a suitable viral vector genome.

Viral vectors are typically retroviral vectors, in particular lentiviral vectors such as HIV vectors. The retroviral vector of the present invention may be derived from or may be derivable from any suitable retrovirus. A large number of different retroviruses have been identified. Examples include: murine leukemia virus (MLV), human immunodeficiency virus (HIV), simian immunodeficiency virus, human T-cell leukemia virus (HTLV). equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV). A detailed list of retroviruses may be found in Coffin et al., 1997, "Retroviruses", Cold Spring Harbour Laboratory Press Eds: J M Coffin, S M Hughes, H E Varmus pp 758–763.

Details on the genomic structure of some retroviruses may be found in the art. By way of example, details on HIV and Mo-MLV may be found from the NCBI Genbank (Genome Accession Nos. AF033819 and AF033811, respectively).

The lentivirus group can be split even further into "primate" and "non-primate". Examples of primate lentiviruses include human immunodeficiency virus (HIV), the causative agent of human auto-immunodeficiency syndrome (AIDS), and simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

The basic structure of a retrovirus genome is a 5' LTR and a 3' LTR, between or within which are located a packaging signal to enable the genome to be packaged, a primer binding site, integration sites to enable integration into a host cell genome and gag, pol and env genes encoding the packaging components—these are polypeptides required for the assembly of viral particles. More complex retroviruses have additional features, such as rev and RRE sequences in HIV, which enable the efficient export of RNA transcripts of the integrated provirus from the nucleus to the cytoplasm of an infected target cell.

In the provirus, these genes are flanked at both ends by regions called long terminal repeats (LTRs). The LTRs are responsible for proviral integration, and transcription. LTRs also serve as enhancer-promoter sequences and can control the expression of the viral genes. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

In a defective retroviral vector genome gag, pol and env may be absent or not functional. The R regions at both ends of the RNA are repeated sequences. U5 and U3 represent unique sequences at the 5' and 3' ends of the RNA genome respectively.

In a typical retroviral vector for use in gene therapy, at least part of one or more of the gag, pol and env protein coding regions essential for replication may be removed from the virus. This makes the retroviral vector replication-defective. The removed portions may even be replaced by a nucleotide sequence of interest (NOI), such as a first nucleotide sequence of the invention, to generate a virus capable of integrating its genome into a host genome but wherein the modified viral genome is unable to propagate itself due to a lack of structural proteins. When integrated in the host genome, expression of the NOI occurs—resulting in, for example, a therapeutic and/or a diagnostic effect. Thus, the transfer of an NOI into a site of interest is typically achieved by: integrating the NOI into the recombinant viral vector; packaging the modified viral vector into a virion coat; and allowing transduction of a site of interest—such as a targeted cell or a targeted cell population.

A minimal retroviral genome for use in the present invention will therefore comprise (5') R-U5—one or more first nucleotide sequences—U3-R (3'). However, the plasmid vector used to produce the retroviral genome within a host cell/packaging cell will also include transcriptional regulatory control sequences operably linked to the retroviral genome to direct transcription of the genome in a host cell/packaging cell. These regulatory sequences may be the natural sequences associated with the transcribed retroviral sequence, i.e. the 5' U3 region, or they may be a heterologous promoter such as another viral promoter, for example the CMV promoter.

Some retroviral genomes require additional sequences for efficient virus production. For example, in the case of HIV, rev and RRE sequence are preferably included. However the requirement for rev and RRE can be reduced or eliminated by codon optimisation.

Once the retroviral vector genome is integrated into the genome of its target cell as proviral DNA, the ribozyme sequences need to be expressed. In a retrovirus, the promoter is located in the 5' LTR U3 region of the provirus. In retroviral vectors, the promoter driving expression of a therapeutic gene may be the native retroviral promoter in the 5' U3 region, or an alternative promoter engineered into the vector. The alternative promoter may physically replace the 5' U3 promoter native to the retrovirus, or it may be incorporated at a different place within the vector genome such as between the LTRs.

Thus, the first nucleotide sequence will also be operably linked to a transcriptional regulatory control sequence to allow transcription of the first nucleotide sequence to occur in the target cell. The control sequence will typically be active in mammalian cells. The control sequence may, for example, be a viral promoter such as the natural viral promoter or a CMV promoter or it may be a mammalian promoter. It is particularly preferred to use a promoter that is preferentially active in a particular cell type or tissue type in which the virus to be treated primarily infects. Thus, in one embodiment, a tissue-specific regulatory sequences may be used. The regulatory control sequences driving expression of the one or more first nucleotide sequences may be constitutive or regulated promoters.

Replication-defective retroviral vectors are typically propagated, for example to prepare suitable titres of the retroviral vector for subsequent transduction, by using a combination of a packaging or helper cell line and the recombinant vector. That is to say, that the three packaging proteins can be provided in trans.

A "packaging cell line" contains one or more of the retroviral gag, pol and env genes. The packaging cell line produces the proteins required for packaging retroviral DNA but it cannot bring about encapsidation due to the lack of a psi region. However, when a recombinant vector carrying an NOI and a psi region is introduced into the packaging cell line, the helper proteins can package the psi-positive recombinant vector to produce the recombinant virus stock. This virus stock can be used to transduce cells to introduce the NOI into the genome of the target cells. It is preferred to use a psi packaging signal, called psi plus, that contains additional sequences spanning from upstream of the splice donor to downstream of the gag start codon (Bender et al. (46)) since this has been shown to increase viral titres.

The recombinant virus whose genome lacks all genes required to make viral proteins can transduce only once and cannot propagate. These viral vectors which are only capable of a single round of transduction of target cells are known as replication defective vectors. Hence, the NOI is introduced into the host/target cell genome without the generation of potentially harmful retrovirus. A summary of the available packaging lines is presented in Coffin et al., 1997 (ibid).

Retroviral packaging cell lines in which the gag, pol and env viral coding regions are carried on separate expression plasmids that are independently transfected into a packaging cell line are preferably used. This strategy, sometimes referred to as the three plasmid transfection method (Soneoka et al. (33)), reduces the potential for production of a replication-competent virus since three recombinant events are required for wild type viral production. As recombination is greatly facilitated by homology, reducing or eliminating homology between the genomes of the vector and the helper can also be used to reduce the problem of replication-competent helper virus production.

An alternative to stably transfected packaging cell lines is to use transiently transfected cell lines. Transient transfections may advantageously be used to measure levels of vector production when vectors are being developed. In this regard, transient transfection avoids the longer time required to generate stable vector-producing cell lines and may also be used if the vector or retroviral packaging components are toxic to cells. Components typically used to generate retroviral vectors include a plasmid encoding the gag and pol proteins, a plasmid encoding the env protein and a plasmid containing an NOI. Vector production involves transient transfection of one or more of these components into cells containing the other required components. If the vector encodes toxic genes or genes that interfere with the replication of the host cell, such as inhibitors of the cell cycle or genes that induce apoptosis, it may be difficult to generate stable vector-producing cell lines, but transient transfection can be used to produce the vector before the cells die. Also, cell lines have been developed using transient transfection that produce vector titre levels that are comparable to the levels obtained from stable vector-producing cell lines (Pear et al. (47)).

Producer cells/packaging cells can be of any suitable cell type. Most commonly, mammalian producer cells are used but other cells, such as insect cells are not excluded. Clearly, the producer cells will need to be capable of efficiently translating the env and gag, pol mRNA. Many suitable producer/packaging cell lines are known in the art. The skilled person is also capable of making suitable packaging cell lines by, for example stably introducing a nucleotide construct encoding a packaging component into a cell line.

As will be discussed below, where the retroviral genome encodes an inhibitory RNA molecule capable of effecting the cleavage of gag, pol and/or env RNA transcripts, the nucleotide sequences present in the packaging cell line, either integrated or carried on plasmids, or in the transiently transfected producer cell line, which encode gag, pol and or env proteins will be modified so as to reduce or prevent binding of the inhibitory RNA molecule(s). In this way, the inhibitory RNA molecule(s) will not prevent expression of components in packaging cell lines that are essential for packaging of viral particles.

It is highly desirable to use high-titre virus preparations in both experimental and practical applications. Techniques for increasing viral titre include using a psi plus packaging signal as discussed above and concentration of viral stocks. In addition, the use of different envelope proteins, such as the G protein from vesicular-stomatitis virus has improved titres following concentration to $10^9$ per ml (Cosset et al. (48)). However, typically the envelope protein will be chosen such that the viral particle will preferentially infect cells that are infected with the virus which it desired to treat. For example where an HIV vector is being used to treat HIV infection, the env protein used will be the HIV env protein.

Suitable first nucleotide sequences for use according to the present invention encode gene products that result in the cleavage and/or enzymatic degradation of a target nucleotide sequence, which will generally be a ribonucleotide. As particular examples, ribozymes, and antisense sequences may be mentioned.

Ribozymes are RNA enzymes which cleave RNA at specific sites. Ribozymes can be engineered so as to be specific for any chosen sequence containing a ribozyme cleavage site. Thus, ribozymes can be engineered which have chosen recognition sites in transcribed viral sequences. By way of an example, ribozymes encoded by the first nucleotide sequence recognise and cleave essential elements of viral genomes required for the production of viral particles, such as packaging components. Thus, for retroviral genomes, such essential elements include the gag, pol and env gene products. A suitable ribozyme capable of recognising at least one of the gag, pol and env gene sequences, or more typically, the RNA sequences transcribed from these genes, is able to bind to and cleave such a sequence. This will reduce or prevent production of the gal, pol or env protein as appropriate and thus reduce or prevent the production of retroviral particles.

Ribozymes come in several forms, including hammerhead, hairpin and hepatitis delta antigenomic ribozymes. Preferred for use herein are hammerhead ribozymes, in part because of their relatively small size, because the sequence requirements for their target cleavage site are minimal and because they have been well characterised. The ribozymes most commonly used in research at present are hammerhead and hairpin ribozymes.

Each individual ribozyme has a motif which recognises and binds to a recognition site in the target RNA. This motif takes the form of one or more "binding arms", generally two binding arms. The binding arms in hammerhead ribozymes are the flanking sequences Helix I and Helix III, which flank Helix II. These can be of variable length, usually between 6 to 10 nucleotides each, but can be shorter or longer. The length of the flanking sequences can affect the rate of cleavage. For example, it has been found that reducing the total number of nucleotides in the flanking sequences from 20 to 12 can increase the turnover rate of the ribozyme cleaving a HIV sequence, by 10-fold (44). A catalytic motif in the ribozyme Helix II in hammerhead ribozymes cleaves the target RNA at a site which is referred to as the cleavage site. Whether or not a ribozyme will cleave any given RNA is determined by the presence or absence of a recognition site for the ribozyme containing an appropriate cleavage site.

SEQ ID Nos. 6–22 are assigned as follows:
SEQ ID NO: 6 refers to the ribozyme hammerhead helix II sequence
SEQ ID NO: 7 refers to the. sequence of the cleavage site of GAG 1
SEQ ID NO: 8 refers to the sequence of the cleavage site of GAG 2
SEQ ID NO: 9 refers to the sequence of the cleavage site of GAG 3
SEQ ID NO: 10 refers to the sequence of the cleavage site of GAG 4
SEQ ID NO: 11 refers to the sequence of the cleavage site of POL 1
SEQ ID NO: 12 refers to the sequence of the cleavage site of POL 2
SEQ ID NO: 13 refers to the sequence of the cleavage site of POL 3
SEQ ID NO: 14 refers to the sequence of the cleavage site of POL 4
SEQ ID NO: 15 refers to the sequence of the cleavage site of POL 5
SEQ ID NO: 16 refers to the sequence of the cleavage site of POL 6
SEQ ID NO: 17 refers to the sequence of the cleavage site of POL 7
SEQ ID NO: 18 refers to the sequence of the cleavage site of POL 8
SEQ ID NO: 19 refers to the sequence of the cleavage site of POL 9
SEQ ID NO: 20 refers to the sequence of the primer RIB1
SEQ ID NO: 21 refers to the sequence of the primer RIB2
SEQ ID NO: 22 refers to the sequence of the primer RIB3.

Each type of ribozyme recognises its own cleavage site. The hammerhead ribozyme cleavage site has the nucleotide base triplet GUX directly upstream where G is guanine, U is uracil and X is any nucleotide base. Hairpin ribozymes have a cleavage site of BCUGNYR, where B is any nucleotide base other than adenine, N is any nucleotide, Y is cytosine or thymine and R is guanine or adenine. Cleavage by hairpin ribozymes takes places between the G and the N in the cleavage site.

The nucleic acid sequences encoding the packaging components (the "third nucleotide sequences") may be resistant to the ribozyme or ribozymes because they lack any cleavage sites for the ribozyme or ribozymes. This prohibits enzymatic activity by the ribozyme or ribozymes and therefore there is no effective recognition site for the ribozyme or ribozymes. Alternatively or additionally, the potential recognition sites may be altered in the flanking sequences which form the part of the recognition site to which the ribozyme binds. This either eliminates binding of the ribozyme motif to the recognition site, or reduces binding capability enough to destabilise any ribozyme-target complex and thus reduce the specificity and catalytic activity of the ribozyme. Where the flanking sequences only are altered, they are preferably altered such that catalytic activity of the ribozyme at the altered target sequence is negligible and is effectively eliminated.

Preferably, a series of several anti-HIV ribozymes is employed in the invention (5, 7, 10, 13, 21, 36, 38, 40). These can be any anti-HIV ribozymes but must include one or more which cleave the RNA that is required for the expression of gag, pol or env. Preferably, a plurality of ribozymes is employed, together capable of cleaving gag, pol and env RNA of the native retrovirus at a plurality of sites. Since HIV exists as a population of quasispecies, not all of the target sequences for the ribozymes will be included in all HIV variants. The problem presented by this variability can be overcome by using multiple ribozymes. Multiple ribozymes can be included in series in a single vector and can function independently when expressed as a single RNA sequence. A single RNA containing two or more ribozymes having different target recognition sites may be referred to as a multitarget ribozyme. The placement of ribozymes in series has been demonstrated to enhance cleavage. The use of a plurality of ribozymes is not limited to treating HIV infection but may be used in relation to other viruses, retroviruses or otherwise.

Antisense technology is well known on the art. There are various mechanisms by which antisense sequences are believed to inhibit gene expression. One mechanism by which antisense sequences are believed to function is the recruitment of the cellular protein RNAseH to the target sequence/antisense construct heteroduplex which results in cleavage and degradation of the heteroduplex. Thus the antisense construct, by contrast to ribozymes, can be said to lead indirectly to cleavage/degradation of the target sequence. Thus according to the present invention, a first nucleotide sequence may encode an antisense RNA that binds to either a gene encoding an essential/packaging component or the RNA transcribed from said gene such that expression of the gene is inhibited, for example as a result of RNAseH degradation of a resulting heteroduplex. It is not necessary for the antisense construct to encode the entire complementary sequence of the gene encoding an essential/packaging component—a portion may suffice. The skilled person will easily be able to determine how to design a suitable antisense construct.

By contrast, the nucleic acid sequences encoding the essential/packaging components of the viral particles required for the assembly of viral particles in the host cells/producer cells/packaging cells (the third nucleotide sequences) are resistant to the inhibitory RNA molecules encoded by the first nucleotide sequence. For example in the case of ribozymes, resistance is typically by virtue of alterations in the sequences which eliminate the ribozyme recognition sites. At the same time, the amino acid coding sequence for the essential/packaging components is retained so that the viral components encoded by the sequences remain the same, or at least sufficiently similar that the function of the essential/packaging components is not compromised.

The term "viral polypeptide required for the assembly of viral particles" means a polypeptide normally encoded by the viral genome to be packaged into viral particles, in the absence of which the viral genome cannot be packaged. For example, in the context of retroviruses such polypeptides would include gag, pol and env. The terms "packaging component" and "essential component" are also included within this definition.

In the case of antisense sequences, the third nucleotide sequence differs from the second nucleotide sequence encoding the target viral packaging component antisense sequence to the extent that although the antisense sequence can bind to the second nucleotide sequence, or transcript thereof, the antisense sequence can not bind effectively to the third nucleotide sequence or RNA transcribed from therefrom. The changes between the second and third nucleotide sequences will typically be conservative changes, although a small number of amino acid changes may be tolerated provided that, as described above, the function of the essential/packaging components is not significantly impaired.

Preferably, in addition to eliminating the ribozyme recognition sites, the alterations to the coding sequences for the viral components improve the sequences for codon usage in the mammalian cells or other cells which are to act as the producer cells for retroviral vector particle production. This improvement in codon usage is referred to as "codon optimisation". Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Thus preferably, the sequences encoding the packaging components are codon optimised. More preferably, the sequences are codon optimised in their entirety. Following codon optimisation, it is found that there are numerous sites in the wild type gag, pol and env sequences which can serve as ribozyme recognition sites and which are no longer present in the sequences encoding the packaging components. In an alternative but less practical strategy, the sequences encoding the packaging components can be altered by targeted conservative alterations so as to render them resistant to selected ribozymes capable of cleaving the wild type sequences.

An additional advantage of codon optimising HIV packaging components is that this can increase gene expression. In particular, it can render gag-pol expression Rev independent.

In order to enable the use of anti-rev or RRE factors in the retroviral vector, however, it would be necessary to render the viral vector generation system totally Rev/RRE independent (58). Thus, the genome also needs to be modified. This is achieved by optimising the HIV-1 based vector genome components in addition to gag-pol. Advantageously, these modifications also lead to the production of a safer system absent of all accessory proteins both in the producer and in the transduced cell.

The gag-pol gene comprises two overlapping reading frames encoding gag and pol proteins respectively. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the gag-pol gene. The region of overlap extends from nucleotide 1222 downstream of the beginning of gag (wherein nucleotide 1 is the A of the gag ATG) to the end of gag (nt 1503). Consequently, a 281 bp fragment spanning the frameshift site and the overlapping region of the two reading frames is preferably not codon optimised. Retaining this fragment will enable more efficient expression of the gag-pol polyprotein.

As described above, the packaging components for a retroviral vector include expression products of gag, pol and env genes. In addition, efficient packaging depends on a short sequence of 4 stem loops followed by a partial sequence from gag and env (the "packaging signal"). Thus, inclusion of a deleted gag sequence in the retroviral vector genome (in addition to the full gag sequence on the packaging construct) will optimise vector titre. To date efficient packaging has been reported to require from 255 to 360 nucleotides of gag in vectors that still retain env sequences, or about 40 nucleotides of gag in a particular combination of splice donor mutation, gag and env deletions. We have surprisingly found that a deletion of up to 360 nucleotides in gag leads to an increase in vector titre. Further deletions resulted in lower titres. Additional mutations at the major splice donor site upstream of gag were found to disrupt packaging signal secondary structure and therefore lead to decreased vector titre. Thus, preferably, the retroviral vector genome includes a gag sequence from which up to 360 nucleotides have been removed.

In accordance with the present invention, gag and pol employed in the packaging system are derived from the target retrovirus on which the vector genome is based. Thus, in the RNA transcript form, gag and pol would normally be cleavable by the ribozymes present in the vector genome. The env gene employed in the packaging system may be derived from a different virus, including other retroviruses such as MLV and non-retroviruses such as VSV (a Rhabdovirus), in which case it may not need any sequence alteration to render it resistant to ribozyme cleavage. Alternatively, env may be derived from the same retrovirus as gag and pol, in which case any recognition sites for the ribozymes will need to be eliminated by sequence alteration.

The process of producing a retroviral vector in which the envelope protein is not the native envelope of the retrovirus is known as "pseudotyping". Certain envelope proteins, such as MLV envelope protein and vesicular stomatitis virus G (VSV-G) protein, pseudotype retroviruses very well. Pseudotyping can be useful for altering the target cell range of the retrovirus. Alternatively, to maintain target cell specificity for target cells infected with the particular virus it is desired to treat, the envelope protein may be the same as that of the target virus, for example HIV.

Other therapeutic coding sequences may be present along with the first nucleotide sequence or sequences. Other therapeutic coding sequences include, but are not limited to, sequences encoding cytokines, hormones, antibodies, immunoglobulin fusion proteins, enzymes, immune co-stimulatory molecules, anti-sense RNA, a transdominant negative mutant of a target protein, a toxin, a conditional toxin, an antigen, a single chain antibody, tumour suppresser protein and growth factors. When included, such coding sequences are operatively linked to a suitable promoter, which may be the promoter driving expression of the first nucleotide sequence or a different promoter or promoters.

Thus the invention comprises two components. The first is a genome construction that will be packaged by viral packaging components and which carries a series of anti-viral inhibitory RNA molecules such as anti-HIV ribozymes (5, 7, 10, 13, 21, 36, 38, 40). These could be any anti-HIV ribozymes but the key issue for this invention is that some of them cleave RNA that is required for the expression of native or wild type HIV gag, pol or env coding sequences. The second component is the packaging system which comprises a cassette for the expression of HIV gag, pol and a cassette either for HIV env or an envelope gene encoding a pseudotyping envelope protein—the packaging system being resistant to the inhibitory RNA molecules.

The viral particles of the present invention, and the viral vector system and methods used to produce may thus be used to treat or prevent viral infections, preferably retroviral infections, in particular lentiviral, especially HIV, infections. Specifically, the viral particles of the invention, typically produced using the viral vector system of the present invention may be used to deliver inhibitory RNA molecules to a human or animal in need of treatment for a viral infection.

Alternatively, or in addition, the viral production system may be used to transfect cells obtained from a patient ex vivo and then returned to the patient. Patient cells transfected ex vivo may be formulated as a pharmaceutical composition (see below) prior to readminstration to the patient.

Preferably the viral particles are combined with a pharmaceutically acceptable carrier or diluent to produce a pharmaceutical composition. Thus, the present invention also provides a pharmaceutical composition for treating an individual, wherein the composition comprises a therapeutically effective amount of the viral particle of the present invention, together with a pharmaceutically acceptable carrier, diluent, excipient or adjuvant. The pharmaceutical composition may be, for human or animal usage.

The choice of pharmaceutical carrier, excipient or diluent can be selected with regard to the intended route of administration and standard pharmaceutical practice. Suitable carriers and diluents include isotonic saline solutions, for example phosphate-buffered saline. The pharmaceutical compositions may comprise as—or in addition to—the carrier, excipient or diluent any suitable binder(s), lubricant (s), suspending agent(s), coating agent(s), solubilising agent (s), and other carrier agents that may aid or increase the viral entry into the target site (such as for example a lipid delivery system).

The pharmaceutical composition may be formulated for parenteral, intramuscular, intravenous, intracranial, subcutaneous, intraocular or transdermal administration.

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The amount of virus administered is typically in the range of from $10^3$ to $10^{10}$ pfu, preferably from $10^5$ to $10^8$ pfu, more preferably from $10^6$ to $10^7$ pfu. When injected, typically 1–10 $\mu$l of virus in a pharmaceutically acceptable suitable carrier or diluent is administered.

When the polynucleotide/vector is administered as a naked nucleic acid, the amount of nucleic acid administered is typically in the range of from 1 $\mu$g to 10 mg, preferably from 100 $\mu$g to 1 mg.

Where the first nucleotide sequence (or other therapeutic sequence) is under the control of an inducible regulatory sequence, it may only be necessary to induce gene expression for the duration of the treatment. Once the condition has been treated, the inducer is removed and expression of the NOI is stopped. This will clearly have clinical advantages. Such a system may, for example, involve administering the antibiotic tetracycline, to activate gene expression via its effect on the tet repressor/VP16 fusion protein.

The invention will now be further described by way of Examples, which are meant to serve to assist one of ordinary skill in the art in carrying out the invention and are not intended in any way to limit the scope of the invention. The Examples refer to the Figures. In the Figures:

FIG. 3 shows the codon usage table for wild type HIV gag-pol of strain HXB2 (accession number: K03455).

FIG. 4 shows the codon usage table of the codon optimised sequence designated gagpol-SYNgp. FIG. 4a shows a comparative codon usage table.

FIG. 5 shows the codon usage table of the wild type HIV env called env-mn.

FIG. 6 shows the codon usage table of the codon optimised sequence of HIV env designated SYNgp160 mn.

FIG. 7 shows three plasmid constructs for use in the invention.

FIG. 9 shows a sequence comparison between the wild type HIV gag-pol sequence (pGP-RRE3) and the codon optimised gag-pol sequence (pSYNGP).

FIG. 14 shows the plasmids used to study the effect of HIV-1 gag on the codon optimised gene.

FIG. 18 shows transduction efficiency at MOI 1.

FIG. 21 shows vector titres generated with different gag-pol constructs.

FIG. 22 shows vector titres from the Rev/RRE (−) and (+) genomes.

FIG. 23 shows vector titres from the pHS series of vector genomes.

FIG. 24 shows vector titres for the pHS series of vector genomes in the presence or absence of Rev/RRE.

In more detail, FIG. 9 shows a sequence comparison between the wild type HIV gag-pol sequence (pGP-RRE3) and the codon optimised gag-pol sequence (pSYNGP) wherein the upper sequence represents pSYNGP and the lower sequence represents pGP-RRE3.

Figures 9H, 10:
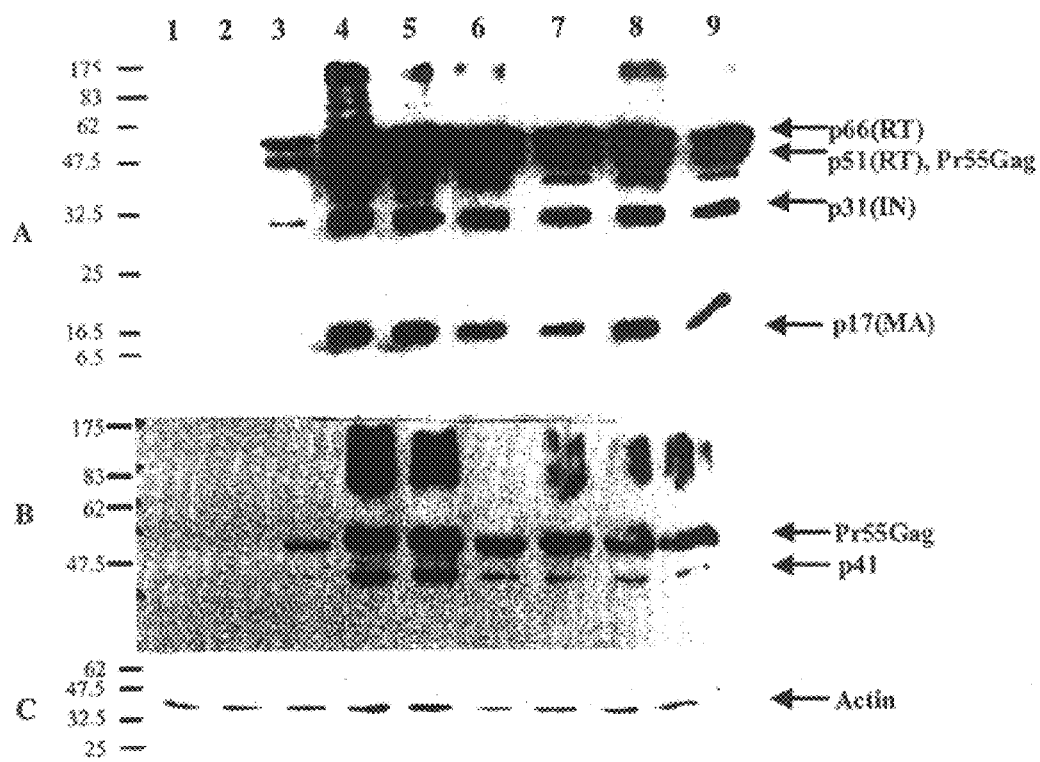
FIG. 10 shows Rev independence of protein expression particle formation.

FIG. 10 shows Rev independence of protein expression particle formation. 5 μg of the gag-pol expression plasmids were transfected into 293T cells in the presence or absence of Rev (pCMV-Rev, 1 μg) and protein levels were determined 48 hours post transfection in culture supernatants (A) and cell lysates (B). HIV-1 positive human serum was used to detect the gag-pol proteins. The blots were re-probed with an anti-actin antibody, as an internal control (C). The protein marker (New England Biolabs) sizes (in kDa) are shown on the side of the gel. Lanes: 1. Mock transfected 293T cells, 2. pGP-RRE3, 3. pGP-RRE3+pCMV-Rev, 4. pSYNGP, 5. pSYNGP+pCMV-Rev, 6. pSYNGP-RRE, 7. pSYNGP-RRE+pCMV-Rev, 8. pSYNGP-ERR, 9. pSYNGP-ERR+pCMV-Rev.

Figure 11:
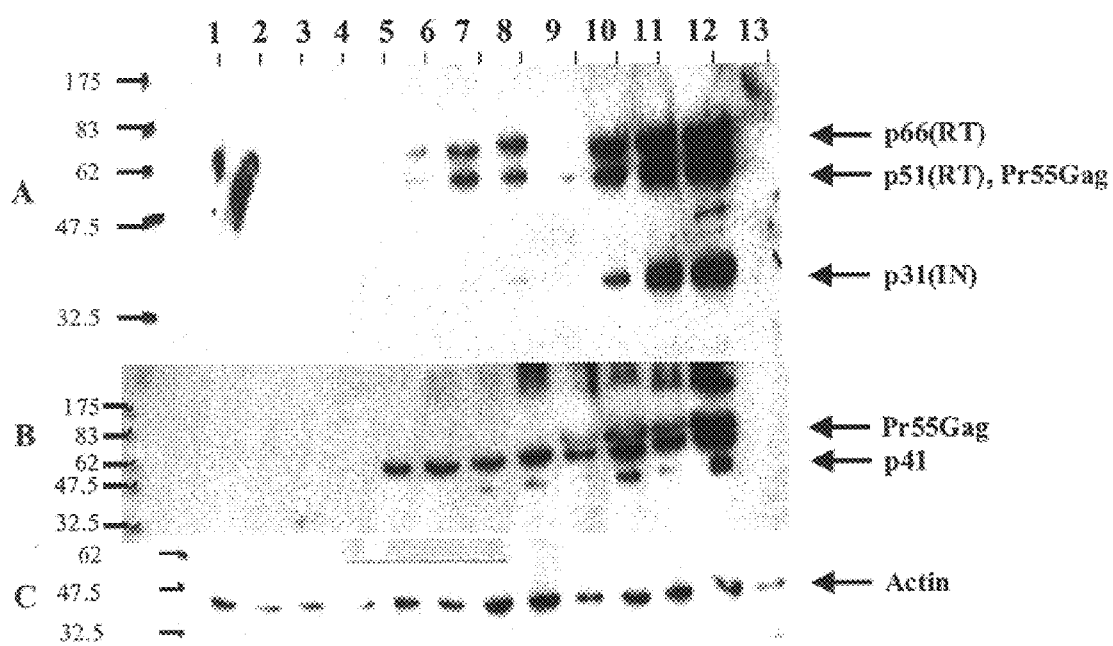
FIG. 11 shows translation rates of WT and codon optimised gag-pol.

FIG. 11 shows translation rates of WT and codon optimised gag-pol. 293T cells were transfected with 2 μg pGP-RRE3 (+/−1 μg pCMV-Rev) or 2 μg pSYNGP. Protein samples from culture supernatants (A) and cell extracts (B) were analysed by Western blotting 12, 25, 37 and 48 hours post-transfection. HIV-1 positive human serum was used to detect gag-pol proteins (A, B) and an anti-actin antibody was used as an internal control (C). The protein marker sizes are shown on the side of the gel (in kD). A Phosphorimager was used for quantification of the results. Lanes: 1. pGP-RRE3 12 h, 2. pGP-RRE3 25 h, 3. pGP-RRE3 37 h, 4. pGP-RRE3 48 h, 5. pGP-RRE3+pCMV-Rev 12 h, 6. pGP-RRE3+pCMV-Rev 25 h, 7. pGP-RRE3+pCMV-Rev 37 h, 8. pGP-RRE3+pCMV-Rev 48 h, 9. pSYNGP 12 h, 10. pSYNGP 25 h, 11. pSYNGP 37 h, 12. pSYNGP 48 h, 13. Mock transfected 293T cells.

Figure 12:
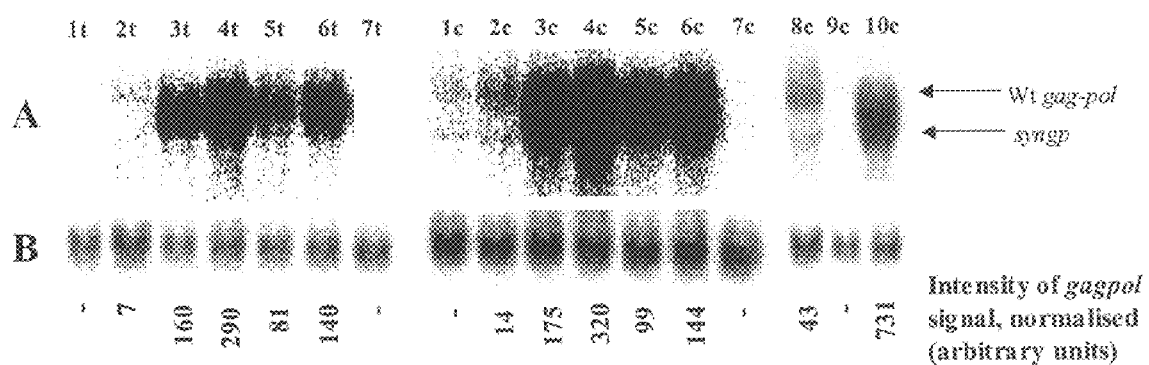
FIG. 12 shows gag-pol mRNA levels in total and cytoplasmic fractions.

FIG. 12 shows gag-pol mRNA levels in total and cytoplasmic fractions. Total and cytoplasmic RNA was extracted from 293T cells 36 hours after transfection with 5 μg of the gag-pol expression plasmid (+/−1 μg pCMV-Rev) and mRNA levels were estimated by Northern blot analysis. A probe complementary to nt 1222–1503 of both the wild type and codon optimised gene was used. Panel A shows the band corresponding to the HIV-1 gag-pol. The sizes of the mRNAs are 4.4 kb for the codon optimised and 6 kb for the wild type gene. Panel B shows the band corresponding to human ubiquitin (internal control for normalisation of results). Quantification was performed using a Phosphorimager. Lane numbering: c indicates cytoplasmic fraction and t indicates total RNA fraction. Lanes: 1. pGP-RRE3, 2. pGP-RRE3+pCMV-Rev, 3. pSYNGP, 4. pSYNGP+pCMV-Rev, 5. pSYNGP-RRE, 6. pSYNGP-RRE+pCMV-Rev, 7. Mock transfected 293T cells, 8. pGP-RRE3+pCMV-Rev, 19. Mock transfected 293T cells, 10. pSYNGP.

Figure 13:
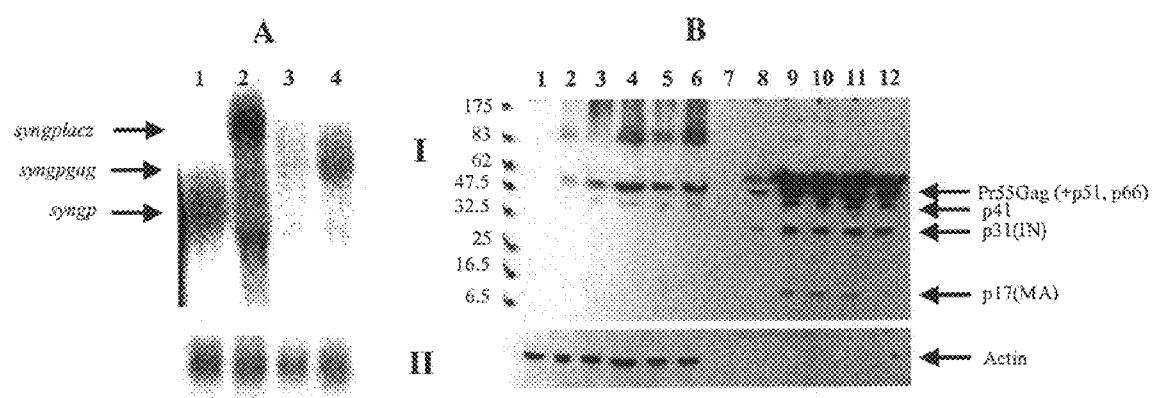
FIG. 13 shows the effect of insertion of WT gag downstream of the codon optimised gene on RNA and protein levels.

FIG. 13 shows the effect of insertion of WT gag downstream of the codon optimised gene on RNA and protein levels. The wt gag sequence was inserted downstream of the codon optimised gene in both orientations (NotI site), resulting in plasmids pSYN6 (correct orientation, see FIG. 6) and pSYN7 (reverse orientation, see FIG. 6). The gene encoding for β-galactosidase (LacZ) was also inserted in the same site and the correct orientation (plasmid pSYN8, see FIG. 6). 293T cells were transfected with 5 μg of each plasmid and 48 hours post transfection mRNA and protein levels were determined as previously described by means of Northern and Western blot analysis respectively.

A. Northern blot analysis in cytoplasmic RNA fractions. The blot was probed with a probe complementary to nt 1510–2290 of the codon optimised gene (I) and was re-probed with a probe specific for human ubiquitin (II). Lanes: 1. pSYNGP, 2. pSYN8, 3. pSYN7, 4. pSYN6

B. Western blot analysis: HIV-1 positive human serum was used to detect the gag-pol proteins (I) and an anti-actin antibody was used as an internal control (II). Lanes: Cell lysates: 1. Mock transfected 293T cells, 2. pGP-RRE3+pCMV-Rev, 3. pSYNGP, 4. pSYN6, 5. pSYN7, 6. pSYN8. Supernatants: 7. Mock transfected 293T cells, 8. pGP-RRE3+pCMV-Rev, 9. pSYNGP, 10. pSYN6, 11. pSYN7, 12. pSYN8. The protein marker (New England Biolabs) sizes are shown on the side of the gel.

FIG. 14 shows the plasmids used to study the effect of HIV-1 gag on the codon optimised gene. The backbone for all constructs was pCI-Neo. Syn gp: The codon optimised HIV-1 gag-pol gene. HXB2 gag: The wild type HIV-1 gag gene. HXB2 gag,r: The wild type HIV-1 gag gene in the reverse orientation. HXB2 gagΔATG: The wild type HIV-1 gag gene without the gag ATG. HXB2 gag-fr.sh.: The wild type HIV-1 gag gene with a frameshift mutation. HXB2 gag 625–1503: Nucleotides 625–1503 of the wild type HIV-1 gag gene. HXB2 gag 1–625: Nucleotides 1–625 of the wild type HIV-1 gag gene.

Figure 15:
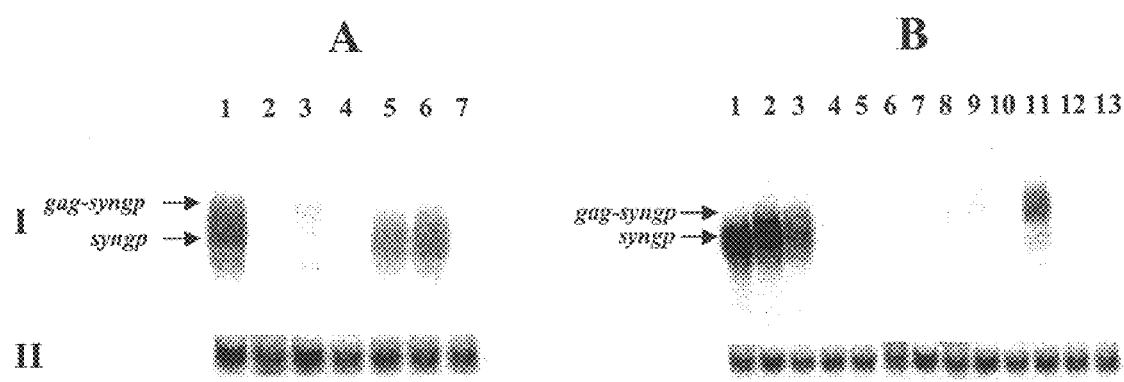
FIG. 15 shows the effect on cytoplasmic RNA of insertion of HIV-1 gag upstream of the codon optimised gene.

FIG. 15 shows the effect on cytoplasmic RNA of insertion of HIV-1 gag upstream of the codon optimised gene. Cytoplasmic RNA was extracted 48 hours post transfection of 293T cells (5 µg of each pSYN plasmid was used and 1 µg of pCMV-Rev was co-transfected in some cases). The probe that was used was designed to be complementary to nt 1510–2290 of the codon optimised gene (I). A probe specific for human ubiquitin was used as an internal control (II).
A. Lanes: 1. pSYNGP, 2. pSYN9, 3. pSYN10, 4. pSYN10+pCMV-Rev, 5. pSYN11, 6. pSYN11+pCMV-Rev, 7. pCMV-Rev.
B. Lanes: 1. pSYNGP, 2. pSYNGP-RRE, 3. pSYNGP-RRE+pCMV-Rev, 4. pSYN12, 5. pSYN14, 6. pSYN14+pCMV-Rev, 7. pSYN13, 8. pSYN15, 9. pSYN17, 10. pGP-RRE3, 11. pSYN6, 12. pSYN9, 13. pCMV-Rev.

Figure 16:
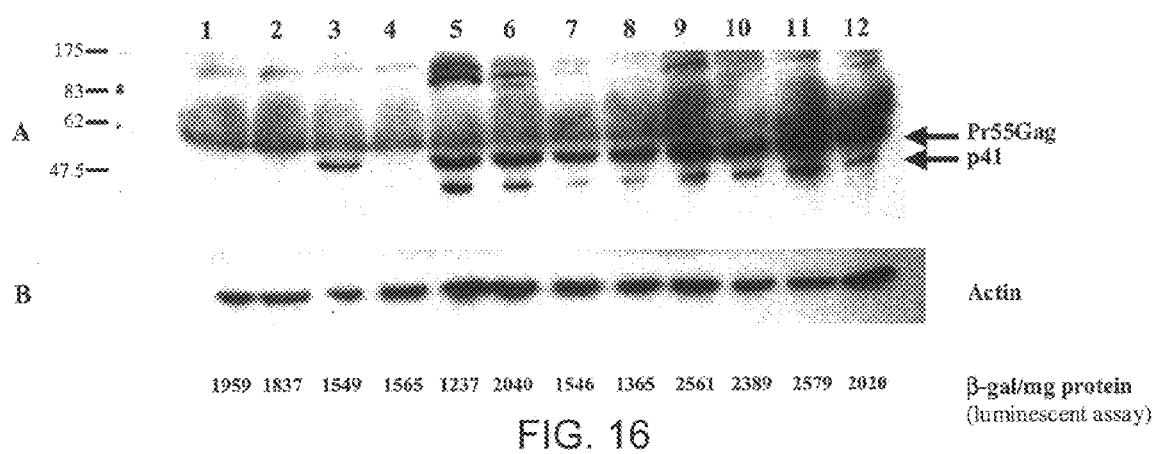
FIG. 16 shows the effect of LMB on protein production.

FIG. 16 shows the effect of LMB on protein production. 293T cells were transfected with 1 µg pCMV-Rev and 3 µg of pGP-RRE3/pSYNGP/pSYNGP-RRE (+/−1 µg pCMV-Rev). Transfections were done in duplicate. 5 hours post transfection the medium was replaced with fresh medium in the first set and with fresh medium containing 7.5 nM LMB in the second. 20 hours later the cells were lysed and protein production was estimated by Western blot analysis. HIV-1 positive human serum was used to detect the gag-pol proteins (A) and an anti-actin antibody was used as an internal control (B). Lanes: 1. pGP-RRE3, 2. pGP-RRE3+LMB, 3. pGP-RRE3+pCMV-Rev, 4. pGP-RRE3+pCMV-Rev+LMB, 5. pSYNGP, 6. pSYNGP+LMB, 7. pSYNGP+pCMV-Rev, 8. pSYNGP+pCMV-Rev+LMB, 9. pSYNGP-RRE, 10. pSYNGP-RRE+LMB, 11. pSYNGP-RRE+pCMV-Rev, 12. pSYNGP-RRE+pCMV-Rev+LMB.

Figure 17:
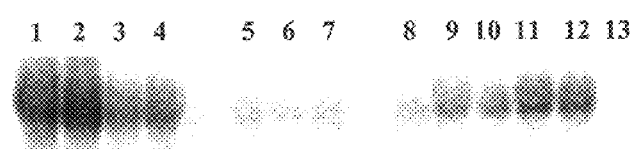
FIG. 17 shows the cytoplasmic RNA levels of the vector genomes.
Figure 19:
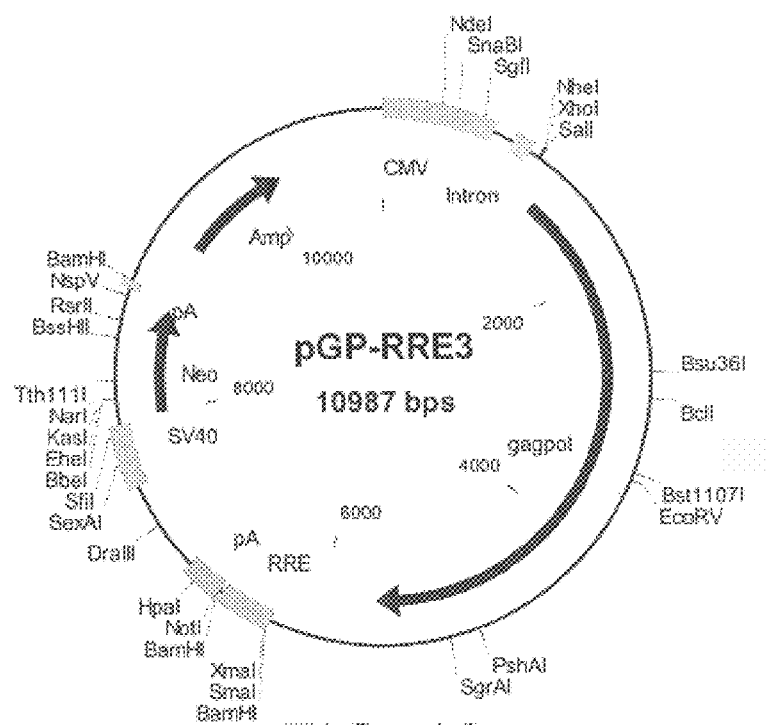
FIG. 19 shows a schematic representation of pGP-RRE3.
Figure 20:
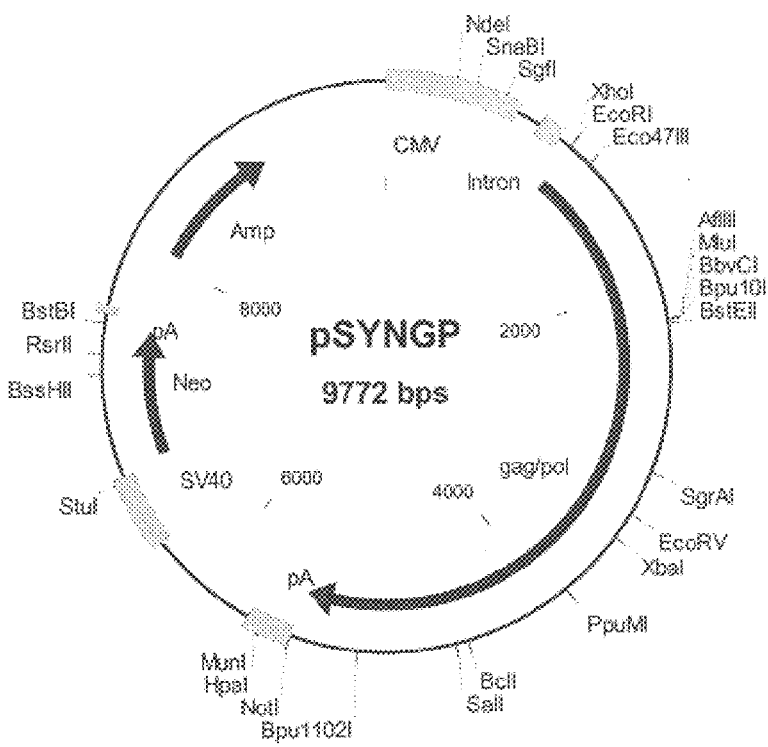
FIG. 20 shows a schematic representation of pSYNGP.

FIG. 17 shows the cytoplasmic RNA levels of the vector genomes. 293T cells were transfected with 10 µg of each vector genome. Cytoplasmic RNA was extracted 48 hours post transfection. 20 µg of RNA were used from each sample for Northern blot analysis. The 700 bp probe was designed to hybridise to all vector genome RNAs (see Materials and Methods). Lanes: 1. pH6nZ, 2. pH6nZ+pCMV-Rev, 3. pH6.1nZ, 4. pH6.1nZ+pCMV-Rev, 5. pHS1nZ, 6. pHS2nZ, 7. pHS3nZ, 8. pHS4nZ, 9. pHS5nZ, 10. pHS6nZ, 11. pHS7nZ, 12. pHS8nZ, 13. pCMV-Rev.

FIG. 18 shows transduction efficiency at MOI 1. Viral stocks were generated by co-transfection of each gag-pol expression plasmid (5 or 0.5 µg), 15 µg pH6nZ or pHS3nZ (vector genome plasmid) and 5 µg pHCMVG (VSV envelope expression plasmid) on 293T cells. Virus was concentrated as previously described (45) and transduction efficiency was determined at m.o.i.'s 0.01–1 on HT1080 cells. There was a linear correlation of transduction efficiency and m.o.i. in all cases. An indicative picture at m.o.i. 1 is shown here. Transduction efficiency was >80% with either genome, either gag-pol and either high or low amounts of pSYNGP. Titres before concentration (I.U./ml): on 293T cells: A. $6.6 \times 10^5$, B. $7.6 \times 10^5$, C. $9.2 \times 10^5$, D. $1.5 \times 10^5$, on HT1080 cells: A. $6.0 \times 10^4$, B. $9.9 \times 10^4$, C. $8.0 \times 10^4$, D. $2.9 \times 10^4$. Titres after concentration (I.U./ml) on HT1080 cells: A. $6.0 \times 10^5$, B. $2.0 \times 10^6$, C. $1.4 \times 10^6$, D. $2.0 \times 10^5$.

FIG. 21 shows vector titers obtained with differed gag-pol constructs. Viral stocks were generated by co-transfection of each gag-pol expression plasmid, pH6nZ (vector genome plasmid) and pHCMVG (VSV envelope. expression plasmid, 2.5 µg for each transfection) on 293T cells. Titres (I.U./ml of virs stock) were measured on 293T cells by counting the number of blue colonies following X-Gal staining 48 hours after transduction. Experiments were performed at least twice and the variation between experiments was less than 15%.

FIG. 22 shows vector titres from the Rev/RRE (−) and (+) genomes. The retroviral vectors were generated as described in the Examples. Titres (I.U./ml of viral stock+SD) were determined in 293T cells.

FIG. 23 shows vector titres from the pHS series of vector genomes. The retroviral vector was generated as described in the Examples. Titres (I.U./ml of viral stock+SD) were determined in 293T cells. Rev is provided from pCMV-Rev. Note that pH6nZ expresses Rev and contains the RRE. None of the other genomes express Rev or contain the RRE. Expression from pSYNGP is Rev independent, whereas it is Rev dependent for pGP-RRE3.

FIG. 24 shows vector titres for the pHS series of vector genomes in the presence or absence of Rev/RRE. The retroviral vector was generated as described in the Examples. 5 µg of vector genome, 5 µg of pSYNGP and 2.5 µg of pHCMVG were used and titres (I.U./ml) were determined in 293T cells. Experiments were performed at least twice and the variation between experiments was less than 15%. Rev is provided from pCMV-Rev (1 µg). Note that pH6nZ expresses Rev and contains the RRE. None of the pHS genomes expresses Rev and only pHS1nZR, pHS3nZR, pHS7nZR and pH6.1 nZR contain the RRE. gag-pol expression from pSYNGP is Rev independent.

We show that codon optimisation of the HIV-1 gag-pol gene results in a 10-fold increase in steady state levels of cognate RNA with an equivalent 10-fold increase in protein production. Furthermore, unlike the wild type gag-pol gene, expression occurs independently of the Rev/RRE system. We further demonstrate that, consistent with Rev indepedence, Leptomycin B has no effect on expression, implying that the exportin-1 (CRM1) nuclear export pathway is not involved.

Although Rev independent expression of HIV-1 genes has been previously shown (11, 28), in previous studies increased protein production upon codon optimisation has been attributed to more efficient translation (11). Without wishing to be bound by any theory, it is believed that elimination of INS sequences residing within the coding sequence (82, 29, 99) is one possible explanation for this result. Another possibility is that inefficient translation can lead to increased probability of mRNA degradation and this has been obviated by the change in codon bias. For example, it has been shown that mRNAs that contain premature termination codons are easily degraded (54), reviewed in (74), or that sequences involved in rapid mRNA turnover can be active only when they are part of the translation ORF (e.g. in c-myc, (109). However, the increased levels of protein paralleled rather than exceeded the increase in RNA levels. It is possible that gag is autoregulating its expression to allow viral RNA packaging as it has been proposed for RSV (101). This is further supported by the fact that HIV-1 gag interacts with translation factors and inhibits translation in vitro (60, 107) and it could also explain why codon optimisation for HIV-1 env results in a significant augmentation in protein levels and equal RNA levels (11) and not for the gag-pol.

We also demonstrate that HIV-1 gag INS sequences can act in a position dependent manner, irrespective of translation and their effects are INS size dependent. Without wishing to be bound by any theory, the INS elements may induce mRNA deadenylation and rapid degradation in the cytoplasm. This is the favoured scenario for AU-rich elements found in the 3' UTR of cellular labile mRNAs (111). Alternatively, they may exert their effects prior to the exit of the mRNA from the nucleus (87). The results obtained here are in agreement with the second hypothesis, as the observed effect seemed to be translation independent, and indicate that HIV-1 gag INS elements may also act by retaining the mRNA in the nucleus (90) and possibly directing it towards a nuclear degradation pathway (83, 87). This is further supported by previous reports showing that HIV-1 pol INS elements interact with several cellular factors, one of which has been identified as hnRNP C, a component of the splicing machinery (90). However, a translational effect cannot be ruled out.

With our codon optimised gene we achieved higher vector particle production compared to the wild type gene, but this did not convert into higher vector titres, indicating that gag-pol is not limiting. As expected however, in plasmid ratios where the gag-pol is limiting, i.e. 1 gag-pol: 50 genomes, then a 10-fold increase in titres was observed with the codon optimised gene.

Proviral clones pW13 (77) and pNL4-3 (49) were used.

Construction of a Genome

The HIV gag-pol sequence was codon optimised (FIG. 4; SEQ I.D. No. 2 and SEQ I.D. 5) and synthesized using overlapping oligos of around 40 nucleotides. This has three advantages. Firstly it allows an HIV based vector to carry ribozymes and other therapeutic factors. Secondly the codon optimisation generates a higher vector titre due to a higher level of gene expression. Thirdly gag-pol expression becomes rev independent which allows the use of anti-rev or RRE factors.

Conserved sequences within gag-pol were identified by reference to the HIV Sequence database at Los Alamos National Laboratory and used to design ribozymes. Because of the variability between subtypes of HIV-1 the ribozymes were designed to cleave the predominant subtype within North America, Latin America and the Caribbean, Europe, Japan and Australia; that is subtype B. The sites chosen were cross-referenced with the synthetic gag-pol sequence to ensure that there was a low possibility of cutting the codon optimised gag-pol mRNA. The ribozymes were designed with XhoI and SalI sites at the 5' and 3' end respectively. This allows the construction of separate and tandem ribozymes.

The ribozymes are hammerhead (25) structures of the following general structure:

The codon optimised gene may be of particular use for the production of simpler and safer HIV vectors. To date these still require the provision of Rev to facilitate gag-pol expression (64, 12) and this requirement is now removed by using the codon optimised gene. We have now demonstrated the feasibility of making a fully Rev independent vector system without a significant compromise in titre. Our results indicate that the vector genome is also Rev dependent when large portions of gag or gag and env are present, but also that retention of more than 260 bases of gag is required for efficient infectious vector production. Further manipulations, such as inclusion of a CTE in the vector genome may be used to overcome these limitations and fully restore titres.

There are other advantages of employing a codon optimised gag-pol, for example therapeutic ribozymes can now be targeted against gag and pol and yet still be delivered by HIV vectors that will be resistant to their effects during production.

In conclusion, we have shown that codon optimisation of the HIV-1 gag-pol gene leads to higher expression without the requirement for Rev/RRE. Furthermore, based on this codon optimised gene, we have constructed an HIV-1 based vector system that now lacks all the accessory proteins, retains only minimal HIV-1 sequences (required for packaging and reverse transcription) in the vector genome construct.

EXAMPLES

Cell Lines 293T cells (63) and HeLa cells (71) were maintained in Dubecco's modified Eagle's medium containing 10% (v/v) fetal calf serum and supplemented with L-glutamine and antibiotics (penicillin-streptomycin). 293T cells were obtained from D. Baltimore (Rockefeller University).

HIV-1 Proviral Clones

The catalytic domain of the ribozyme (Helix II) can tolerate some changes without reducing catalytic turnover.

The cleavage sites, targeting gag and pol, with the essential GUX triplet (where X is any nucleotide base) are as follows:

GAG 1 5' UAGUAAGAAUGUAUAGCCCUAC (SEQ ID NO: 7)
GAG 2 5' AACCCAGAUUGUAAGACUAUUU (SEQ ID NO: 8)
GAG 3 5' UGUUUCAAUUGUGGCAAAGAAG (SEQ ID NO: 9)
GAG 4 5' AAAAAGGGCUGUUGGAAAUGUG (SEQ ID NO: 10)
POL 1 5' ACGACCCCUCGUCACAAUAAAG (SEQ ID NO: 11)
POL 2 5' GGAAUUGGAGGUUUUAUCAAAG (SEQ ID NO: 12)
POL 3 5' AUAUUUUCAGUUCCCUUAGAU (SEQ ID NO: 13)
POL 4 5' UGGAUGAUUUGUAUGUAGGAUC (SEQ ID NO: 14)
POL 5 5' CUUUGGAUGGGUUAUGAACUCC (SEQ ID NO: 15)
POL 6 5' CAGCUGGACUGUCAAUGACAUA (SEQ ID NO: 16)
POL 7 5' AACUUUCUAUGUAGAUGGGGCA (SEQ ID NO: 17)
POL 8 5' AAGGCCGCCUGUUGGUGGGCAG (SEQ ID NO: 18)
POL 9 5' UAAGACAGCAGUACAAAUGGCA (SEQ ID NO: 19)

Figure 1:
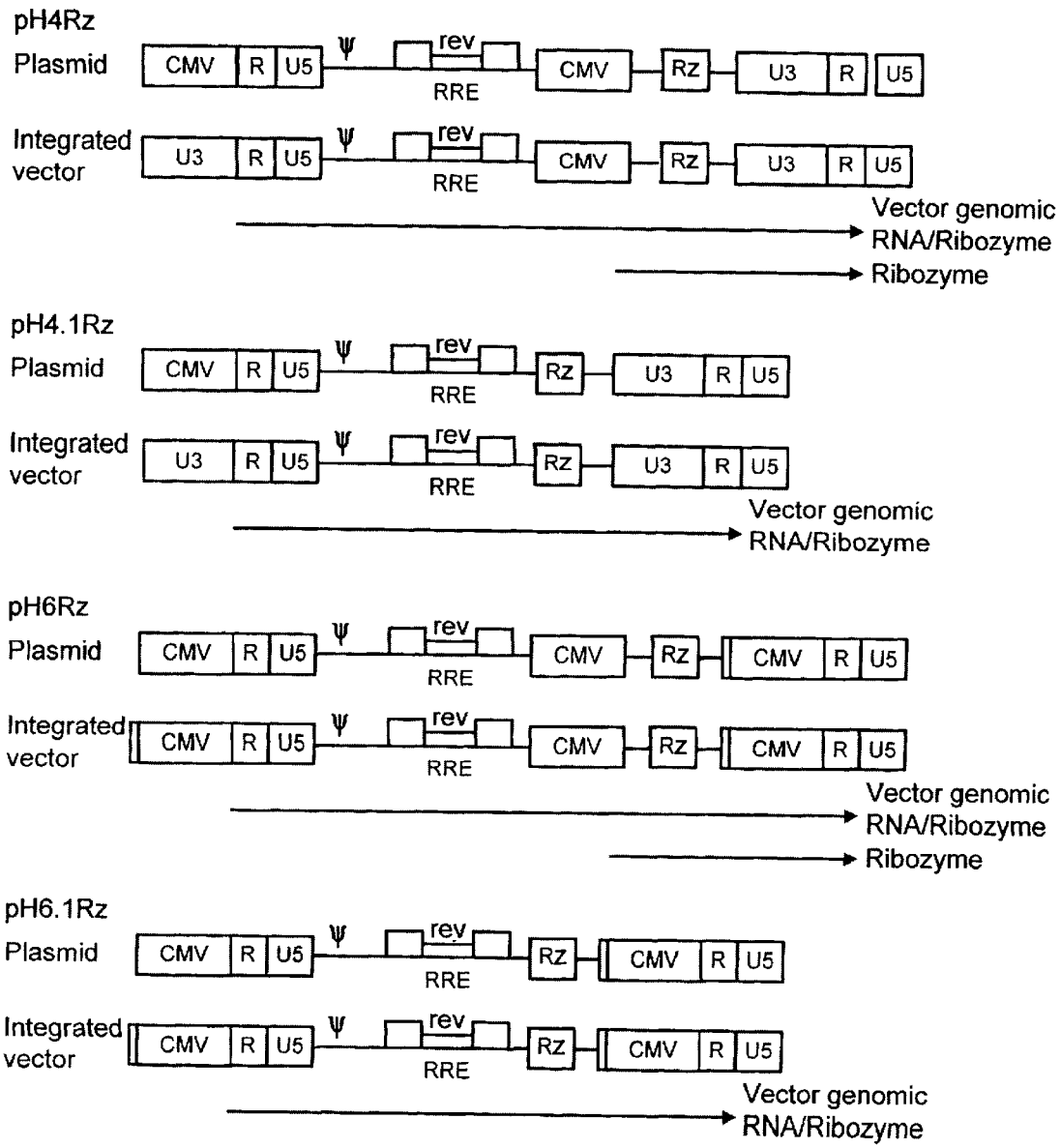
FIG. 1 shows schematically ribozymes inserted into four different HIV vectors.

The ribozymes are inserted into four different HIV vectors (pH4 (10), pH6, pH4.1, or pH6.1) (FIG. 1). In pH4 and pH6, transcription of the ribozymes is driven by an internal HCMV promoter (9). From pH4.1 and pH6.1, the ribozymes are expressed from the 5' LTR. The major difference between pH4 and pH6 (and pH4.1 and pH6.1) resides in the 3' LTR in the production plasmid. pH4 and pH4.1 have the HIV U3 in the 3' LTR. pH6 and pH6.1 have HCMV in the 3'LTR. The HCMV promoter replaces most of the U3 and will drive expression at high constitutive levels while the HIV-1 U3 will support a high level of expression only in the presence of Tat.

Figure 2:
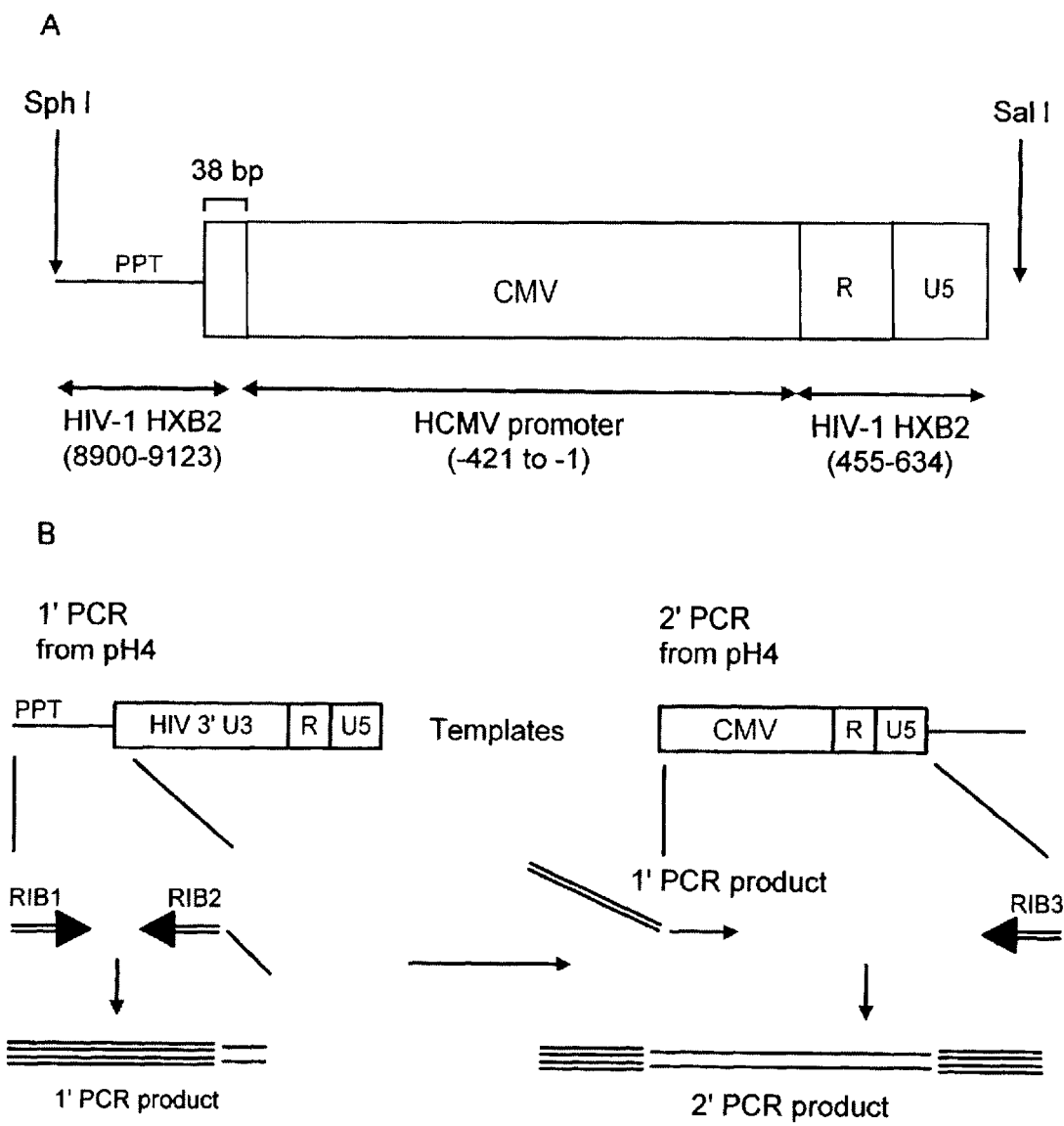
FIG. 2 shows schematically how to create a suitable 3' LTR by PCR.

The HCMV/HIV-1 hybrid 3' LTR is created by recombinant PCR with three PCR primers (FIG. 2). The first round of PCR is performed with RIB1 and RIB2 using pH4 (12) as the template to amplify the HIV-1 HXB2 sequence 8900–9123. The second round of PCR makes the junction between the 5' end of the HIV-1 U3 and the HCMV promoter by. amplifying the hybrid 5' LTR from pH4. The PCR product from the first PCR reaction and RIB3 serves as the 5' primer and 3' primer respectively.

RIB 1:
  5'-CAGCTGCTCGAGCAGCTGAAGCTTGCATGC-3' (SEQ ID NO: 20)
RIB 2:
  5'-GTAAGTTATGTAACGGACGATATCTTGTCTTCTT-3' (SEQ ID NO: 21)
RIB3: 5'-CGCATAGTCGACGGGCCCGCCACTGCTAGA GATTTTC-3' (SEQ ID NO: 22)

The PCR product is then cut with SphI and SalI and inserted into pH4 thereby replacing the 3' LTR. The resulting plasmid is designated pH6. To construct pH4.1 and pH6.1, the internal HCMV promoter (SpeI-XhoI) in pH4 and pH6 is replaced with the polycloning site of pBluescript II KS+(Stratagene) (SpeI-XhoI).

The ribozymes are inserted into the XhoI sites in the genome vector backbones. Any ribozymes in any configuration could be used in a similar way.

Construction of a Packaging System

The packaging system can take various forms. In a first form of packaging system, the HIV gag, pol components are co-expressed with the HIV env coding sequence. In this case, both the gag, pol and the env coding sequences are altered such that they are resistant to the anti-HIV ribozymes that are built into the genome. At the same time as altering the codon usage to achieve resistance, the codons can be chosen to match the usage pattern of the most highly expressed mammalian genes. This dramatically increases expression levels (28, 29) and so increases titre. A codon optimised HIV env coding sequence has been described by Haas et al (9). In the present example, a modified codon optimised HIV env sequence is used (SEQ I.D. No. 3). The corresponding env expression plasmid is designated pSYNgp160 mn. The modified sequence contains extra motifs not used by Haas et al. The extra sequences were taken from the HIV env sequence of strain MN and codon optimised. Any similar modification of the nucleic acid sequence would function similarly as long as it used codons corresponding to abundant tRNAs (42) and lead to resistance to the ribozymes in the genome.

SYNgp

Figure 8:
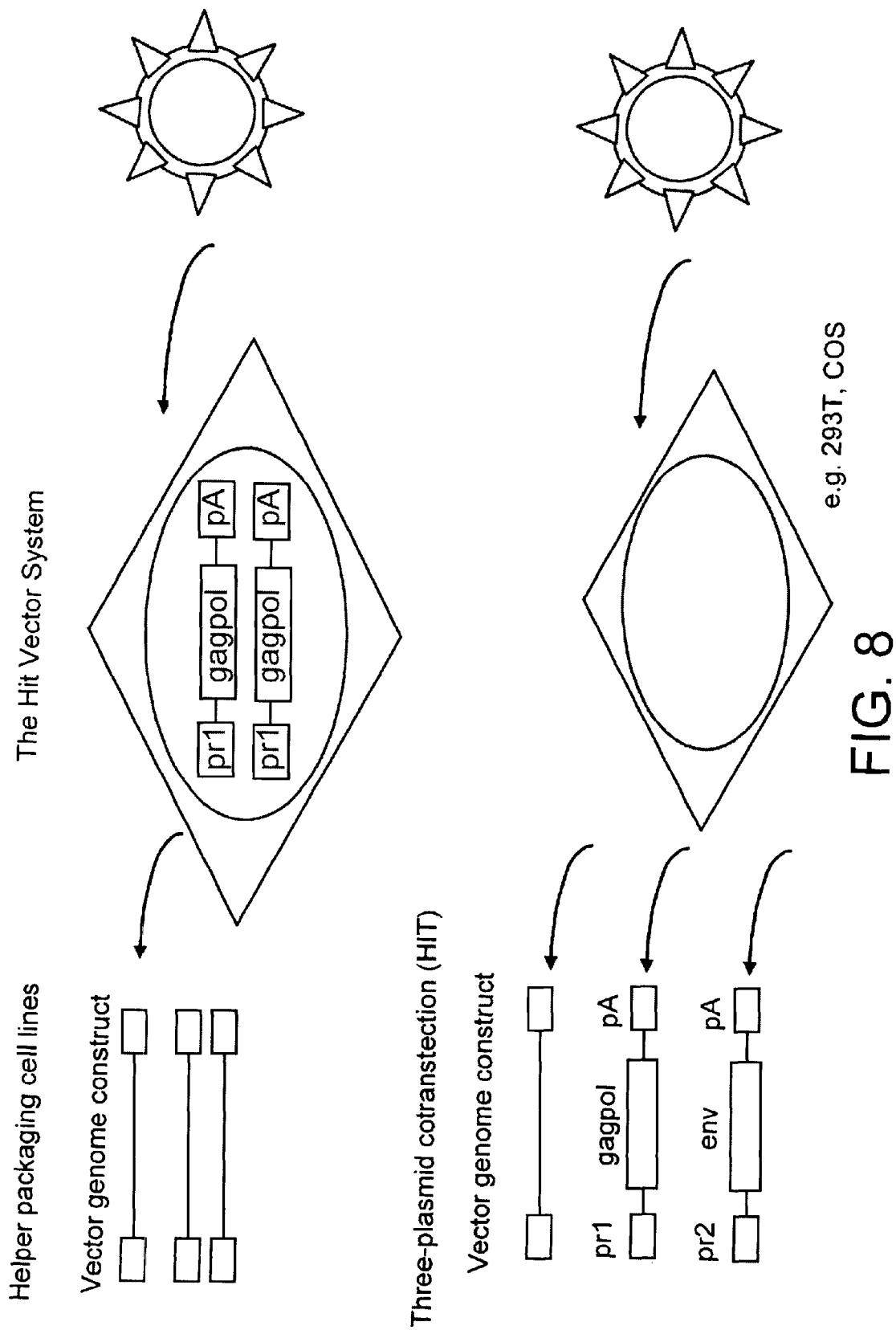
FIG. 8 shows the principle behind two systems for producing retroviral vector particles.

In one example of a gag, pol coding sequence with optimised codon usage, overlapping oligonucleotides are synthesised and then ligated together to produce the synthetic coding sequence. The sequence of a wild-type gag-pol sequence (Genbank accession no. K03455) is shown in SEQ I.D. No 1 and two possible sequences of a synthetic optimised gag-pol sequence (gagpol-SYNgp and pSYNGP) are shown in SEQ I.D. Nos 2 and 5 respectively. Their codon usage is shown in FIGS. 3 and 4, respectively. The sequence of a wild type env coding sequence (Genbank Accession No. M17449) is given in SEQ I.D. No 3, the sequence of a synthetic codon optimised sequence is given in SEQ. I.D. No. 4 and their codon usage tables are given in FIGS. 5 and 6, respectively. As with the env coding sequence any gag, pol sequence that achieves resistance to the ribozymes could be used. The synthetic sequence designated gagpol-SYNgp has an EcoRI site at the 5' end and a NotI site at the 3' end. It is inserted into pCIneo (Promega) to produce plasmid pSYNgp. Vector particles can be produced either from a transient three-plasmid transfection system similar to that described by Soneoka et al. (33) or from producer cell lines similar to those used for other retroviral vectors (20, 35, 39). These principles are illustrated in FIGS. 7 and 8. For example, by using pH6Rz, pSYNgp or pSYNGP and pRV67 (VSV-G expression plasmid) in a three plasmid transfection of 293T cells (FIG. 8), as described by Soneoka et al (33), vector particles designated H6Rz-VSV are produced. These transduce the H6Rz genome to CD4+ cells such as C1866 or Jurkat and produce the multitarget ribozymes. HIV replication in these cells is now severely restricted.

pSYNGP

The codon optimised gag-pol gene was constructed by annealing a series of short overlapping oligonucleotides (approximately 30–40mers with 25% overlap, i.e. approximately 9 nucleotides). Oligonucleotides were purchased from R&D SYSTEMS (R&D Systems Europe Ltd, 4-10 The Quadrant, Barton Lane, Abingdon, OX14 3YS, UK). Codon optimisation was performed using the sequence of HXB-2 strain (AC: K03455) (67). The Kozak consensus sequence for optimal translation initiation (78) was also included. A fragment from base 1222 from the beginning of gag until the end of gag (1503) was not optimised in order to maintain the frameshift site and the overlap between the gag and pol reading frames. This was from clone pNL4-3. The −1 ribosomal frameshift (occuring at the sequence TTTTTTA, 1296 bases downstream of the gag ATG) brings the overlapping out-of-phase gag and pol genes into translational phase (76, 108), thus allowing expression of the gag-pol polyprotein. Sequences downstream of the frameshift site that form secondary structures also play a role in facilitating the event (by stalling the ribosomes and allowing the 'slippage' to occur) (57, 92). Consequently, a 281 bp fragment spanning the frameshift site and the overlapping region of the two reading frames (gag and gag-pol) was retained. (When referring to base numbers within the gag-pol gene base 1 is the A of the gag ATG, which corresponds to base 790 from the beginning of the HXB2 sequence. When referring to sequences outside the gag-pol then the numbers refer to bases from the beginning of the HXB2 sequence, where base 1 corresponds to the beginning of the 5' LTR). Some deviations from optimisation were made in order to introduce convenient restriction sites. The final codon usage is shown in Table 4a, which now resembles that of highly expressed human genes and is quite different from that of the wild type HIV-1 gag-pol. The gene was cloned into the mammalian expression vector pCIneo (Promega) in the EcoRI-NotI sites. The resulting plasmid was named pSYNGP. Sequencing of the gene in both strands verified the absence of any mistakes. A sequence comparison between the codon optimised and wild type HIV gag-pol sequence is shown in FIG. 9.

Rev/RRE Constructs

The HIV-1 RRE sequence (bases 7769–8021 of the HXB2 sequence) was amplified by PCR from pWI3 proviral clone with primers bearing the NotI restriction site and was subsequently cloned into the NotI site of pSYNGP. The resulting plasmids were named pSYNGP-RRE (RRE in the correct orientation) and pSYNGP-ERR (RRE in the reverse orientation).

Pseudotyped Viral Particles

In a second form of the packaging system a synthetic gag, pol cassette is coexpressed with a non-HIV envelope coding sequence that produces a surface protein that pseudotypes HIV. This could be for example VSV-G (20, 41), amphotropic MLV env (6, 34) or any other protein that would be incorporated into the HIV particle (37). This includes molecules capable of targeting the vector to specific tissues. Coding sequences for non-HIV envelope proteins not cleaved by the ribozymes and so no sequence modification is required (although some sequence modification may be desirable for other reasons such as optimisation for codon usage in mammalian cells).

Vector Genome Constructs pH6nZ is derived from pH4Z (12) by the addition of a single nucleotide to place an extra guanine residue that was missing from pH4Z at the 5' end of the vector genome transcript to optimise reverse transcription. In addition the gene coding for β-galactosidase (LacZ) was replaced by a gene encoding for a nuclear localising β-galactosidase. (We are grateful to Enca Martin-Rendon and Said Ismail for providing pH6nZ). In order to construct Rev(−) genome constructs the following modifications were made: a) A 1.8 kb PstI-PstI fragment was removed from pH6nZ, resulting in plasmid pH6.1nZ and b) an EcoNI (filled)-SphI fragment was substituted with a SpeI (filled)-SphI fragment from the same plasmid (pH6nZ), resulting in plasmid pH6.2nZ. In both cases sequences within gag (nt 1–625) were retained, as they have been shown to play a role in packaging (93). Rev, RRE and any other residual env sequences were removed. pH6.2nZ further contains the env splice acceptor, whereas pH6.1nZ does not.

A series of vectors encompassing further gag deletions plus or minus a mutant major splice donor (SD) (GT to CA mutation) were also derived from pH6Z. These were made by PCR with primers bearing a NarI (5' primers) and an SpeI (3' primers) site. The PCR products were inserted into pH6Z at the NarI-SpeI sites. The resulting vectors were named pHS1nZ (containing HIV-1 sequences up to gag 40), pHS2nZ (containing HIV-1 sequences up to gag 260), pHS3nZ (containing HIV-1 sequences up to gag 360), pHS4nZ (containing HIV-1 sequences up to gag 625), pHS5nZ (same as pHS1nZ but with a mutant SD), pHS6nZ (same as pHS2nZ but with a mutant SD), pHS7nZ (same as pHS3nZ but with a mutant SD) and pHS8nZ (same as pHS4nZ but with a mutant SD).

In addition, the RRE sequence (nt 7769–8021 of the HXB2 sequence) was inserted in the SpeI (filled) site of pH6.1nZ, pHS1nZ, pHS3nZ and pHS7nZ resulting in plasmids pH6.1nZR, pHS1nZR, pHS3nZR and pHS7nZR respectively.

Transient Transfections, Transductions and Determination of Viral Titres

These were performed as previously described (12, 33). Briefly, 293T cells were seeded on 6 cm dishes and 24 hours later they were transiently transfected by overnight calcium phosphate treatment. The medium was replaced 12 hours post-transfection and unless otherwise stated supernatants were harvested 48 hours post-transfection, filtered (through 0.22 or 0.45 µm filters) and titered by transduction of 293T cells. For this reason supernatant at appropriate dilutions of the original stock was added to 293T cells (plated onto 6 or 12 well plates 24 hours prior to transduction). 8 µg/ml Polybrene (Sigma) was added to each well and 48 hours post transduction viral titres were determined by X-gal staining.

Luminescent β-galactosidase (β-gal) Assays

These were performed on total cell extracts using a luminescent β-gal reporter system (CLONTECH). Untransfected 293T cells were used as negative control and 293T cells transfected with pCMV-βgal (CLONTECH) were used as positive control.

RNA Analysis

Total or cytoplasmic RNA was extracted from 293T cells by using the RNeasy mini kit (QUIAGEN) 36–48 hours post-transfection. 5–10 µg of RNA was subjected to Northern blot analysis as previously described (98). Correct fractionation was verified by staining of the agarose gel. A probe complementary to bases 1222–1503 of the gag-pol gene was amplified by PCR from HIV-1 pNL4-3 proviral clone and was used to detect both the codon optimised and wild type gag-pol mRNAs. A second probe, complementary to nt 1510–2290 of the codon optimised gene was also amplified by PCR from plasmid pSYNGP and was used to detect the codon optimised genes only. A 732 bp fragment complementary to all vector genomes used in this study was prepared by an SpeI-AvrII digestion of pH6nZ. A probe specific for ubiquitin (CLONTECH) was used to normalise the results. All probes were labelled by random labelling (STRATAGENE) with $\alpha$-$^{32}$P dCTP (Amersham). The results were quantitated by using a Storm PhosphorImager (Molecular Dynamics) and shown in FIG. 12. In the total cellular fractions the 47S rRNA precursor could be clearly seen, whereas it was absent from the cytoplasmic fractions. As expected (84), Rev stimulates the cytoplasmic accumulation of wild type gag-pol mRNA (lanes 1c and 2c). RNA levels were 10–20 fold higher for the codon optimised gene compared to the wild type one, both in total and cytoplasmic fractions (compare lanes 3t-2t, 3c-2c, 10c-8c). The RRE sequence did not significantly destabilise the codon optimised RNAs since RNA levels were similar for codon optimised RNAs whether or not they contained the RRE sequence (compare lanes 3 and 5). Rev did not markedly enhance cytoplasmic accumulation of the codon optimised gag-pol mRNAs, even when they contained the RRE sequence (differences in RNA levels were less than 2-fold, compare lanes 3–4 or 5–6).

It appeared from a comparison of FIGS. 10 and 12 that all of the increase in protein expression from syngp could be accounted for by the increase in RNA levels. In order to investigate whether this was due to saturating levels of RNA in the cell, we transfected 0.1, 1 and 10 µg of the wild type or codon optimised expression vectors into 293T cells and compared protein production. In all cases protein production was 10-fold higher for the codon optimised gene for the same amount of transfected DNA, while increase in protein levels was proportional to the amount of transfected DNA for each individual gene. It seems likely therefore that the enhanced expression of the codon optimised gene can be mainly attributed to the enhanced RNA levels present in the cytoplasm and not to increased translation.

Protein Analysis

Total cell lysates were prepared from 293T cells 48 hours post-transfection (unless otherwise stated) with an alkaline lysis buffer. For extraction of proteins from cell supernatants the supernatant was first passed through a 0.22 µm filter and the vector particles were collected by centrifugation of 1 ml of supernatant at 21,000 g for 30 minutes. Pellets were washed with PBS and then re-suspended in a small volume (2–10 µl) of lysis buffer. Equal protein amounts were separated on a SDS 10–12% (v/v) polyacrylamide gel. Proteins were transferred to nitrocellulose membranes which were probed sequentially with a 1:500 dilution of HIV-1 positive human serum (AIDS Reagent Project, ADP508, Panel E) and a 1:1000 dilution of horseradish peroxidase labelled anti-human IgG (Sigma, A0176). Proteins were visualised using the ECL or ECL-plus western blotting detection reagent (Amersham). To verify equal protein loading, membranes were stripped and re-probed with a 1:1000 dilution of anti-actin antibody (Sigma, A2066), followed by a 1:2000 dilution of horseradish peroxidase labelled anti-rabbit IgG (Vector Laboratories, PI-1000).

Expression of gag-pol Gene Products and Vector Particle Production

The wild type gag-pol (pGP-RRE3) (12), and codon optimised expression vectors (pSYNGP, pSYNGP-RRE and pSYNGP-ERR) were transiently transfected into 293T cells. Transfections were performed in the presence or absence of a Rev expression vector, pCMV-Rev (66), in order to assess Rev-dependence for expression. Western blot analysis was performed on cell lysates and supernatants to assess protein production. The results are shown in FIG. 10. As expected (72), expression of the wild type gene is observed only when Rev is provided in trans (lanes 2 and 3). In contrast, when the codon optimised gag-pol was used, there was high level expression in both the presence and absence of Rev (lanes 4 and 5), indicating that in this system there was no requirement for Rev. Protein levels were higher for the codon optimised gene than for the wild type gag-pol (compare lanes 4–9 with lane 3). The difference was more evident in the cell supernatants (approximately 10-fold higher protein levels for the codon optimised gene compared to the wild type one, quantitated by using a PhosphorImager) than in the cell lysates.

In previous studies where the RRE has been included in gag-pol expression vectors that had been engineered to remove INS sequences, inclusion of the RRE lead to a decrease in protein levels, that was restored by providing Rev in trans (28). In our hands, the presence of the RRE in the fully codon optimised gag-pol mRNA did not affect protein levels and provision of Rev in trans did not further enhance expression (lanes 6 and 7).

In order to compare translation rates between the wild type and codon optimised gene, protein production from the wild type and codon optimised expression vector was determined at several time intervals post transfection into 293T cells. Protein production and particle formation was determined by Western blot analysis and the results are shown in FIG. 11. Protein production and particle formation was 10-fold higher for the codon optimised gag-pol at all time points.

To further determine whether this enhanced expression that was observed with the codon optimised gene was due to better translation or due to effects on the RNA, RNA analysis was carried out.

The Efficiency of Vector Production Using the Codon Optimised gag-pol Gene

To determine the effects of the codon optimised gag-pol on vector production, we used an HIV vector genome, pH6nZ and the VSV-G envelope expression plasmid pHCMVG (113), in combination with either pSYNGP, pSYNGP-RRE, pSYNGP-ERR or pGP-RRE3 as a source for the gag-pol in a plasmid ratio of 2:1:2 in a 3 plasmid co-transfection of 293T cells (12). Whole cell extracts and culture supernatants were evaluated by Western blot analysis for the presence of the gag and gag-pol gene products. Particle production was, as expected (FIG. 10), 5–10 fold higher for the codon optimised genes when compared to the wild type.

To determine the effects of the codon optimised gag-pol gene on vector titres, several ratios of the vector components were used. The results are shown in FIG. 21. Where the gag-pol was the limiting component in the system (as determined by the drop in titres observed with the wild type gene), titres were 10-fold higher for the codon optimised vectors. This is in agreement with the higher protein production observed for these vectors, but suggests that under normal conditions of vector production gag-pol is saturating and the codon optimisation gives no maximum yield advantage.

The Effect of HIV-1 gag INS Sequences on the Codon Optimised Gene is Position Dependent It has previously been demonstrated that insertion of wild type HIV-1 gag sequences downstream of other RNAs, e.g. HIV-1 tat (99), HIV-1 gag (28) or CAT (82) can lead to a dramatic decrease in steady state mRNA levels, presumably as a result of the INS sequences. In other cases, e.g. for β-globin (87), it was shown that the effect was splice site dependent. Cellular AREs (AU-rich elements) that are found in the 3' UTR of labile mRNAs may confer mRNA destabilisation by inducing cytoplasmic deadenylation of the transcripts (111). To test whether HIV-1 gag INS sequences would destabilise the codon optimised RNA, the wild-type HIV-1 gag sequence, or parts of it (nt 1–625 or nt 625–1503), were amplified by PCR from the proviral clone pW13. All fragments were blunt ended and were inserted into pSYNGP or pSYNGP-RRE at either a blunted EcoR1 or NotI site (upstream or downstream of the codon optimised gag-pol gene repectively). As controls the wt HIV-1 gag in the reverse orientation (as INS sequences have been shown to act in an orientation dependent manner, (82) (pSYN7) and lacZ, excised from plasmid pCMV-βGal (CLONTECH) (in the correct orientation) (pSYN8) were also inserted in the same site. Contrary to our expectation, as shown in FIG. 13, the wild type HIV-1 gag sequence did not appear to significantly affect RNA or protein levels of the codon optimised gene. We further constructed another series of plasmids (by PCR and from the same plasmids) where the wild type HIV-1 gag in the sense or reverse orientation, subfragments of gag (nt 1–625 or nt 625–1503), the wild type HIV-1 gag without the ATG or with a frameshift mutation 25 bases downstream of the ATG, or nt 72–1093 of LacZ (excised from plasmid pH6Z), or the first 1093 bases of lacZ with or without the ATG were inserted upstream of the codon optimised HIV-1 gag-pol gene in pSYNGP and/or pSYNGP-RRE (pSYN9-pSYN22, FIG. 14). Northern blot analysis showed that insertion of the wild type HIV-1 gag gene upstream of the codon optimised HIV-1 gag-pol (pSYN9, pSYN10) lead to diminished RNA levels in the presence or absence of Rev/RRE (FIG. 15A, lanes 1–4 and FIG. 15B, lanes 1+12). The effect was not dependent on translation as insertion of a wild type HIV-1 gag lacking the ATG or with a frameshift mutation (pSYN12, pSYN13 and pSYN14) also diminished RNA levels (FIG. 15B, lanes 1–7). Western blot analysis verified that there was no HIV-1 gag translation product for pSYN12-14. However, it is possible that, as the wt HIV-1 gag exhibits such an adverse codon usage, it may act as a non-translatable long 5' leader for syngp, and if this is the case, then the ATG mutation should not have any effects.

Insertion of smaller parts of the wild type HIV-1 gag gene (pSYN15 and pSYN17) also lead to a decrease in RNA levels (FIG. 15B, lanes 1–3 and 8–9), but not to levels as low as when the whole gag sequence was used (lanes 1–3, 4–7 and 8–9 in FIG. 15B). This indicates that the effect of INS sequences is dependent on their size. Insertion of the wild type HIV-1 gag in the reverse orientation (pSYN11) had no effect on RNA levels (FIG. 15A, lanes 1 and 5–6). However a splicing event seemed to take place in that case, as indicated by the size of the RNA (equal to the size of the codon optimised gag-pol RNA) and by the translation product (gag-pol, in equal amounts compared to pSYNGP, as verified by Western blot analysis).

These data indicate therefore that wild type HIV-1 gag instability sequences act in a position and size dependent manner, probably irrespective of translation. It should also be noted that the RRE was unable to rescue the destabilised RNAs through interaction with Rev.

Construction of an HIV-1 Based Vector System that Lacks All the Accessory Proteins Until now several HIV-1 based vector systems have been reported that lack all accessory proteins but Rev (12, 88). We wished to investigate whether the codon optimised gene would permit the construction of an HIV-1 based vector system that lacks all accessory proteins. We initially deleted rev/RRE and any residual env sequences, but kept the first 625 nucleotides of gag, as they have been shown to play a role in efficient packaging (93). Two vector genome constructs were made, pH6.1nZ (retaining only HIV sequences up to nt 625 of gag) and pH6.2nZ (same as pH6.1nZ, but also retaining the env splice acceptor). These were derived from a conventional HIV vector genome that contains RRE and expresses Rev (pH6nZ). Our 3-plasmid vector system now expressed only HIV-1 gag-pol and the VSV-G envelope proteins. Vector particle titres were determined as described in the previous section. A ratio of 2:2:1 of vector genome (pH6Z or pH6.1nZ or pH6.2nZ): gag-pol expression vector (pGP-RRE3 or pSYNGP): pHCMV-G was used. Transfections were performed in the presence or absence of pCMV-Rev, as gag-pol expression was still Rev dependent for the wild type gene. The results are summarised in FIG. 22 and indicate that an HIV vector could be produced in the total absence of Rev, but that maximum titres were compromised at 20-fold lower than could be achieved in the presence of Rev. As gag-pol expression should be the same for pSYNGP with pH6nZ or pH6.1nZ or pH6.2nZ (since it is Rev independent), as well as for pGP-RRE3 when Rev is provided in trans, we suspected that the vector genome retained a requirement for Rev and was therefore limiting the titres. To confirm this, Northern blot analysis was performed on cytoplasmic RNA prepared from cells transfected with pH6nZ or pH6.1nZ in the presence or absence of pCMV-Rev. As can be seen in FIG. 17, lanes 1–4, the levels of cytoplasmic RNA derived from pH6nZ were 5–10 fold higher than those obtained with pH6.1nZ (compare lanes 1–2 to lanes 3–4). These data support the notion that RNA produced from the vector genome requires the Rev/RRE system to ensure high cytoplasmic levels. This may be due to inefficient nuclear export of the RNA, as INS sequences residing within gag were still present.

Further deletions in the gag sequences of the vector genome might therefore be necessary to restore titres. To date efficient packaging has been reported to require 360 (64) or 255 (61) nucleotides of gag in vectors that still retain env sequences, or about 40 nucleotides of gag in a particular combination of splice donor mutation, gag and env deletions (59, 61). In an attempt to remove the requirement for Rev/RRE in our vector genome without compromising efficient packaging we constructed a series of vectors derived from pH6nZ containing progressively larger deletions of HIV-1 sequences (only sequences upstream and within gag were retained) plus and minus a mutant major splice donor (SD) (GT to CA mutation). Vector particle titres were determined as before and the results are summarised in FIG. 23. As can be seen, deletion of up to nt 360 in gag (vector pHS3nZ) resulted in an increase in titres (compared to pH6.1nZ or pH6.2nZ) and only a 5-fold decrease (titres were $1.3$–$1.7 \times 10^5$) compared to pH6nZ. Further deletions resulted in titres lower than pHS3nZ and similar to pH6.1nZ. In addition, the SD mutation did not have a positive effect on vector titres and in the case of pHS3nZ it resulted in a 10-fold decrease in titres (compare titres for pHS3nZ and pHS7nZ in FIG. 23). Northern blot analysis on cytoplasmic RNA (FIG. 17, lanes 1 and 5–12) showed that RNA levels were indeed higher for pH6nZ, which could account for the maximum titres observed with this vector. RNA levels were equal for pHS1nZ (lane 5), pHS2nZ (lane 6) and pHS3nZ (lane 7) whereas titres were 5–8 fold higher for pHS3nZ. It is possible that further deletions (than that found in pHS3nZ) in gag might result in less efficient packaging (as for HIV-1 the packaging signal extends in gag) and therefore even though all 3 vectors produce similar amounts of RNA only pHS3nZ retains maximum packaging efficiency. It is also interesting to note that the SD mutation resulted in increased RNA levels in the cytoplasm (compare lanes 6 and 10, 7 and 11 or 8 and 12 in FIG. 17) but equal or decreased titres (FIG. 23). The GT dinucleotide that was mutated is in the stem of SL2 of the packaging signal (73). It has been reported that SL2 might not be very important for HIV-1 RNA encapsidation (73, 86), whereas SL3 is of great importance (81). Folding of the wild type and SD-mutant vector sequences with the RNAdraw software program revealed that the mutation alters significantly the secondary structure of the RNA and not only of SL2. It is likely therefore that although the SD mutation enhances cytoplasmic RNA levels it does not increase titres as it alters the secondary structure of the packaging signal.

To investigate whether the titre differences that were observed with the Rev minus vectors were indeed due to Rev dependence of the genomes, the RRE sequence (nt 7769–8021 of the HXB2 sequence) was inserted in the SpeI site (downstream of the gag sequence and just upstream of the internal CMV promoter) of pH6.1nZ, pHS1nZ, pHS3nZ and pHS7nZ, resulting in plasmids pH6.1nZR, pHS1nZR, pHS3nZR and pHS7nzR respectively. Vector particle titres were determined with pSYNGP and pHCMVG in the presence or absence of Rev (pCMV-Rev) as before and the results are summarised in FIG. 24. In the absence of Rev titres were further compromised for pH6.1nZR (7-fold compared to pH6.1nZ), pHS3nZR (6-fold compared to pHS3nZ) and pHS7nZR (2.5-fold compared to pHS7nZ). This was expected, as the RRE also acts as an instability sequence (56) and so it would be expected to confer Rev-dependence. In the presence of Rev titres were restored to the maximum titres observed for pH6nZ in the case of pHS3nZR ($5 \times 10^5$) and pH6.1nZR ($2 \times 10^5$). Titres were not restored for pHS7nZR in the presence of Rev. This supports the hypothesis that the SD mutation in pHS7nZ affects the structure of the packaging signal and thus the packaging ability of this vector genome, as in this case Rev may be able to stimulate vector genome RNA levels, as for pHS3nZR and pH6.1nZR, but it can not affect the secondary structure of the packaging signal. For vector pHS1nZ inclusion of the RRE did not lead to a decrease in titres. This could be due to the fact that pHS1nZ contains only 40 nucleotides of gag sequences and therefore even with the RRE the size of instability sequences is not higher than for pHS2nZ that gives equal titres to pHS1nZ. Rev was able to partially restore titres for pHS1nZR (10-fold increase when compared to pHS1nZ and 8-fold lower than pH6nZ) but not fully as in the case of pHS3nZ. This is also in agreement with the hypothesis that 40 nucleotides of HIV-1 gag sequences might not be sufficient for efficient vector RNA packaging and this could account for the partial and not complete restoration in titres observed with pHS1nZR in the presence of Rev.

In addition, end-point titres were determined for pHS3nZ and pH6nZ with pSYNGP in HeLa and HT1080 human cell lines. In both cases titres followed the pattern observed in 293T cells, with titres being 2–3 fold lower for pHS3nZ than for pH6nZ (See FIG. 10). Finally, transduction efficiency of vector produced with pHS3nZ or pH6nZ and different amounts of pSYNGP or pGP-RRE3 at different m.o.i.'s (and as high as 1) was determined in HT1 080 cells. This experiment was performed as the high level gag-pol expression from pSYNGP may result in interference by genome-empty particles at high vector concentrations. As expected for VSVG pseudotyped retroviral particles (52) transduction efficiencies correlated with the m.o.i.'s, whether high or low amounts of pSYNGP were used and with pH6nZ or pHS3nZ. For m.o.i. 1 transduction efficiency was approximately 50–60% in all cases (FIG. 18). The above data indicate that no interference due to genome-empty particles is observed in this experimental system.

The Codon Optimised gag-pol Gene Does Not Use the Exportin-1 Nuclear Export Pathway Rev mediates the export of unspliced and singly spliced HIV-1 mRNAs via the nuclear export receptor exportin-1 (CRM1) (68, 69, 94, 102, 103). Leptomycin B (LMB) has been shown to inhibit leucine-rich NES mediated nuclear export by disrupting the formation of the exportin-1/NES/RanGTP complex (91, 94). In particular, LMB inhibits nucleo-cytoplasmic translocation of Rev and Rev-dependent HIV mRNAs (110). To investigate whether exportin-1 mediates the export of the codon optimized gag-pol constructs, the effect of LMB on protein production was tested. Western blot analysis was performed on cell lysates from cells transfected with the gag-pol constructs (+/–pCMV-Rev) and treated or not with LMB (7.5 nM, for 20 hours, beginning treatment 5 hours post-transfection). To confirm that LMB had no global effects on transport, the expression of β-gal from the control plasmid pCMV-βGal was also measured. An actin internal control was used to account for protein variations between samples. The results are shown in FIG. 16. As expected (110), the wild type gag-pol was not expressed in the presence of LMB (compare lanes 3 and 4), whereas LMB had no effect on protein production from the codon optimized gag-pol, irrespective of the presence of the RRE in the transcript and the provision of Rev in trans (compare lanes 5 and 6, 7 and 8, 9 and 10, 11and 12, 5–6 and 11–12). The resistance of the expression of the codon optimized gag-pol to inhibition by LMB indicates that the exportin-1 pathway is not used and therefore an alternative export pathway must be used. This offers a possible explanation for the Rev independent expression. The fact that the presence of a nonfunctional Rev/RRE interaction did not affect expression implies that the RRE does not necessarily act as an inhibitory (e.g. nuclear retention) signal per se, which is in agreement with previous observations (58, 87). In conclusion, this is the first report of an HIV-1 based vector system, composed of pSYNGP, pHS3nZ and pHCMVG, where significant vector production can be achieved in the absence of all accessory proteins. These data indicate that in order to achieve maximum titres the HIV vector genome must be configured to retain efficient packaging and that this requires the retention of gag sequences and a splice donor. By reducing the gag sequence to 360 nt in pHS3nZ and combining this with pSYNGP it is possible to achieve titre of at least $10^5$ I.U./ml that is only 5-fold lower than the maximum levels achieved in the presence of Rev.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

REFERENCES

1. Bahner, I., K. Kearns, Q. L. Hao, E. M. Smogorzewska, and D. B. Kohn. 1996. Transduction of human CD34+ hematopoietic progenitor cells by a retroviral vector expressing an RRE decoy inhibits human immunodeficiency virus type 1 replication in myelomonocytic cells produced in long-term culture. J Virol. 70:4352–60.
2. Blomer, U., L. Naldini, T. Kafri, D. Trono, I. M. Verma, and F. H. Gage. 1997. Highly efficient and sustained gene transfer in adult neurons with a lentivirus vector. J Virol. 71:6641–6649.
3. Breaker, R. R. and Joyce, G. F. 1994. Inventing and improving ribozyme function: rational design versus interactive selection methods. TIBTECH. 12: 268–75.
4. Buchschacher, G. L., Jr., and A. T. Panganiban. 1992. Human immunodeficiency virus vectors for inducible expression of foreign genes. J Virol. 66:2731–2739.
5. Chen, C. J., A. C.:Banerjea, G. G. Harmison, K. Haglund, and M. Schubert. 1992. Multitarget-ribozyme directed to cleave at up to nine highly conserved HIV-1 env RNA regions inhibits HIV-1 replication-potential effectiveness against most presently sequenced HIV-1 isolates. Nucleic Acids Res. 20:4581–9.
6. Chesebro, B., K. Wehrly, and W. Maury. 1990. Differential expression in human and mouse cells of human immunodeficiency virus pseudotyped by murine retroviruses. J Virol. 64:4553–7.
7. Couture, L. A. and Stinchcomb, D. T. 1996. Anti-gene therapy: the use of ribozymes to inhibit gene function. TIG 12: 510–5.
8. Dropulic, B., M. Hermankova, and P. M. Pitha. 1996. A conditionally replicating HIV-1 vector interferes with wild-type HIV-1 replication and spread. Proc Natl Acad Sci USA. 93:11103–8.
9. Foecking, M. K., and H. Hofstetter. 1986. Powerful and versatile enhancer-promoter unit for manmmalian expression vectors. Gene. 45:101–105.
10. Gervaix, A., X. Li, G. Kraus, and F. Wong Staal. 1997. Multigene antiviral vectors inhibit diverse human immunodeficiency virus type 1 clades. J Virol. 71:3048–53.
11. Haas, J., E.-C. Park, and B. Seed. 1996. Codon usage limitation in the expression of HIV-1 envelope glycoprotein. Current Biology. 6:315.
12. Kim, V. N., K. Mitrophanous, S. M. Kingsman, and K. A. J. 1998. Minimal Requirement for a Lentiviral Vector Based on Human Immunodeficiency Virus Type 1. J Virol 72: 811–816.
13. Larsson, S., G. Hotchkiss, J. Su, T. Kebede, M. Andang, T. Nyholm, B. Johansson, A. Sonnerborg, A. Vahine, S. Britton, and L. Ahrlund Richter. 1996. A novel ribozyme target site located in the HIV-1 nef open reading frame. Virology. 219: 161
14. Lever, A. M. 1995. Gene therapy for HIV infection. Br Med Bull. 51:149–66.
15. Liu, D., J. Donegan, G. Nuovo, D. Mitra, and J. Laurence. 1997. Stable human immunodeficiency virus type 1 (HIV-1) resistance in transformed CD4+ monocytic cells treated with multitargeting HIV-1 antisense sequences incorporated into U1 snRNA. J Virol. 71:4079–85.
16. Malim, M. H., S. Bohnlein, J. Hauber, and B. R. Cullen. 1989. Functional dissection of the HIV-1 Rev transactivator-derivation of a trans-dominant repressor of Rev function. Cell. 58:205–14.
17. Miller, N., and J. Whelan. 1997. Progress in transcriptionally targeted and regulatable vectors for genetic therapy. Hum Gene Ther. 8:803–15.
18. Naldini, L., U. Blomer, F. H. Gage, D. Trono, and 1. M. Verma. 1996. Efficient transfer, integration, and sustained long-term expression of the transgene in adult rat brains injected with a lentiviral vector. Proc Natl Acad Sci USA. 93:11382–11388.
19. Naldini, L., U. Blomer, P. Gallay, D. Ory, R. Mulligan, F. H. Gage, 1. M. Verma, and D. Trono. 1996. In vivo gene delivery and stable transduction of nondividing cells by a lentiviral vector [see comments]. Science. 272:263–7.
20. Ory, D. S., B. A. Neugeboren, and R. C. Mulligan. 1996. A stable human-derived packaging cell line for production of high titer retrovirus/vesicular stomatitis virus G pseudotypes. Proc Natl Acad Sci USA. 93:11400–6.
21. Paik, S. Y., A. Banerjea, C. J. Chen, Z. Ye, G. G. Harmison, and M. Schubert. 1997. Defective HIV-1 provirus encoding a multitarget-ribozyme inhibits accumulation of spliced and unspliced HIV-1 mRNAs, reduces infectivity of viral progeny, and protects the cells from pathogenesis. Hum Gene Ther. 8:1115–24.
22. Poeschla, E., P. Corbeau, and F. Wong Staal. 1996. Development of HIV vectors for anti-HIV gene therapy. Proc Natl Acad Sci USA. 93:11395–9.
23. Poznansky, M., A. Lever, L. Bergeron, W. Haseltine, and J. Sodroski. 1991. Gene transfer into human lymphocytes by a defective human immunodeficiency virus type 1 vector. J Virol. 65:532–6.
24. Ramezani, A., and S. Joshi. 1996. Comparative analysis of five highly conserved target sites within the HIV-1 RNA for their susceptibility to hammerhead ribozyme-mediated cleavage in vitro and in vivo. Antisense Nucleic Acid Drug Dev. 6:229–35.
25. Riddell, S. R., M. Elliott, D. A. Lewinsohn, M. J. Gilbert, L. Wilson, S. A. Manley, S. D. Lupton, R. W. Overell, T. C. Reynolds, L. Corey, and P. D. Greenberg. 1996. T-cell mediated rejection of gene-modified HIVspecific cytotoxic T lymphocytes in HIV-infected patients [see comments]. Nat Med. 2:216–23.
26. Ruffner, D. E., S. C. Dahm, and O. C. Uhlenbeck. 1989. Studies on the hammerhead RNA self-cleaving domain. Gene. 82:31–41.
27. Sarver, N., E. M. Cantin, P. S. Chang, J. A. Zaia, P. A. Ladne, D. A. Stephens, and J. J. Rossi. 1990. Ribozymes as potential anti-HIV-1 therapeutic agents. Science. 247:1222.
28. Schneider, R., M. Campbell, G. Nasioulas, B. K. Felber, and G. N. Pavlakis. 1997. Inactivation of the human immunodeficiency virus type 1 inhibitory elements allows Rev-independent expression of Gag and Gag/protease and particle formation. J Virol. 71:4892–903.
29. Schwartz, S., M. Campbell, G. Nasioulas, J. Harrison, B. K. Felber, and G. N. Pavlakis.1992. Mutational inactivation of an inhibitory sequence in human immunodeficiency virus type 1 results in Rev-independent gag expression. J Virol. 66:7176–82.
30. Scott, W. G. and Klug, A. 1996. Ribozymes: structure and mechanism in RNA catalysis. TIBS. 21: 220–4.
31. Sczakiel, G., and M. Pawlita. 1991. Inhibition of human immunodeficiency virus type 1 replication in human T cells stably expressing antisense RNA. J Virol. 65:468–72.
32. Shimada, T., H. Fujii, H. Mitsuya, and A. W. Nienhuis. 1991. Targeted and highly efficient gene transfer into CD4+ cells by a recombinant human immunodeficiency virus retroviral vector. Journal of Clinical Investigation. 88:1043–47.
33. Soneoka, Y., P. M. Cannon, E. E. Ramsdale, J. C. Griffiths, G. Romano, S. M. Kingsman, and A. J. Kingsman. 1995. A transient threeplasmid expression system for the production of high titer retroviral vectors. Nucleic Acids Res. 23:628–33.
34. Spector, D. H., E. Wade, D. A. Wright, V. Koval, C. Clark, D. Jaquish, and S. A. Spector. 1990. Human immunodeficiency virus pseudotypes with expanded cellular and species tropism. J Virol. 64:2298–2308.
35. Srinivasakumar, N., N. Chazal, C. Helga Maria, S. Prasad, M. L. Hammarskjold, and D. Rekosh. 1997. The effect of viral regulatory protein expression on gene delivery by human immunodeficiency virus type 1 vectors produced in stable packaging cell lines. J Virol. 71:5841–8.
36. Sun, L. Q., L. Wang, W. L. Gerlach, and G. Symonds. 1995. Target sequence-speciEc inhibition of HIV-1 replication by ribozymes directed to tat RNA. Nucleic Acids Res. 23:2909–13.
37. Valsesia Wittmann, S., A. Drynda, G. Deleage, M. Aumailley, J. M. Heard, O. Danos, G. Verdier, and F. L. Cosset. 1994. Modifications in the binding domain of avian retrovirus envelope protein to redirect the host range of retroviral vectors. J Virol. 68:4609–19.
38. Yamada, O., G. Kraus, M. C. Leavitt, M. Yu, and F. Wong Staal. 1994. Activity and cleavage site specificity of an anti-HIV-1 hairpin ribozyme in human T cells. Virology. 205:121–6.
39. Yu, H., A. B. Rabson, M. Kaul, Y. Ron, and J. P. Dougherty. 1996. Inducible human immunodeficiency virus type 1 packaging cell lines. J Virol. 70:4530–37.
40. Zhou, C., I. Bahner, J. J. Rossi, and D. B. Kohn.1996. Expression of hammerhead ribozymes by retroviral vectors to inhibit HIV-1 replication: comparison of RNA levels and viral inhibition. Antisense Nucleic Acid Drug Dev. 6:17–24.
41. Zhu, Z. H., S. S. Chen, and A. S. Huang. 1990. Phenotypic mixing between human immunodeficiency virus and vesicular stomatitis virus or herpes simplex virus. J Acquir Immune Defic Syndr. 3:215–9.
42. Zolotukhin, S., M. Potter, W. W. Hauswirth, J. Guy, and N. Muzyczka. 1996. A "humanized" green fluorescent protein cDNA adapted for high-level expression in mammalian cells. J Virol. 70:4646–54.
43. Zufferey, R., D. Nagy, R. J. Mandel, L. Naldini, and D. Trono. 1997. Multiply attenuated lentiviral vector achieves efficient gene delivery in vivo. Nat Biotechnol. 15: 871–875.
44. Goodchild, J., V. Kohli. 1991. Ribozymes that cleave an RNA sequence from human immunodeficiency virus: the effect of flanking sequence on rate. Arch Biochem Biophys February 1; 284(2):386–391.
45. Hertel, Klemens J., Alessio PeracchI, Olke C. Uhlenbeck and Daniel Herschlag. 1997. Use of intrinsic binding energy for catalysis by an RNA enzyme. Proc. Natl. Acad. Sci. USA Vol. 94, pp. 8497–8502, August.
46. Bender et al., 1987, J Virol 61: 1639–1646
47. Pear et al., 1993, Proc Natl Acad Sci 90: 8392–8396

48. Cosset et al., 1995, J. Virol. 69: 7430–7436
49. Adachi, A., H. Gendelman, S. Koenig, T. Folks, R. Willey, A. Rabson, and M. Martin. 1986. Production of acquired immunodeficiency syndrome-associated retrovirus in human and non human cells transfected with an infectious molecular clone. J. Virol. 59:284–291.
50. Afonina, E., M. Neumann, and G. Pavlakis. 1997. Preferential binding of Poly(A)-binding protein I to an inhibitory RNA element in the HIV-1 gag mRNA. J. Biol. Chem. 272:2307–2311.
51. Andre, S., B. Seed, J. Eberle, W. Schraut, A. Bultmann, and J. Haas. 1998. Increased immune response elicited by DNA vaccination with a synthetic gp120 sequence with optimised codon usage. J. Virol. 72:1497–1503.
52. Arai, T., M. Takada, M. Ui, and H. Iba. 1999. Dose-dependent transduction of vesicular stomatitis virus G protein-pseudotyped retrovirus vector into human solid tumor cell lines and murine fibroblasts. Virology. 260:109–115.
53. Arrigo, S. J., and I. S. Chen. 1991. Rev is necessary for translation but not cytoplasmic accumulation of HIV-1 vif, vpr, and env/vpu 2 RNAs. Genes Dev. 5:808–19.
54. Barker, G., and K. Beemon. 1991. Nonsense codons within the RSV gag gene decrease the stability of unspliced viral RNA. Mol. Cell. Biol. 11:2760–2768.
55. Berg, O., and C. Kurland. 1997. Growth-rate optimised tRNA abundance and codon usage. J. Mol. Biol. 270:1705–1711.
56. Brighty, D., and M. Rosenberg. 1994. A cis-acting repressive sequence that overlaps the Rev responsive element of HIV-1 regulates nuclear retention of env mRNAs independently of known splice signals. Proc. Natl. Acad. Sci. USA. 91:8314–8318.
57. Cassan, M., N. Delaunay, C. Vaquero, and J. P. Rousset. 1994. Translational frameshifting at the gag-pol junction of human immunodeficiency virus type 1 is not increased in infected T-lymphoid cells. J. Virol. 68:1501–8.
58. Chang, D. D., and P. A. Sharp. 1989. Regulation by HIV Rev depends upon recognition of splice sites. Cell. 59:789–795.
59. Chang, L.-J., V. Urlacher, T. Iwakama, Y. Cui, and J. Zucali. 1999. Efficacy and safety analysis of a recombinant HIV-1 derived vector system. Gene Ther. 6:715–728.
60. Cimarelli, A., and J. Luban. 1999. Translation elongation factor 1-alpha interacts specifically with the human immunodeficiency virus type 1 Gag polyprotein. J. Virol. 73:5388–5401.
61. Cui, Y., T. Iwakama, and L.-J. Chang. 1999. Contribution of viral splice sites and cis regulatory elements to lentivirus vector function. J. Virol. 73:6171–6176.
62. D. Agostino, D. M., B. K. Felber, J. E. Harrison, and G. N. Pavlakis. 1992. The Rev protein of human immunodeficiency virus type 1 promotes polysomal association and translation of gag/pol and vpu/env mRNAs. Mol. Cell. Biol. 12:1375–86.
63. DuBridge, R. B., P. Tang, H. C. Hsia, P.-M. Leong, J. H. Miller, and M. P. Calos. 1987. Analysis of mutation in human cells by using an Epstein-Barr virus shuttle system. Mol. Cell. Biol. 7:379–387.
64. Dull, T., R. Zufferey, M. Kelly, R. Mandel, M. Nguyen, D. Trono, and L. Naldini. 1998. A third generation lentivirus vector with a conditional packaging system. J. Virol. 72:8463–8471.
65. Favaro, J., F. Maldarelli, S. Arrigo, and M. Schmidt. 1999. Effect of Rev on the cytoplasmic localization of intron-containing HIV-1 RNA. Virology. 255:237–249.
66. Felber, B. K., M. Hadzopoulou Cladaras, C. Cladaras, T. Copeland, and G. N. Pavlakis. 1989. Rev protein of human immunodeficiency virus type 1 affects the stability and transport of the viral messenger RNA. Proc. Natl. Acad. Sci. USA.. 86:1495–1499.
67. Fisher, A., E. Collalti, L. Ratner, R. Gallo, and F. Wong-Staal. 1985. A molecular clone of HTLV-III with biological activity. Nature. 316:262–265.
68. Fornerod, M., M. Ohno, M. Yoshida, and I. W. Mattaj. 1997. CRM1 is an export receptor for leucine-rich nuclear export signals. Cell. 90:1051–1060.
69. Fridell, R. A., H. P. Bogerd, and B. R. Cullen. 1996. Nuclear export of late HIV-1 mRNAs occurs via a cellular protein export pathway. Proc. Natl. Acad. Sci. USA. 93:4421–4.
70. Gasmi, M., J. Glynn, M.-J. Jin, D. Jolly, J.-K. Yee, and S.-T. Chen. 1999. Requirements for efficient production and transduction of Human Immunodeficiency Virus Type 1-based vectors. J. Virol. 73:1828–1834.
71. Gey, G. O., W. D. Coffman, and M. T. Kubicek. 1952. Cancer res. 12:264.
72. Hadzopoulou Cladaras, M., B. K. Felber, C. Cladaras, A. Athanassopoulos, A. Tse, and G. N. Pavlakis. 1989. The rev (trs/art) protein of human immunodeficiency virus type 1 affects viral mRNA and protein expression via a cis-acting sequence in the env region. J. Virol. 63:1265–74.
73. Harrison, G., G. Miele, E. Hunter, and A. Lever. 1998. Functional analysis of the core human immunodeficiency virus type 1 packaging signal in a permissive cell line. J. Virol. 72:5886–5896.
74. Hentze, M., and A. Kulozik. 1999. A perfect message: RNA surveillance and nonsense-mediated decay. Cell. 96:307–310.
75. Huang, Y., and G. Carmichael. 1997. The mouse histone H2a gene contains a small element that facilitates cytoplasmic accumulation of intronless gene transcripts and of unspliced HIV-1 related mRNAs. Proc. Natl. Acad. Sci. USA. 94:10104–10109.
76. Jacks, T., M. D. Power, F. R. Masiarz, P. A. Luciw, P. J. Barr, and H. E. Varmus. 1988. Characterization of ribosomal frameshifting in HIV-1 gag-pol expression. Nature. 331:280–3.
77. Kim, S. Y., R. Byrn, J. Groopman, and D. Baltimore. 1989. Temporal aspects of DNA and RNA synthesis during human immunodeficiency virus infection: evidence for differential gene expression. J. Virol. 63:3708–3713.
78. Kozak, M. 1992. Regulation of translation in eukaryotic systems. [Review]. Annu. Rev. Cell Biol. 8:197–225.
79. Kypr, J., and J. Mrazek. 1987. Unusual codon usage of HIV. Nature. 327:20.
80. Kypr, J., J. Mrazek, and J. Reich. 1989. Nucleotide composition bias and CpG dinucleotide content in the genomes of HIV and HTLV 1 and 2. Biochim. Biophys. Acta. 1009:280–282.
81. Lever, A., H. Gottlinger, W. Haseltine, and J. Sodroski. 1989. Identification of a sequence required for efficient packaging of human immunodeficiency virus type 1 RNA into virions. J. Virol. 63:4085–7.
82. Maldarelli, F., M. A. Martin, and K. Strebel. 1991. Identification of posttranscriptionally active inhibitory sequences in human immunodeficiency virus type 1 RNA: novel level of gene regulation. J. Virol. 65:5732–5743.
83. Malim, M. H., and B. R. Cullen. 1993. Rev and the fate of pre-mRNA in the nucleus: implications for the regulation of RNA processing in eukaryotes. Mol. Cell. Biol. 13:6180–89.

84. Malim, M. H., J. Hauber, S. Y. Le, J. V. Maizel, and B. R. Cullen. 1989. The HIV-1 rev trans-activator acts through a structured target sequence to activate nuclear export of unspliced viral mRNA. Nature. 338:254–7.
85. Maurer, F., M. Tierney, and R. Medcalff. 1999. An AU-rich sequence in the 3' UTR of PAI-2 mRNA promotes PAI-2 mRNA decay and provides a binding site for nuclear HuR. Nucl. Acids Res. 27:1664–1673.
86. McBride, M. S., and A. T. Panganiban. 1997. Position dependence of functional hairpins important for human immunodeficiency virus type 1 RNA encapsidation in vivo. J. Virol. 71:2050–8.
87. Mikaelian, I., M. Krieg, M. Gait, and J. Karn. 1996. Interactions of INS (CRS) elements and the splicing machinery regulate the production of Rev-responsive mRNAs. J. Mol. Biol. 257:246–264.
88. Naldini, L. 1998. Lentiviruses as gene transfer agents for delivery to non-dividing cells. Curr. Opin. Biotechnol. 9:457–463.
89. Nasioulas, G., A. S. Zolotukhin, C. Tabernero, L. Solomin, C. P. Cunningham, G. N. Pavlakis, and B. K. Felber. 1994. Elements distinct from human immunodeficiency virus type 1 splice sites are responsible for the Rev dependence of env mRNA. J. Virol. 68:2986–93.
90. Olsen, H., A. Cochrane, and C. Rosen. 1992. Interaction of cellular factors with intragenic cis-acting repressive sequences within the HIV genome. Virology. 191:709–715.
91. Otero, G. C., M. E. Harris, J. E. Donello, and T. J. Hope. 1998. Leptomycin B inhibits equine infectious anemia virus rev and feline immunodeficiency virus rev function but not the function of the hepatitis B virus posttranscriptional regulatory element. J. Virol. 72:7593–7597.
92. Parkin, N. T., M. Chamorro, and H. E. Varmus. 1992. Human immunodeficiency virus type 1 gag-pol frameshifting is dependent on downstream mRNA secondary structure: demonstration by expression in vivo. J. Virol. 66:5147–51.
93. Parolin, C., T. Dorfman, G. Palu, H. Gottlinger, and J. Sodroski. 1994. Analysis in human immunodeficiency virus type 1 vectors of cis- acting sequences that affect gene transfer into human lymphocytes. J. Virol. 68:3888–3895.
94. Pollard, V., and M. Malim. 1998. The HIV-1 Rev protein. Annu. Rev. Microbiol. 52:491–532.
95. Qiu, J.-T., R. Song, M. Dettenhofer, C. Tian, T. August, B. Felber, G. Pavlakis, and X.-F. Yu. 1999. Evaluation of novel Human Immunodeficiency Virus Type 1 Gag DNA vaccines for protein expression in mammalian cells and induction of immune responses. J. Virol. 73:9145–9152.
96. Rabbits, P., A. Forster, M. Stinson, and T. Rabbits. 1985. Truncation of exon 1 from the c-myc gene results in prolongued c-my mRNA stability. EMBO J. 4:3727–3733.
97. Rouwendal, G. J., O. Mendes, E. J. Wolbert, and A. Douwe de Boer. 1997. Enhanced expression in tobacco of the gene encoding green fluorescent protein by modification of its codon usage. Plant Mol. Biol. 33:989–99.
98. Sagerstrom, C., and H. Sive. 1996. RNA blot analysis, p. 83–104. In P. Krieg (ed.), A laboratory guide to RNA: isolation, analysis and synthesis, vol. 1. Wiley-Liss Inc., New York.
99. Schwartz, S., B. K. Felber, and G. N. Pavlakis. 1992. Distinct RNA sequences in the gag region of human immunodeficiency virus type 1 decrease RNA stability and inhibit expression in the absence of Rev protein. J. Virol. 66:150–159.
100. Sharp, P. M. 1986. What can AIDS virus codon usage tell us? . Nature. 324:114.
101. Sostengard, T., and P. Hackett. 1996. Autogenous regulation of RNA translation and packaging by Rous Sarcoma Virus Pr76Gag. J. Virol. 70:6642–6652.
102. Stade, K., C. S. Ford, C. Guthrie, and K. Weis. 1997. Exportin 1 (Crm1p) is an essential nuclear export factor. Cell. 90:1041–1050.
103. Ullman, K. S., M. Powers, A, and D. J. Forbes. 1997. Nuclear export receptors: from importin to exportin. Cell. 90:967–970.
104. Van Hemert, F. J., and B. Berkhout. 1995. The Tendency of Lentiviral Open Reading Frames to Become A-Rich: Constraints Imposed by Viral Genome Organization and Cellular tRNA Availability. J. Mol. Evol. 41:132–140.
105. Varenne, S., J. Buc, R. Lloubes, and C. Lazdunski. 1984. Translation is a nonuniform process: Effect of transfer RNA availability on the rate of elongation of nascent polypeptide chains. J. Mol. Biol. 180:549–576.
106. Verma, I. M., and N. Somia. 1997. Gene therapy—promises, problems and prospects [news]. Nature. 389:239–42.
107. Wilson, S., C. Sieiro-Vasquez, N. Edwards, O. Iourin, E. Byles, E. Kotsopoulou, C. Adamson, S. Kingsman, A. Kingsman, and E. Martin-Rendon. 1999. Cloning and characterisation of hIF2, a human homologue of bacterial translation initiation factor 2, and its interaction with HIV-1 matrix. Biochem. J. 342:97–103.
108. Wilson, W., M. Braddock, S. E. Adams, P. D. Rathjen, S. M. Kingsman, and A. J. Kingsman. 1988. HIV expression strategies: ribosomal frameshifting is directed by a short sequence in both mammalian and yeast systems. Cell. 55:1159–69.
109. Wisdom, R., and W. Lee. 1991. The protein coding region of c-myc mRNA contains a sequence that specifies rapid mRNA turnover and induction by protein synthesis inhibitors. Genes Dev. 5:232–243.
110. Wolff, B., J.-J. Sanglier, and Y. Wang. 1997. Leptomycin B is an inhibitor of nuclear export: inhibition of nucleocytoplasmic translocation of the HIV-1 Rev protein and Rev-dependent mRNA. Chem. Biol. 4:139–147.
111. Xu, N., C.-Y. Chen, and A.-B. Shyu. 1997. Modulation of the fate of cytoplasmic mRNA by AU-rich elements: Key sequence features controlling mRNA deadenylation and decay. Mol. Cell. Biol. 17:4611–4621.
112. Yang, T. T., L. Cheng, and S. R. Kain. 1996. Optimized codon usage and chromophore mutations provide enhanced sensitivity with the green fluorescent protein. Nucl. Acids Res. 24:4592–3.
113. Yee, J. K., A. Miyanohara, P. LaPorte, K. Bouic, J. C. Burns, and T. Friedmann. 1994. A general method for the generation of high-titer, pantropic retroviral vectors: highly efficient infection of primary hepatocytes. Proc. Natl. Acad. Sci. USA. 91:9564–8.
114. Zolotukhin, A. S., A. Valentin, G. N. Pavlakis, and B. K. Felber. 1994. Continuous propagation of RRE(–) and Rev(–)RRE(–) human immunodeficiency virus type 1 molecular clones containing a cis-acting element of simian retrovirus type 1 in human peripheral blood lymphocytes. J. Virol. 68:7944–52.

What is claimed is:

1. A lentiviral vector system comprising:
   (i) a lentiviral vector genome comprising at least one first nucleotide sequence encoding an anti-sense ribonucleic acid or a ribozyme, wherein said sequence is capable of binding to and effecting the cleavage of a second nucleotide sequence, or transcription product thereof, said second nucleotide sequence encoding a lentiviral polypeptide required for the assembly of lentiviral particles; and
   (ii) at least one third nucleotide sequence encoding said lentiviral polypeptide required for the assembly of the lentiviral genome into viral particles, which at least one third nucleotide sequence has a different nucleotide sequence to the second nucleotide sequence such that said third nucleotide sequence, or transcription sequence, or transcription product thereof, is codon-optimized and resistant to cleavage directed by said anti-sense ribonucleic acid or said ribozyme.

2. The system according to claim 1 comprising a plurality of first nucleotide sequences and third nucleotide sequences as defined therein.

3. The system according to claim 1 wherein the lentiviral vector genome is an HIV vector genome.

4. The system according to claim 1 wherein the polypeptide required for the assembly of viral particles is selected from gag, pol and env proteins, wherein at least said gag and pol proteins are from a lentivirus.

5. The system according to claim 1 wherein the polypeptide required for the assembly of viral particles is selected from lentiviral gag, pol and env proteins.

6. The system according to claim 1 wherein the at least one third nucleotide sequence is resistant to cleavage directed by said anti-sense ribonucleic acid or said ribozyme as a result of one or more conservative alterations in the nucleotide sequence which remove cleavage sites recognized by said anti-sense ribonucleic acid or said ribozyme.

7. The system according to claim 1 wherein the at least one third nucleotide sequence is codon optimized for expression in producer cells.

8. The system according to claim 1, wherein the at least one third nucleotide sequence is codon optimized for expression in producer cells and wherein said producer cells are mammalian cells.

9. A lentiviral particle comprising the lentiviral vector genome as defined in claim 1 and the one or more third nucleotide sequences as defined in claim 1.

10. A method for producing a lentiviral particle which method comprises introducing into a host cell (i) the lentiviral genome as defined in claim 1, (ii) the one or more third nucleotide sequences as defined in claim 1 and (iii) nucleotide sequences encoding the other essential viral packaging components not encoded by the one or more third nucleotide sequences.

* * * * *

UNITED STATES PATENT AND TRADEMARK OFFICE
CERTIFICATE OF CORRECTION

PATENT NO. : 6,541,248 B1
DATED : April 1, 2003
INVENTOR(S) : Kingsman et al.

It is certified that error appears in the above-identified patent and that said Letters Patent is hereby corrected as shown below:

Title page,
Item [30], Foreign Application Priority Data,
"Feb. 17, 1998 (GB)………………....9803352" should read
-- Feb. 17, 1998 (GB)………………....9803351.7 --.

Signed and Sealed this

Ninth Day of March, 2004

JON W. DUDAS
*Acting Director of the United States Patent and Trademark Office*

SEQUENCE LISTING

<160> NUMBER OF SEQ ID NOS: 22

<210> SEQ ID NO 1
<211> LENGTH: 4307
<212> TYPE: DNA
<213> ORGANISM: Human immunodeficiency virus

<400> SEQUENCE: 1

| | | | | | |
|---|---|---|---|---|---|
| atgggtgcga | gagcgtcagt | attaagcggg | ggagaattag | atcgatggga | aaaaattcgg | 60 |
| ttaaggccag | ggggaaagaa | aaatataaa | ttaaaacata | tagtatgggc | aagcagggag | 120 |
| ctagaacgat | tcgcagttaa | tcctggcctg | ttagaaacat | cagaaggctg | tagacaaata | 180 |
| ctgggacagc | tacaaccatc | ccttcagaca | ggatcagaag | aacttagatc | attatataat | 240 |
| acagtagcaa | ccctctattg | tgtgcatcaa | aggatagaga | taaaagacac | caaggaagct | 300 |
| ttagacaaga | tagaggaaga | gcaaaacaaa | agtaagaaaa | agcacagca | agcagcagct | 360 |
| gacacaggac | acagcaatca | ggtcagccaa | aattacccta | tagtgcagaa | catccagggg | 420 |
| caaatggtac | atcaggccat | atcacctaga | actttaaatg | catgggtaaa | agtagtagaa | 480 |
| gagaaggctt | tcagcccaga | agtgatacc | atgttttcag | cattatcaga | aggagccacc | 540 |
| ccacaagatt | taaacaccat | gctaaacaca | gtggggggac | atcaagcagc | catgcaaatg | 600 |
| ttaaaagaga | ccatcaatga | ggaagctgca | gaatgggata | gagtgcatcc | agtgcatgca | 660 |
| gggcctattg | caccaggcca | gatgagagaa | ccaagggaa | gtgacatagc | aggaactact | 720 |
| agtacccttc | aggaacaaat | aggatggatg | acaaataatc | cacctatccc | agtaggagaa | 780 |
| atttataaaa | gatggataat | cctgggatta | aataaaatag | taagaatgta | tagccctacc | 840 |
| agcattctgg | acataagaca | aggaccaaag | gaacccttta | gagactatgt | agaccggttc | 900 |
| tataaaactc | taagagccga | gcaagcttca | caggaggtaa | aaaattggat | gacagaaacc | 960 |
| ttgttggtcc | aaaatgcgaa | cccagattgt | aagactattt | taaaagcatt | gggaccagcg | 1020 |
| gctacactag | aagaaatgat | gacagcatgt | cagggagtag | gaggacccgg | ccataaggca | 1080 |
| agagttttgg | ctgaagcaat | gagccaagta | acaaattcag | ctaccataat | gatgcagaga | 1140 |
| ggcaatttta | ggaaccaaag | aaagattgtt | aagtgtttca | attgtggcaa | agaagggcac | 1200 |
| acagccagaa | attgcagggc | ccctaggaaa | aagggctgtt | ggaaatgtgg | aaggaagga | 1260 |
| caccaaatga | aagattgtac | tgagagacag | gctaattttt | tagggaagat | ctggccttcc | 1320 |
| tacaagggaa | ggccagggaa | ttttcttcag | agcagaccag | agccaacagc | cccaccagaa | 1380 |
| gagagcttca | ggtctggggt | agagacaaca | actccccctc | agaagcagga | gccgatagac | 1440 |
| aaggaactgt | atcctttaac | ttccctcagg | tcactctttg | gcaacgaccc | ctcgtcacaa | 1500 |
| taaagatagg | ggggcaacta | aaggaagctc | tattagatac | aggagcagat | gatacagtat | 1560 |
| tagaagaaat | gagtttgcca | ggaagatgga | aaccaaaaat | gatagggga | attggaggtt | 1620 |
| ttatcaaagt | aagacagtat | gatcagatac | tcatagaaat | ctgtggacat | aaagctatag | 1680 |
| gtacagtatt | agtaggacct | acacctgtca | acataattgg | aagaaatctg | ttgactcaga | 1740 |
| ttggttgcac | tttaaatttt | cccattagcc | ctattgagac | tgtaccagta | aaattaaagc | 1800 |
| caggaatgga | tggcccaaaa | gttaaacaat | ggccattgac | agaagaaaaa | ataaaagcat | 1860 |
| tagtagaaat | ttgtacagag | atggaaaagg | aagggaaaat | ttcaaaaatt | gggcctgaaa | 1920 |
| atccatacaa | tactccagta | tttgccataa | agaaaaaaga | cagtactaaa | tggagaaaat | 1980 |
| tagtagattt | cagagaactt | aataagagaa | ctcaagactt | ctgggaagtt | caattaggaa | 2040 |

-continued

```
taccacatcc cgcagggtta aaaaagaaaa aatcagtaac agtactggat gtgggtgatg    2100 catattttc agttcccctta gatgaagact tcaggaagta tactgcattt accataccta    2160
gtataaacaa tgagacacca gggattagat atcagtacaa tgtgcttcca cagggatgga    2220
aaggatcacc agcaatattc caaagtagca tgacaaaaat cttagagcct tttagaaaac    2280
aaaatccaga catagttatc tatcaataca tggatgattt gtatgtagga tctgacttag    2340 aaataggca gcatagaaca aaaatagagg agctgagaca acatctgttg aggtggggac    2400
ttaccacacc agacaaaaaa catcagaaag aacctccatt cctttggatg ggttatgaac    2460
tccatcctga taaatggaca gtacagccta tagtgctgcc agaaaaagac agctggactg    2520
tcaatgacat acagaagtta gtggggaaat tgaattgggc aagtcagatt tacccaggga    2580
ttaaagtaag gcaattatgt aaactcctta gaggaaccaa agcactaaca gaagtaatac    2640
cactaacaga agaagcagag ctagaactgg cagaaaacag agagattcta aaagaaccag    2700
tacatggagt gtattatgac ccatcaaaag acttaatagc agaaatacag aagcaggggc    2760
aaggccaatg gacatatcaa atttatcaag agccatttaa aaatctgaaa acaggaaaat    2820
atgcaagaat gaggggtgcc cacactaatg atgtaaaaca attaacagag gcagtgcaaa    2880
aaataaccac agaaagcata gtaatatggg gaaagactcc taaatttaaa ctgcccatac    2940
aaaaggaaac atgggaaaca tggtggacag agtattggca agccacctgg attcctgagt    3000
gggagtttgt taatacccct cccttagtga aattatggta ccagttagag aaagaaccca    3060
tagtaggagc agaaaccttc tatgtagatg gggcagctaa cagggagact aaattaggaa    3120
aagcaggata tgttactaat agaggaagac aaaaagttgt caccctaact gacacaacaa    3180
atcagaagac tgagttacaa gcaatttatc tagctttgca ggattcggga ttagaagtaa    3240
acatagtaac agactcacaa tatgcattag gaatcattca agcacaacca gatcaaagtg    3300
aatcagagtt agtcaatcaa ataatagagc agttaataaa aaaggaaaag gtctatctgg    3360
catgggtacc agcacacaaa ggaattggag gaaatgaaca agtagataaa ttagtcagtg    3420
ctggaatcag gaaagtacta tttttagatg gaatagataa ggcccaagat gaacatgaga    3480
aatatcacag taattggaga gcaatggcta gtgattttaa cctgccacct gtagtagcaa    3540
aagaaatagt agccagctgt gataaatgtc agctaaaagg agaagccatg catggacaag    3600
tagactgtag tccaggaata tggcaactag attgtacaca tttagaagga aaagttatcc    3660
tggtagcagt tcatgtagcc agtggatata tagaagcaga agttattcca gcagaaacag    3720
ggcaggaaac agcatatttt ctttttaaaat tagcaggaag atggccagta aaaacaatac    3780
atactgacaa tggcagcaat ttcaccggtg ctacggttag ggccgcctgt tggtgggcgg    3840
gaatcaagca ggaatttgga attccctaca atccccaaag tcaaggagta gtagaatcta    3900
tgaataaaga attaagaaa attataggac aggtaagaga tcaggctgaa catcttaaga    3960
cagcagtaca aatggcagta ttcatccaca attttaaaag aaaagggggg attgggggt    4020 acagtgcagg ggaaagaata gtagacataa tagcaacaga catacaaact aaagaattac    4080
aaaaacaaat tacaaaaatt caaaattttc gggtttatta cagggacagc agaaattcac    4140
tttggaaagg accagcaaag ctcctctgga aaggtgaagg ggcagtagta atacaagata    4200
atagtgacat aaaagtagtg ccaagaagaa aagcaaagat cattagggat tatggaaaac    4260
agatggcagg tgatgattgt gtggcaagta gacaggatga ggattag          4307
```

<210> SEQ ID NO 2

<211> LENGTH: 4307
<212> TYPE: DNA
<213> ORGANISM: Artificial Sequence
<220> FEATURE:
<223> OTHER INFORMATION: Description of Artificial Sequence:
      gagpol-SYNgp - codon optimised gagpol sequence

<400> SEQUENCE: 2

```
atgggcgccc gcgccagcgt gctgtcgggc ggcgagctgg accgctggga gaagatccgc     60
ctgcgccccg gcggcaaaaa gaagtacaag ctgaagcaca tcgtgtgggc cagccgcgaa    120
ctggagcgct tcgccgtgaa ccccgggctc ctggagacca gcgaggggtg ccgccagatc    180
ctcggccaac tgcagcccag cctgcaaacc ggcagcgagg agctgcgcag cctgtacaac    240
accgtggcca cgctgtactg cgtccaccag cgcatcgaaa tcaaggatac gaagaggcc    300
ctggataaaa tcgaagagga acagaataag agcaaaaaga aggcccaaca ggccgccgcg    360
gacaccggac acagcaacca ggtcagccag aactacccca tcgtgcagaa catccagggg    420
cagatggtgc accaggccat ctccccccgc acgctgaacg cctgggtgaa ggtggtggaa    480
gagaaggctt ttagcccgga ggtgataccc atgttctcag ccctgtcaga gggagccacc    540
ccccaagatc tgaacaccat gctcaacaca gtggggggac caggccgc catgcagatg      600
ctgaaggaga ccatcaatga ggaggctgcc gaatgggatc gtgtgcatcc ggtgcacgca    660
gggcccatcg caccgggcca gatgcgtgag ccacgggct cagacatcgc cggaacgact     720
agtacccttc aggaacagat cggctggatg accaacaacc cacccatccc ggtgggagaa    780
atctacaaac gctggatcat cctgggcctg aacaagatcg tgcgcatgta tagccctacc    840
agcatcctgg acatccgcca aggcccgaag gaacccttc gcgactacgt ggaccggttc     900
tacaaaacgc tccgcgccga gcaggctagc caggaggtga agaactggat gaccgaaacc    960
ctgctggtcc agaacgcgaa cccggactgc aagacgatcc tgaaggccct gggcccagcg   1020
gctaccctag aggaaatgat gaccgcctgt cagggagtgg gcggacccgg ccacaaggca   1080
cgcgtcctgg ctgaggccat gagccaggtg accaactccg ctaccatcat gatgcagcgc   1140
ggcaactttc ggaaccaacg caagatcgtc aagtgcttca ctgtggcaa agaagggcac    1200
acagcccgca actgcagggc cctaggaaaa agggctgct ggaaatgcgg caaggaaggc    1260
caccagatga aagactgtac ggagagacag gctaatttt tagggaagat ctggccttcc    1320
tacaagggaa ggccagggaa ttttcttcag agcagacccg cgccaacagc cccacccgcc   1380
gcgagcttca ggtctgggt cgcgacaaca actcccccctc gaagcagga gccgaccgcc    1440
agggcacggt gtccttcaac ttccctcagg tcacgctttg gcagcgaccc ctcgtcacca   1500
tcaagatcgg ggggcagctc aaggaggctc tcctggacac cggagcagac gacaccgtgc   1560
tggaggagat gtcgttgcca ggccgctgga gccgaagat gatcggggga atcggcggtt    1620
tcatcaaggt gcgccagtat gaccagatcc tcatcgaaat ctgcgggccac aaggctatcg   1680
gtaccgtgct ggtgggccc acacccgtca acatcatcgg acgcaacctg ttgacgcaga    1740
tcggttgcac gctgaacttc cccattagcc ctatcgagac ggtaccggtg aagctgaagc   1800
ccgggatgga cggcccgaag gtcaagcaat ggccattgac agaggagaag atcaaggcac    1860
tggtggagat ttgcacagag atggaaaagg aagggaaaat ctccaagatt gggcctgaga   1920
acccgtacaa cacgccggtg ttcgcaatca agaagaagga ctcgacgaaa tggcgcaagc   1980
tggtggactt ccgcgagctg aacaagcgca cgcaagactt ctgggaggtt cagctgggca   2040
tcccgcaccc cgcagggctg aagaagaaga atccgtgac cgtactggat gtgggtgatg   2100
```

-continued

```
cctacttctc cgttcccctg gacgaagact tcaggaagta cactgccttc acaatccctt     2160
cgatcaacaa cgagacaccg gggattcgat atcagtacaa cgtgctgccc cagggctgga     2220
aaggctctcc cgcaatcttc cagagtagca tgaccaaaat cctggagcct ttccgcaaac     2280
agaaccccga catcgtcatc tatcagtaca tggatgactt gtacgtgggc tctgatctag     2340
agatagggca gcaccgcacc aagatcgagg agctgcgcca gcacctgttg aggtggggac     2400
tgaccacacc cgacaagaag caccagaagg agcctccctt cctctggatg ggttacgagc     2460
tgcaccctga caaatggacc gtgcagccta tcgtgctgcc agagaaagac agctggactg     2520
tcaacgacat acagaagctg gtggggaagt tgaactgggc cagtcagatt tacccaggga     2580
ttaaggtgag gcagctgtgc aaactcctcc gcggaaccaa ggcactcaca gaggtgatcc     2640
ccctaaccga ggaggccgag ctcgaactgg cagaaaaccg agagatccta aaggagcccg     2700
tgcacggcgt gtactatgac ccctccaagg acctgatcgc cgagatccag aagcaggggc     2760
aaggccagtg gacctatcag atttaccagg agcccttcaa gaacctgaag accggcaagt     2820
acgcccggat gaggggtgcc cacactaacg acgtcaagca gctgaccgag gccgtgcaga     2880
agatcaccac cgaaagcatc gtgatctggg gaaagactcc taagttcaag ctgcccatcc     2940
agaaggaaac ctgggaaacc tggtggacag agtattggca ggccacctgg attcctgagt     3000
gggagttcgt caacacccct cccctggtga agctgtggta ccagctggag aaggagccca     3060
tagtgggcgc cgaaaccttc tacgtggatg gggccgctaa cagggagact aagctgggca     3120
aagccggata cgtcactaac cggggcagac agaaggttgt caccctcact gacaccacca     3180
accagaagac tgagctgcag gccatttacc tcgctttgca ggactcgggc ctggaggtga     3240
acatcgtgac agactctcag tatgccctgg gcatcattca agcccagcca gaccagagtg     3300
agtccgagct ggtcaatcag atcatcgagc agctgatcaa gaaggaaaag gtctatctgg     3360
cctgggtacc cgcccacaaa ggcattgcg gcaatgagca ggtcgacaag ctggtctcgg     3420
ctggcatcag gaaggtgcta ttcctggatg gcatcgacaa ggcccaggac gagcacgaga     3480
aataccacag caactggcgg gccatggcta gcgacttcaa cctgcccct gtggtggcca     3540 aagagatcgt ggccagctgt gacaagtgtc agctcaaggg cgaagccatg catggccagg     3600
tggactgtag ccccggcatc tggcaactcg attgcaccca tctggagggc aaggttatcc     3660
tggtagccgt ccatgtggcc agtggctaca tcgaggccga ggtcattccc gccgaaacag     3720
ggcaggagac agcctacttc ctcctgaagc tggcaggcc gtggcagtg aagaccatcc     3780 atactgacaa tggcagcaat ttcaccggtg ctacggttag ggccgcctgc tggtgggcgg     3840
gaatcaagca ggagttcggg atcccctaca atccccagag tcagggcgtc gtcgagtcta     3900
tgaataagga gttaaagaag attatcggcc aggtcagaga tcaggctgag catctcaaga     3960
ccgcggtcca aatggcggta ttcatccaca atttcaagcg gaagggggg attgggggt     4020 acagtgcggg ggagcggatc gtggacatca tcgcgaccga catccagact aaggagctgc     4080
aaaagcagat taccagatt cagaatttcc gggtctacta cagggacagc agaaattccc     4140
tctggaaagg cccagcgaag ctcctctgga agggtgaggg ggcagtagtg atccaggata     4200
atagcgacat caaggtggtg cccagaagaa aggcgaagat cattagggat tatggcaaac     4260
agatggcggg tgatgattgc gtggcgagca gacaggatga ggattag                  4307
```

<210> SEQ ID NO 3
<211> LENGTH: 2571
<212> TYPE: DNA
<213> ORGANISM: Human immunodeficiency virus type 1

<400> SEQUENCE: 3

```
atgagagtga aggggatcag gaggaattat cagcactggt ggggatgggg cacgatgctc      60
cttgggttat taatgatctg tagtgctaca gaaaaattgt gggtcacagt ctattatggg     120
gtacctgtgt ggaaagaagc aaccaccact ctattttgtg catcagatgc taaagcatat     180
gatacagagg tacataatgt ttgggccaca caagcctgtg tacccacaga ccccaaccca     240
caagaagtag aattggtaaa tgtgacagaa aattttaaca tgtggaaaaa taacatggta     300
gaacagatgc atgaggatat aatcagttta tgggatcaaa gcctaaagcc atgtgtaaaa     360
ttaaccccac tctgtgttac tttaaattgc actgatttga ggaatactac taataccaat     420
aatagtactg ctaataacaa tagtaatagc gagggaacaa taagggagg agaaatgaaa      480
aactgctctt tcaatatcac cacaagcata agagataaga tgcagaaaga atatgcactt     540
ctttataaac ttgatatagt atcaatagat aatgatagta ccagctatag gttgataagt     600
tgtaatacct cagtcattac acaagcttgt ccaaagatat cctttgagcc aattcccata     660
cactattgtg ccccggctgg ttttgcgatt ctaaaatgta acgataaaaa gttcagtgga     720
aaaggatcat gtaaaaatgt cagcacagta caatgtacac atggaattag ccagtagta     780
tcaactcaac tgctgttaaa tggcagtcta gcagaagaag aggtagtaat tagatctgag     840
aatttcactg ataatgctaa aaccatcata gtacatctga tgaatctgt acaaattaat      900
tgtacaagac ccaactacaa taaagaaaa aggatacata taggaccagg agagcatt       960
tatacaacaa aaatataat aggaactata agacaagcac attgtaacat tagtagagca    1020
aaatggaatg acactttaag acagatagtt agcaaattaa agaacaatt taagaataaa    1080
acaatagtct ttaatcaatc ctcaggaggg gacccagaaa ttgtaatgca cagttttaat    1140
tgtggagggg aattttttcta ctgtaataca tcaccactgt ttaatagtac ttggaatggt    1200
aataatactt ggaataatac tacagggtca aataacaata tcacacttca atgcaaaata    1260
aaacaaatta taaacatgtg gcaggaagta ggaaaagcaa tgtatgcccc tcccattgaa    1320
ggacaaatta gatgttcatc aaatattaca gggctactat taacaagaga tggtggtaag    1380
gacacggaca cgaacgacac cgagatcttc agacctggag gaggagatat gagggacaat    1440
tggagaagtg aattatataa atataaagta gtaacaattg aaccattagg agtagcaccc    1500
accaaggcaa agagaagagt ggtgcagaga gaaaaaagag cagcgatagg agctctgttc    1560
cttgggttct taggagcagc aggaagcact atgggcgcag cgtcagtgac gctgacggta    1620
caggccagac tattattgtc tggtatagtg caacagcaga acaatttgct gagggccatt    1680
gaggcgcaac agcatatgtt gcaactcaca gtctggggca tcaagcagct ccaggcaaga    1740
gtcctggctg tggaaagata cctaaaggat caacagctcc tggggttttg gggttgctct    1800
ggaaaactca tttgcaccac tactgtgcct tggaatgcta gttggagtaa taatctctg    1860
gatgatattt ggaataacat gacctggatg cagtgggaaa gagaaattga caattacaca    1920
agcttaatat actcattact agaaaaatcg caaacccaac aagaaaagaa tgaacaagaa    1980
ttattggaat tggataaatg gcaagtttg tggaattggt ttgacataac aaattggctg     2040
tggtatataa aaatattcat aatgatagta ggaggcttgg taggtttaag aatagttttt    2100
gctgtacttt ctatagtgaa tagagttagg cagggatact caccattgtc gttgcagacc    2160
cgccccccag ttccgagggg acccgacagg cccgaaggaa tcgaagaaga aggtggagag    2220
agagacagag acacatccgg tcgattagtg catggattct tagcaattat ctgggtcgac    2280
```

-continued

| | |
|---|---|
| ctgcggagcc tgttcctctt cagctaccac cacagagact tactcttgat tgcagcgagg | 2340 |
| attgtggaac ttctgggacg cagggggtgg aagtcctca aatattggtg gaatctccta | 2400 |
| cagtattgga gtcaggaact aaagagtagt gctgttagct tgcttaatgc cacagctata | 2460 |
| gcagtagctg aggggacaga tagggttata gaagtactgc aaagagctgg tagagctatt | 2520 |
| ctccacatac ctacaagaat aagacagggc ttggaaaggg ctttgctata a | 2571 |

<210> SEQ ID NO 4
<211> LENGTH: 2571
<212> TYPE: DNA
<213> ORGANISM: Artificial Sequence
<220> FEATURE:
<223> OTHER INFORMATION: Description of Artificial Sequence:
    SYNgp-160mn - codon optimised env sequence

<400> SEQUENCE: 4

| | |
|---|---|
| atgagggtga aggggatccg ccgcaactac cagcactggt ggggctgggg cacgatgctc | 60 |
| ctggggctgc tgatgatctg cagcgccacc gagaagctgt gggtgaccgt gtactacggc | 120 |
| gtgcccgtgt ggaaggaggc caccaccacc ctgttctgcg ccagcgacgc caaggcgtac | 180 |
| gacaccgagg tgcacaacgt gtgggccacc caggcgtgcg tgcccaccga ccccaacccc | 240 |
| caggaggtgg agctcgtgaa cgtgaccgag aacttcaaca tgtggaagaa caacatggtg | 300 |
| gagcagatgc atgaggacat catcagcctg tgggaccaga gcctgaagcc ctgcgtgaag | 360 |
| ctgaccccc tgtgcgtgac cctgaactgc accgacctga ggaacaccac caacaccaac | 420 |
| aacagcaccg ccaacaacaa cagcaacagc gagggcacca tcaagggcgg cgagatgaag | 480 |
| aactgcagct tcaacatcac caccagcatc cgcgacaaga tgcagaagga gtacgccctg | 540 |
| ctgtacaagc tggatatcgt gagcatcgac aacgacagca ccagctaccg cctgatctcc | 600 |
| tgcaacacca gcgtgatcac ccaggcctgc cccaagatca gcttcgagcc catcccatc | 660 |
| cactactgcg ccccgccgg cttcgccatc ctgaagtgca acgacaagaa gttcagcggc | 720 |
| aagggcagct gcaagaacgt gagcaccgtg cagtgcaccc acggcatccg gccggtggtg | 780 |
| agcacccagc tcctgctgaa cggcagcctg gccgaggagg aggtggtgat ccgcagcgag | 840 |
| aacttcaccg acaacgccaa gaccatcatc gtgcacctga tgagagcgt gcagatcaac | 900 |
| tgcacgcgtc ccaactacaa caagcgcaag cgcatccaca tcggcccgg cgcgccttc | 960 |
| tacaccacca gaacatcat cggcaccatc cgccaggccc actgcaacat ctctagagcc | 1020 |
| aagtggaacg acaccctgcg ccagatcgtg agcaagctga aggagcagtt caagaacaag | 1080 |
| accatcgtgt tcaaccagag cagcggcggc gaccccgaga tcgtgatgca cagcttcaac | 1140 |
| tgcggcggcg aattcttcta ctgcaacacc agcccctgt tcaacagcac ctggaacggc | 1200 |
| aacaacaccc tggacaacac caccggcagc aacaacaata ttaccctcca gtgcaagatc | 1260 |
| aagcagatca tcaacatgtg gcaggaggtg ggcaaggcca tgtacgcccc ccccatcgag | 1320 |
| ggccagatcc ggtgcagcag caacatcacc ggtctgctgc tgacccgcga cggcggcaag | 1380 |
| gacaccgaca ccaacgacac cgaaatcttc cgccccggcg gcggcgacat gcgcgacaac | 1440 |
| tggagatctg agctgtacaa gtacaaggtg gtgacgatcg agcccctggg cgtggccccc | 1500 |
| accaaggcca agcgccgcgt ggtgcagcgc gagaagcggg ccgccatcgg cgccctgttc | 1560 |
| ctgggcttcc tggggcggc gggcagcacc atggggccg ccagcgtgac cctgaccgtg | 1620 |
| caggcccgcc tgctcctgag cggcatcgtg cagcagcaga caacctcct ccgcgccatc | 1680 |
| gaggcccagc agcatatgct ccagctcacc gtgtggggca tcaagcagct ccaggcccgc | 1740 |

```
gtgctggccg tggagcgcta cctgaaggac cagcagctcc tgggcttctg gggctgctcc    1800
ggcaagctga tctgcaccac cacggtaccc tggaacgcct cctggagcaa caagagcctg    1860
gacgacatct ggaacaacat gacctggatg cagtgggagc gcgagatcga taactacacc    1920
agcctgatct acagcctgct ggagaagagc cagacccagc aggagaagaa cgagcaggag    1980
ctgctggagc tggacaagtg ggcgagcctg tggaactggt tcgacatcac caactggctg    2040
tggtacatca aatcttcat catgattgtg gcggcctgg tgggcctccg catcgtgttc      2100
gccgtgctga gcatcgtgaa ccgcgtgcgc cagggctaca gccccctgag cctccagacc    2160 cggcccccg tgccgcgcgg gcccgaccgc cccgagggca tcgaggagga gggcggcgag     2220
cgcgaccgcg acaccagcgg caggctcgtg cacggcttcc tggcgatcat ctgggtcgac    2280
ctccgcagcc tgttcctgtt cagctaccac caccgcgacc tgctgctgat cgccgcccgc    2340
atcgtggaac tcctaggccg ccgcggctgg gaggtgctga agtactggtg gaacctcctc    2400
cagtattgga gccaggagct gaagtccagc gccgtgagcc tgctgaacgc caccgccatc    2460
gccgtggccg agggcaccga ccgcgtgatc gaggtgctcc agagggccgg gagggcgatc    2520
ctgcacatcc ccacccgcat ccgccagggg ctcgagaggg cgctgctgta a             2571

<210> SEQ ID NO 5
<211> LENGTH: 9772
<212> TYPE: DNA
<213> ORGANISM: Artificial Sequence
<220> FEATURE:
<223> OTHER INFORMATION: Description of Artificial Sequence:pSYNGP

<400> SEQUENCE: 5
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca aacttacgg taaatggccc      240 gcctggctga ccgcccaacg acccccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccctattg acgtcaatga      420 cggtaaatgg cccgcctggc attatgccca gtacatgacc ttacgggact tcctacttg      480 gcagtacatc tacgtattag tcatcgctat taccatggtg atgcggtttt ggcagtacac     540
caatgggcgt ggatagcggt ttgactcacg gggatttcca agtctccacc ccattgacgt     600
caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
cttgcgtttc tgataggcac ctattggtct tactgacatc cactttgcct ttctctccac    1020
aggtgtccac tcccagttca attacagctc ttaaggctag agtacttaat acgactcact    1080
ataggctagc ctcgagaatt cgccaccatg ggcgcccgcg ccagcgtgct gtcgggcggc    1140
gagctggacc gctgggagaa gatccgcctg cgccccggcg gcaaaagaa gtacaagctg    1200 aagcacatcg tgtgggccag ccgcgaactg gagcgcttcg ccgtgaaccc cgggctcctg    1260
```

-continued

```
gagaccagcg agggggtgccg ccagatcctc ggccaactgc agcccagcct gcaaaccggc      1320
agcgaggagc tgcgcagcct gtacaacacc gtggccacgc tgtactgcgt ccaccagcgc      1380
atcgaaatca aggatacgaa agaggccctg gataaaatcg aagaggaaca gaataagagc      1440
aaaaagaagg cccaacaggc cgccgcggac accggacaca gcaaccaggt cagccagaac      1500
taccccatcg tgcagaacat ccaggggcag atggtgcacc aggccatctc cccccgcacg      1560
ctgaacgcct gggtgaaggt ggtggaagag aaggctttta gcccggaggt gatacccatg      1620
ttctcagccc tgtcagaggg agccacccccc caagatctga acaccatgct caacacagtg      1680
gggggacacc aggccgccat gcagatgctg aaggagacca tcaatgagga ggctgccgaa      1740
tgggatcgtg tgcatccggt gcacgcaggg cccatcgcac cgggccagat gcgtgagcca      1800
cggggctcag acatcgccgg aacgactagt acccttcagg aacagatcgg ctggatgacc      1860
aacaacccac ccatcccggt gggagaaatc tacaaacgct ggatcatcct gggcctgaac      1920
aagatcgtgc gcatgtatag ccctaccagc atcctggaca tccgccaagg cccgaaggaa      1980 cccttcgcg actacgtgga ccggttctac aaaacgctcc gcgccgagca ggctagccag      2040
gaggtgaaga actggatgac cgaaaccctg ctggtccaga acgcgaaccc ggactgcaag      2100
acgatcctga aggccctggg cccagcggct accctagagg aaatgatgac cgcctgtcag      2160
ggagtgggcg acccggcca aaggcacgc gtcctggctg aggccatgag ccaggtgacc      2220
aactccgcta ccatcatgat gcagcgcggc aactttcgga accaacgcaa gatcgtcaag      2280
tgcttcaact gtggcaaaga agggcacaca gcccgcaact gcagggcccc taggaaaaag      2340
ggctgttgga aatgtggaaa ggaaggacac caaatgaaag attgtactga gagacaggct      2400
aattttttag ggaagatctg gccttcccac aagggaaggc cagggaattt tcttcagagc      2460
agaccagagc caacagcccc accagaagag agcttcaggt ttgggaaga gacaacaact      2520 ccctctcaga agcaggagcc gatagacaag gaactgtatc ctttagcttc cctcagatca      2580
ctctttggca gcgaccccctc gtcacaataa agatagggg gcagctcaag gaggctctcc      2640
tggacaccgg agcagacgac accgtgctgg aggagatgtc gttgccaggc cgctggaagc      2700
cgaagatgat cggggggaatc ggcggttttca tcaaggtgcg ccagtatgac cagatccctca      2760 tcgaaatctg cggccacaag gctatcggta ccgtgctggt gggccccaca cccgtcaaca      2820
tcatcggacg caacctgttg acgcagatcg gttgcacgct gaacttcccc attagcccta      2880
tcgagacggt accggtgaag ctgaagcccg ggatggacgg cccgaaggtc aagcaatggc      2940
cattgacaga ggagaagatc aaggcactgg tggagatttg cacagagatg gaaaaggaag      3000
ggaaaatctc caagattggg cctgagaacc cgtacaacac gccggtgttc gcaatcaaga      3060
agaaggactc gacgaaatgg cgcaagctgg tggacttccg cgagctgaac aagcgcacgc      3120
aagacttctg ggaggttcag ctgggcatcc cgcaccccgc agggctgaag aagaagaaat      3180
ccgtgaccgt actggatgtg ggtgatgcct acttctccgt tccctggac gaagacttca      3240 ggaagtacac tgccttcaca atcccttcga tcaacaacga acaccgggg attcgatatc      3300 agtacaacgt gctgcccccag ggctggaaag ctctccccgc aatcttccag agtagcatga      3360
ccaaaatcct ggagcctttc cgcaaacaga accccgacat cgtcatctat cagtacatgg      3420
atgacttgta cgtgggctct gatctagaga tagggcagca ccgcaccaag atcgaggagc      3480
tgcgccagca cctgttgagg tggggactga ccacacccga caagaagcac cagaaggagc      3540 ctccccttcct ctggatgggt tacgagctgc accctgacaa atggaccgtg cagcctatcg      3600
```

-continued

| | |
|---|---|
| tgctgccaga gaaagacagc tggactgtca acgacataca gaagctggtg gggaagttga | 3660 |
| actgggccag tcagatttac ccagggatta aggtgaggca gctgtgcaaa ctcctccgcg | 3720 |
| gaaccaaggc actcacagag gtgatccccc taaccgagga ggccgagctc gaactggcag | 3780 |
| aaaaccgaga gatcctaaag gagcccgtgc acggcgtgta ctatgacccc tccaaggacc | 3840 |
| tgatcgccga gatccagaag cagggggcaag gccagtggac ctatcagatt taccaggagc | 3900 |
| ccttcaagaa cctgaagacc ggcaagtacg cccggatgag gggtgcccac actaacgacg | 3960 |
| tcaagcagct gaccgaggcc gtgcagaaga tcaccaccga agcatcgtg atctggggaa | 4020 |
| agactcctaa gttcaagctg cccatccaga aggaaacctg ggaaacctgg tggacagagt | 4080 |
| attggcaggc cacctggatt cctgagtggg agttcgtcaa caccccctcc ctggtgaagc | 4140 |
| tgtggtacca gctggagaag gagcccatag tgggcgccga aaccttctac gtggatgggg | 4200 |
| ccgctaacag ggagactaag ctgggcaaag ccggatacgt cactaaccgg ggcagacaga | 4260 |
| aggttgtcac cctcactgac accaccaacc agaagactga gctgcaggcc atttacctcg | 4320 |
| cttttgcagga ctcgggcctg gaggtgaaca tcgtgacaga ctctcagtat gccctgggca | 4380 |
| tcattcaagc ccagccagac cagagtgagt ccgagctggt caatcagatc atcgagcagc | 4440 |
| tgatcaagaa ggaaaaggtc tatctggcct gggtacccgc ccacaaaggc attggcggca | 4500 |
| atgagcaggt cgacaagctg gtctcggctg gcatcaggaa ggtgctattc ctggatggca | 4560 |
| tcgacaaggc ccaggacgag cacgagaaat accacagcaa ctggcgggcc atggctagcg | 4620 |
| acttcaacct gccccctgtg gtggccaaag agatcgtggc cagctgtgac aagtgtcagc | 4680 |
| tcaagggcga agccatgcat ggccaggtgg actgtagccc cggcatctgg caactcgatt | 4740 |
| gcacccatct ggagggcaag gttatcctgg tagccgtcca tgtggccagt ggctacatcg | 4800 |
| aggccgagt cattcccgcc gaaacagggc aggagacagc ctacttcctc ctgaagctgg | 4860 |
| caggccggtg gccagtgaag accatccata ctgacaatgg cagcaatttc accagtgcta | 4920 |
| cggttaaggc cgcctgctgg tgggcgggaa tcaagcagga gttcgggatc ccctacaatc | 4980 |
| cccagagtca gggcgtcgtc gagtctatga ataaggagtt aaagaagatt atcggccagg | 5040 |
| tcagagatca ggctgagcat ctcaagaccg cggtccaaat ggcggtattc atccacaatt | 5100 |
| tcaagcggaa gggggggatt gggggggtaca gtgcggggga gcggatcgtg gacatcatcg | 5160 |
| cgaccgacat ccagactaag gagctgcaaa agcagattac caagattcag aatttccggg | 5220 |
| tctactacag ggacagcaga aatcccctct ggaaaggccc agcgaagctc ctctggaagg | 5280 |
| gtgaggggc agtagtgatc caggataata gcgacatcaa ggtggtgccc agaagaaagg | 5340 |
| cgaagatcat tagggattat ggcaaacaga tggcgggtga tgattgcgtg gcgagcagac | 5400 |
| aggatgagga ttaggaattg ggctagagcg gccgcttccc tttagtgagg gttaatgctt | 5460 |
| cgagcagaca tgataagata cattgatgag tttggacaaa ccacaactag aatgcagtga | 5520 |
| aaaaaatgct ttatttgtga aatttgtgat gctattgctt tatttgtaac cattataagc | 5580 |
| tgcaataaac aagttaacaa caacaattgc attcatttta tgtttcaggt tcaggggggag | 5640 |
| atgtgggagg ttttttaaag caagtaaaac ctctacaaat gtggtaaaat ccgataagga | 5700 |
| tcgatccggg ctggcgtaat agcgaagagg cccgcaccga tcgcccttcc caacagttgc | 5760 |
| gcagcctgaa tggcgaatgg acgcgccctg tagcggcgca ttaagcgcgg cgggtgtggt | 5820 |
| ggttacgcgc agcgtgaccg ctacacttgc cagcgcccta gcgcccgctc ctttcgcttt | 5880 |
| cttcccttcc tttctcgcca cgttcgccgg ctttccccgt caagctctaa atcggggggct | 5940 |
| ccctttaggg ttccgattta gagctttacg gcacctcgac cgcaaaaaac ttgatttggg | 6000 |

```
tgatggttca cgtagtgggc catcgccctg atagacggtt tttcgccctt tgacgttgga    6060
gtccacgttc tttaatagtg gactcttgtt ccaaactgga acaacactca accctatctc    6120
ggtctattct tttgatttat aagggatttt gccgatttcg gcctattggt taaaaatga     6180 gctgatttaa caaatattta acgcgaattt aacaaaata ttaacgttta caatttcgcc     6240
tgatgcggta ttttctcctt acgcatctgt gcggtatttc acaccgcata cgcggatctg    6300
cgcagcacca tggcctgaaa taacctctga agaggaact tggttaggta ccttctgagg     6360
cggaaagaac cagctgtgga atgtgtgtca gttagggtgt ggaaagtccc caggctcccc    6420
agcaggcaga agtatgcaaa gcatgcatct caattagtca gcaaccaggt gtggaaagtc    6480
cccaggctcc ccagcaggca gaagtatgca aagcatgcat ctcaattagt cagcaaccat    6540
agtcccgccc ctaactccgc ccatcccgcc ctaactccg cccagttccg cccattctcc     6600
gccccatggc tgactaattt tttttattta tgcagaggcc gaggccgcct cggcctctga    6660
gctattccag aagtagtgag gaggcttttt tggaggccta ggcttttgca aaaagcttga    6720
ttcttctgac acaacagtct cgaacttaag gctagagcca ccatgattga acaagatgga    6780
ttgcacgcag gttctccggc cgcttgggtg gagaggctat tcggctatga ctgggcacaa    6840
cagacaatcg gctgctctga tgccgccgtg ttccggctgt cagcgcaggg gcgcccggtt    6900 cttttttgtca agaccgacct gtccggtgcc ctgaatgaac tgcaggacga ggcagcgcgg    6960
ctatcgtggc tggccacgac gggcgttcct tgcgcagctg tgctcgacgt tgtcactgaa    7020
gcgggaaggg actggctgct attgggcgaa gtgccggggc aggatctcct gtcatctcac    7080
cttgctcctg ccgagaaagt atccatcatg gctgatgcaa tgcggcggct gcatacgctt    7140
gatccggcta cctgcccatt cgaccaccaa gcgaaacatc gcatcgagcg agcacgtact    7200
cggatggaag ccggtcttgt cgatcaggat gatctggacg aagagcatca ggggctcgcg    7260
ccagccgaac tgttcgccag gctcaaggcg cgcatgcccg acggcgagga tctcgtcgtg    7320
acccatggcg atgcctgctt gccgaatatc atggtggaaa atggccgctt ttctggattc    7380
atcgactgtg gccggctggg tgtggcggac cgctatcagg acatagcgtt ggctacccgt    7440
gatattgctg aagagcttgg cggcgaatgg gctgaccgct tcctcgtgct ttacggtatc    7500
gccgctcccg attcgcagcg catcgccttc tatcgccttc ttgacgagtt cttctgagcg    7560
ggactctggg gttcgaaatg accgaccaag cgacgcccaa cctgccatca cgatggccgc    7620
aataaaatat ctttattttc attacatctg tgtgttggtt ttttgtgtga atcgatagcg    7680
ataaggatcc gcgtatggtg cactctcagt acaatctgct ctgatgccgc atagttaagc    7740
cagccccgac acccgccaac acccgctgac gcgccctgac gggcttgtct gctcccggca    7800
tccgcttaca gacaagctgt gaccgtctcc gggagctgca tgtgtcagag gttttcaccg    7860
tcatcaccga aacgcgcgag acgaaagggc ctcgtgatac gcctattttt ataggttaat    7920
gtcatgataa taatggtttc ttagacgtca ggtggcactt ttcggggaaa tgtgcgcgga    7980
acccctattt gtttattttt ctaaatacat tcaaatatgt atccgctcat gagacaataa    8040
ccctgataaa tgcttcaata atattgaaaa aggaagagta tgagtattca acatttccgt    8100
gtcgccctta ttcccttttt tgcggcattt tgccttcctg tttttgctca cccagaaacg    8160
ctggtgaaag taaaagatgc tgaagatcag ttgggtgcac gagtgggtta catcgaactg    8220
gatctcaaca gcggtaagat ccttgagagt tttcgccccg aagaacgttt tccaatgatg    8280 agcacttttaa aagttctgct atgtggcgcg gtattatccc gtattgacgc cgggcaagag    8340
```

-continued

```
caactcggtc gccgcataca ctattctcag aatgacttgg ttgagtactc accagtcaca    8400
gaaaagcatc ttacggatgg catgacagta agagaattat gcagtgctgc cataaccatg    8460
agtgataaca ctgcggccaa cttacttctg acaacgatcg gaggaccgaa ggagctaacc    8520
gcttttttgc acaacatggg ggatcatgta actcgccttg atcgttggga accggagctg    8580
aatgaagcca taccaaacga cgagcgtgac accacgatgc ctgtagcaat ggcaacaacg    8640
ttgcgcaaac tattaactgg cgaactactt actctagctt cccggcaaca attaatagac    8700
tggatggagg cggataaagt tgcaggacca cttctgcgct cggcccttcc ggctggctgg    8760
tttattgctg ataaatctgg agccggtgag cgtgggtctc gcggtatcat tgcagcactg    8820
gggccagatg gtaagccctc ccgtatcgta gttatctaca cgacggggag tcaggcaact    8880
atggatgaac gaaatagaca gatcgctgag ataggtgcct cactgattaa gcattggtaa    8940
ctgtcagacc aagtttactc atatatactt tagattgatt taaaacttca ttttaattt    9000 aaaaggatct aggtgaagat cctttttgat aatctcatga ccaaaatccc ttaacgtgag    9060
ttttcgttcc actgagcgtc agaccccgta gaaaagatca aggatcttc ttgagatcct    9120 ttttttctgc gcgtaatctg ctgcttgcaa acaaaaaaac caccgctacc agcggtggtt    9180
tgtttgccgg atcaagagct accaactctt tttccgaagg taactggctt cagcagagcg    9240
cagataccaa atactgtcct tctagtgtag ccgtagttag gccaccactt caagaactct    9300
gtagcaccgc ctacatacct cgctctgcta atcctgttac cagtggctgc tgccagtggc    9360
gataagtcgt gtcttaccgg gttggactca agacgatagt taccggataa ggcgcagcgg    9420
tcgggctgaa cggggggttc gtgcacacag cccagcttgg agcgaacgac ctacaccgaa    9480
ctgagatacc tacagcgtga gctatgagaa agcgccacgc ttcccgaagg gagaaaggcg    9540
gacaggtatc cggtaagcgg cagggtcgga acaggagagc gcacgaggga gcttccaggg    9600
ggaaacgcct ggtatcttta tagtcctgtc gggtttcgcc acctctgact tgagcgtcga    9660
tttttgtgat gctcgtcagg gggcggagc ctatggaaaa acgccagcaa cgcggccttt    9720
ttacggttcc tggccttttg ctggcctttt gctcacatgg ctcgacagat ct            9772
```

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence:ribozyme
      hammerhead helix II

<400> SEQUENCE: 6
cugaugaggc cgaaaggccg aa                                             22

<210> SEQ ID NO 7
<211> LENGTH: 22
<212> TYPE: RNA
<213> ORGANISM: Artificial Sequence
<220> FEATURE:
<223> OTHER INFORMATION: Description of Artificial Sequence:cleavage
                  site GAG 1

<400> SEQUENCE: 7
uaguaagaau guauagcccu ac                                             22

<210> SEQ ID NO 8
<211> LENGTH: 22
<212> TYPE: RNA
<213> ORGANISM: Artificial Sequence

```
<220> FEATURE:
<223> OTHER INFORMATION: Description of Artificial Sequence:cleavage
      site GAG 2

<400> SEQUENCE: 8
aacccagauu guaagacuau uu                                              22

<210> SEQ ID NO 9
<211> LENGTH: 22
<212> TYPE: RNA
<213> ORGANISM: Artificial Sequence
<220> FEATURE:
<223> OTHER INFORMATION: Description of Artificial Sequence:cleavage
      site GAG 3

<400> SEQUENCE: 9
uguuucaauu guggcaaaga ag                                              22

<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence:cleavage
      site GAG 4

<400> SEQUENCE: 10
aaaaagggcu guuggaaaug ug                                              22

<210> SEQ ID NO 11
<211> LENGTH: 22
<212> TYPE: RNA
<213> ORGANISM: Artificial Sequence
<220> FEATURE:
<223> OTHER INFORMATION: Description of Artificial Sequence:cleavage
      site POL 1

<400> SEQUENCE: 11
acgaccccuc gucacaauaa ag                                              22

<210> SEQ ID NO 12
<211> LENGTH: 22
<212> TYPE: RNA
<213> ORGANISM: Artificial Sequence
<220> FEATURE:
<223> OTHER INFORMATION: Description of Artificial Sequence:cleavage
      site POL 2

<400> SEQUENCE: 12
ggaauuggag guuuuaucaa ag                                              22

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence:cleavage
      site POL 3

<400> SEQUENCE: 13
auauuuuuca guuccuuag au                                               22

<210> SEQ ID NO 14
<211> LENGTH: 22
<212> TYPE: RNA
<213> ORGANISM: Artificial Sequence
<220> FEATURE:
```

```
<223> OTHER INFORMATION: Description of Artificial Sequence:cleavage
      site POL 4

<400> SEQUENCE: 14
uggaugauuu guauguagga uc                                              22

<210> SEQ ID NO 15
<211> LENGTH: 22
<212> TYPE: RNA
<213> ORGANISM: Artificial Sequence
<220> FEATURE:
<223> OTHER INFORMATION: Description of Artificial Sequence:cleavage
      site POL 5

<400> SEQUENCE: 15
cuuuggaugg guuaugaacu cc                                              22

<210> SEQ ID NO 16
<211> LENGTH: 22
<212> TYPE: RNA
<213> ORGANISM: Artificial Sequence
<220> FEATURE:
<223> OTHER INFORMATION: Description of Artificial Sequence:cleavage
      site POL 6

<400> SEQUENCE: 16
cagcuggacu gucaaugaca ua                                              22

<210> SEQ ID NO 17
<211> LENGTH: 22
<212> TYPE: RNA
<213> ORGANISM: Artificial Sequence
<220> FEATURE:
<223> OTHER INFORMATION: Description of Artificial Sequence:cleavage
      site POL 7

<400> SEQUENCE: 17
aacuuucuau guagaugggg ca                                              22

<210> SEQ ID NO 18
<211> LENGTH: 22
<212> TYPE: RNA
<213> ORGANISM: Artificial Sequence
<220> FEATURE:
<223> OTHER INFORMATION: Description of Artificial Sequence:cleavage
      site POL 8

<400> SEQUENCE: 18
aaggccgccu guuggugggc ag                                              22

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence:cleavage
      site POL9

<400> SEQUENCE: 19
uaagacagca guacaaaugg ca                                              22

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:primer RIB1
```

```
<400> SEQUENCE: 20
cagctgctcg agcagctgaa gcttgcatgc                                30

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence:primer RIB2

<400> SEQUENCE: 21
gtaagttatg taacggacga tatcttgtct tctt                           34

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence:primer RIB3

<400> SEQUENCE: 22
cgcatagtcg acgggcccgc cactgctaga gattttc                        37
```